(12) United States Patent
Bauer et al.

(10) Patent No.: US 7,465,806 B2
(45) Date of Patent: Dec. 16, 2008

(54) PYRROLE-DERIVATIVES AS FACTOR XA INHIBITORS

(75) Inventors: Armin Bauer, Sulzbach/Ts (DE); Michael Wagner, Alsbach (DE); Marc Nazare, Idstein (DE); Volkmar Wehner, Sandberg (DE); Matthias Urmann, Eschborn (DE); Hans Matter, Langenselbold (DE)

(73) Assignee: SANOFI-AVENTIS Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/467,277

(22) Filed: Aug. 25, 2006

(65) Prior Publication Data
US 2007/0049573 A1 Mar. 1, 2007

Related U.S. Application Data

(63) Continuation of application No. PCT/EP2005/001423, filed on Feb. 12, 2005.

(30) Foreign Application Priority Data
Feb. 27, 2004 (EP) .................................. 04004503

(51) Int. Cl.
C07D 261/06 (2006.01)
C07D 207/32 (2006.01)
(52) U.S. Cl. ...................................... 548/247; 548/537
(58) Field of Classification Search ................. 548/247, 548/537
See application file for complete search history.

(56) References Cited

U.S. PATENT DOCUMENTS

| 6,020,357 | A | 2/2000 | Pinto et al. |
| 6,906,084 | B2 | 6/2005 | Nazaré |
| 6,953,857 | B2 | 10/2005 | Nazaré |
| 7,067,665 | B2 | 6/2006 | Nazaré |
| 7,229,780 | B2 | 5/2007 | Nazaré |
| 7,317,027 | B2 | 1/2008 | Nazaré |
| 7,358,268 | B2 | 4/2008 | Nazaré |
| 7,365,088 | B2 | 4/2008 | Nazaré |
| 2002/0165203 | A1 | 11/2002 | Arnaiz et al. |
| 2004/0204406 | A1 | 10/2004 | Nazaré |
| 2005/0009829 | A1 | 1/2005 | Nazaré |
| 2005/0043302 | A1 | 2/2005 | Nazaré |
| 2007/0179122 | A1 | 8/2007 | Urmann |

FOREIGN PATENT DOCUMENTS

| EP | 0987274 | 3/2000 |
| EP | 1072263 | 1/2001 |
| EP | 1176140 | 1/2002 |
| EP | 1388341 | 2/2004 |
| WO | WO 92/06711 | 4/1992 |
| WO | WO 95/29189 | 11/1995 |
| WO | WO 96/12800 | 5/1996 |
| WO | WO 97/47651 | 12/1997 |
| WO | WO 98/28269 | 7/1998 |
| WO | WO 99/32454 | 7/1999 |
| WO | WO 01/32628 | 5/2001 |
| WO | WO 01/70671 | 9/2001 |
| WO | WO 02/053155 | 7/2002 |
| WO | WO 02/053157 | 7/2002 |
| WO | 02/064545 | 8/2002 |
| WO | 02/064546 | 8/2002 |
| WO | WO 03/044014 | 5/2003 |
| WO | WO 2004/018455 | 3/2004 |
| WO | WO 2004/039318 | 5/2004 |

OTHER PUBLICATIONS

A. Hantzsch, Neue Bildungsweiss von Pymolderivaten, Ber. Disch. Chem. Gss, (1890, pp. 1474-1476, vol. 23).

(Continued)

Primary Examiner—Kamal Saeed
Assistant Examiner—Robert Havlin
(74) Attorney, Agent, or Firm—Ronald G. Ort

(57) ABSTRACT

The present invention relates to compounds of the formulae I and Ia,

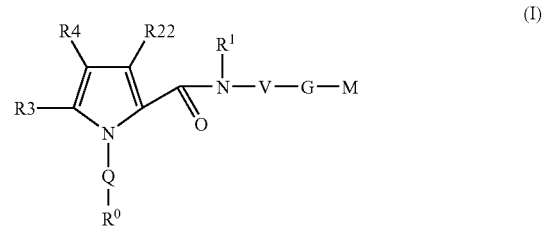

(I)

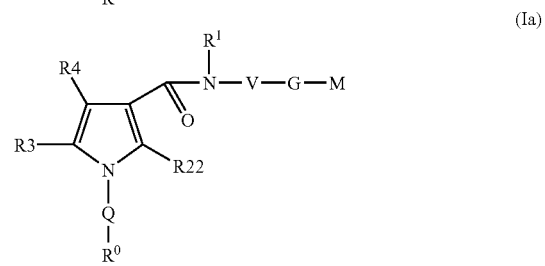

(Ia)

wherein $R^0$; $R^1$; R3; R4; R22, Q; V, G and M have the meanings indicated in the claims. The compounds of the formulae I and Ia are valuable pharmacologically active compounds. They exhibit a strong antithrombotic effect and are suitable for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formulae I and Ia, their use, in particular as active ingredients in pharmaceuticals, and pharmaceutical preparations comprising them.

9 Claims, No Drawings

OTHER PUBLICATIONS

A. Romeo et al., Thallium in Organic Synthesis Preparation of Steroidal 1,4-Dien-3-Ones, Tetrahedron (1972, pp. 6337-6339, vol. 28).

Akio Minato et al., Palladium-Phosphine Complex Catalyzed Cross-Coupling Reaction of 1-Methyl-2-Pyrrolyl-Magnesium Bromide and Zinc Chloride with Organic Halides, Tetrahedron Letters (1981, pp. 5319-5322, vol. 22, issue 52).

Alois Furstner et al., A Convenient Preparation of Functionalized Arylzino Compounds by the Reaction of Zinc/Silver-Graphic with Aryl Iodides, Tetrahedron Latter (1994, pp. 1047-1050, vol. 35).

Anton E.P Adang et al., A new generation of orally active antithrombotics: comparing strategies in the GPllb/llla, thrombin and factor Xa areas, Drugs of the Future (2000, pp. 369-383, vol. 25, issue 4).

Artis Klapars et al., A General and Efficient Copper Catalyst for the Amidation of Aryl Halides and the N-Arylation of Nitrogen Heterocycles, J. Am. Chem. Soc. (2001, pp. 7727-7729, vol. 123).

Bossio, et al., Studies on Isocyanides and related Compounds: A Novel Synthesis of Pyrroiss via Ugi Reaction, Synthesis: 1994: (8) pp. 765-766.

Bryant H. Yang et al., Palladium-catalyzed amination of aryl halides and sulfonates, Journal Of Organometallic Chemistry (1999, pp. 125-146, vol. 578).

Chan, et al., New N- And O-Arylations With Phenylboronic Acids And Cupric Acetate, Tetrahedron Letters 39 (1998) 2933-2936.

Chemcats, XP-002299428, Chemcats: Accession No. 2004-2160975.

Chemcats, XP-002299429, Chemcats: Accession No. 2003:595723.

Chemcats, XP-002311478, Chemcats: Accession No. 2004:3649974.

D. S. Black, Hetareness and Related Ring Systems, Science of Synthesis (2002, pp. 441-552, vol. 9).

Daan Van Leusen et al., Synthetic Uses of Tosylmethyl isocyanide (TosMIC), Organic Reactions (2001, pp. 417-666, vol. 57).

Daniel M. Ketcha, Five Membered Ring Systems: Pyrroles and Benzo Derivatives, Process in Heterocyclic Chemistry (2002, pp. 114-138, vol. 14).

Daniel M. Ketcha, Five Membered Ring Systems: Pyrroles and Benzo Derivatives, Progress in Heterocyclic Chemistry (2000, pp. 114-133, vol. 12).

Daniel M. Ketcha, Five Membered Ring Systems: Pyrroles and Benzo Derivatives, Progress in Heterocyclic Chemistry (2001, pp. 111-129, vol. 13).

Danielle R. Soenen et al., Multidrug Resistance Reversal Activity on key Ningalin Analogues, Bioorganic & Medicinal Chemistry Letters (2003, pp. 1777-1781, vol. 13).

David E. Nichols et al., 1-(2,5-Dimethoxy-4-(trifluoromethyl)-2-aminopropane; A Potent Serotonin 5-HT2A/2C Agonist, J. Med. Chem. (1994, pp. 4336-4351, vol. 37).

David Fleisher et al., Improved oral drug delivery: solubility limitations overcome by the use of prodrugs, Advanced Drug Delivery Reviews (1996, pp. 115-130; vol. 19).

David W. Old et al., Efficient Palladium-Catalyzed N-Arylation of Indoies, Organic Letters (2000, pp. 1403-1406, vol. 2, No. 10).

De-Bao Su et al., Methyl Chlorodifluoroacetate A Convenient Trifluoromethylating Agent, Tetrahedron Letters, (1991, pp. 7689-7690, vol. 32, No. 52).

Donato Monti et al., Thallium in Pyrrole Chemistry, Formation of C-Pyrrylthallium Derivatives, Gazzette Chimica Italiana, (1990, pp. 587-590, vol. 120).

F. Diedrich et al., Metal-catalyzed Cross-coupling, Wiley-VCH (1998, pp. 491-517).

Feng-Ling Oing et al., First Synthesis of ortho-trifluoromethylated aryl triflates; J. Chem. Soc. Perkin Trans. (1997, pp. 3053-3057, vol. 1).

Fuk Yee Kwong et al., Copper-Catalyzed Coupling of Alkylamines and Aryl Iodides: An Efficient System Even in an Air Atmosphere, Organic Letters (2002, pp. 581-584, vol. 4, issue 4).

Gennadii P. Tokmakov et al., Rearrangement of 1-Arylindoles to 5H-Dibenz[b,f]azepines, Tetrahedron (1995, pp. 2091-2098, vol. 51).

Grace Mann et al., Palladium-Catalyzed C-N(sp2) Bond Formation: N-Arylation of Aromatic and Unsaturated Nitrogen and the Reductive Elimination Chemistry of Palladium Azolyl and Methylenamino Complexes, J. Am. Chem. Sec. (1998, pp. 827-828, vol. 120).

Gul Hassan Walizei et al., Pyrrole aus 3-Alkoxyacroleinen und CH-aciden alpha-Aminoessigsaure-Derivaten, Synthesis (1989, pp. 337-340).

H. M. Gilow et al., Bromination and Chlorination of Pyrrole and Some Reactive 1-Substituted Pyrroles J. Org. Chem. (1981, pp. 2221-2225, vol. 46).

H. Stetter et al., Eng. Transcript of 4-Oxo-4.5,6.7-Tetrahydro-indole Und 4-Oxo-1.2.3.4.5.6.7.8-Octahydro-Carbazole, Liebigs Ann. Chem. (1962, pp. 20-26, vol. 555).

Hans Bundgaard, Novel chemical approaches in prodrug design, Drugs of the Future (1991, pp. 443-458, vol. 16).

Hermann K. Hombrecher et al., Synthesis of Pyrroles via Ethyl N-(3-Oxo-1-alkenyl)glycinates, Synthesis (1990, pp. 389-391).

Hisanobu Ogoshi et al., Synthesis of Beta-Trifluoromethylptrroles, Tetrahedron Letter (1983, pp. 929-930, vol. 24).

Hisao Urata et al., A Novel and Convenient Method for Trifluoromethylation of organic hallides using CF3SiR3KF/Cu(1) System, Tetrahedron Letters, (1991, pp. 91-94, vol. 32, No. 1).

Hugh J. Anderson et al., The Preparation and Some Reactions Of Brominated Pyrroles Derivatives, Can. J. Chem. (1965, pp. 409-414, vol. 43).

Irwin H. Segel, Simple Inhibition Systems, Enzyme Kinetics (1975, pp. 100-125).

James M. Hamby et al., alpha-amino ketones from amino acids as precursors for the knorr pyrrole synthesis, Heterocycles, (1993, pp. 843-850, vol. 35).

James P. Collman et al., Catalytic Activities of Cu(ll) Compiexes with Nitrogen-Chelating Bidentate Ligands in the Coupling of Imidazoies with Arylboronic Acids, J. Org. Chem. (2001, pp. 7892-7897, vol. 66).

Jane A. Ganske et al., Some Mercuration Reactions of Substituted Pyrroles, J. Org. Chem. (1989, pp. 4801-4807, vol. 54).

Jianji Wang et al., Fluoro-decarboxylation of Pyrrolecarboxylic Acids by F-TEDA-BF4-A-Convenient General Synthesis of Fluoropyrroles, J. Chem. Soc., Chem. Commun. (1995, pp. 2399-2400).

Jianji Wang et al., Synthesis of the 2-Fluoro-11-hydroxy Analog of Porphobillnogen, a New Suicide Inhibitor of the Enzyme Porphobilinogen Deaminase, Tetrahedron (1994, pp. 6181-6192, vol. 50, issue 21).

John F. Hartwig et al., Room-Temperature Palladium-Catalyzed Amination of Aryl Bromides and Chlorides and Extended Scope of Aromatic C-N Bond Formation with a Commerical Ligand, J. Org. Chem. (1999, pp. 5575-5580, vol. 54).

John F. Hartwig, Eng. Transcript of Ubergangsmetall-katalyslerte Synthese von Arylaminen und Arylethem aus Arythalogeniden und-triflaten; Anwendungen und Reaktionsmechanismus, Angew. Chem. (1998, pp. 2154-2177, vol. 110).

John P. Wolfe et al., Simple, Efficient Catalyst System for the Palladium-Catalyzed Amination of Aryl Chlorides, Bromides, and Triflates, J. Org. Chem. (2000, pp. 1158-1174, vol. 65).

John V. Cooney et al., The Synthesis of Knorr's Pyrrole by Inverse Addition, Org. Prep. Proced. Int. (1983, pp. 292-295, vol. 15, issue 4).

Junya Ohmori et al., Novel AMPA Receptor Antagonists: Synthesis and Structure-Activity Relationships of 1-Hydroxy-7-(1H-imidazol-1-yl)-6-nitro-2,3(1H,4H)-quinoxalinedione and Related Compounds, J. Med. Chem. (1996, pp. 3971-3979, vol. 39).

M. T. Cocco et al., Synthesis and Biological Activity of Some Pyrrole Derivatives, Farmaco Ed. Sci. (1986, 103-112, vol. 43).

Masaki Yamada et al., 2-[(2-Aminobenzyl) sulfinyl]-1-(2-pyridyl)-1,4,5,6-tetrahydrocyclopent[d]imidazoles as a Novel Class of Gastric H+/K+−ATPase Inhibitors, J. Med. Chem. (196, pp. 596-604), vol. 39).

Maurizio D'Auria et al., Photochemical Substitution of Halogenopyrrole Derivatives, J. Chem. Soc. Perkin Trans (1997, pp. 2369-2373, vol. 1).

P. Cozzi et al., Ethyl 2-[[5,6-Dihydro-7-(1H-Imidazol-1-YL)-2-Naphthalenyl], Oxy]-2-Methylpropanoate as a New Patent Oxyisobutyrate Hypolipidaemic with Unusual Features, Famaco (1987, pp. 205-216, vol. 42).

Patrick Y. S. Lam et al., New Aryl/Heteroaryl C-N Bond Cross-coupling Reactions via Arylboronic Acid/Cupric Acetate Arylation, Tetrahedron Letters (1998, pp. 2941-2944, vol. 39).

Paul C. Unangst et al., Synthesis of Novel 1-Phenyl-1H-indole-2-carboxylic Acids, I. Utilization of Ullmann and Dieckmann Reactions for the Preparation of 3-Hydroxy, 3-Alkoxy, and 3-Alkyl Derivatives, J. Heterocycl. Chem. (1987, pp. 811-815, vol. 24).

Richard C. Larock et al., Addition of H-X Reagents to Alkenes and Alkynes, Comprehensive Organic Synthesis (1999, pp. 269-326).

Robert L. Wineholt et al., Heterocyclic Studies XXI, 1,2,3,7-Tetrahydro-l-acyl-7-methoxy-5-methyl-6-phenyl-4H-1,2-diazepin-4-ones, Journal Org. Chem. (1996, pp. 48-52, vol. 31).

S. Petruso et al., Oxidative Halogenation of Substituted Pyrroles with Cu(ii), Part 1 Bromination of some 3-Acetylpyrroles, J. Heterocycl, (1990, pp. 1209-1211, vol. 27).

Shuntaro Mataka et al., Preparation of Ethyl 3,5-Disubstituted Pyrrole-2-carboxylates from 1,3-Diketones and Ethyl Glycinate Hydrochloride, Synthesis (1962, pp. 157-159).

Srivastava A.K. et al., Quantitative Structure Activity Relationship (OSAR) studies on anti-HIV-1 and cytotoxic arylpyrrolylsulfories, Journal of the Indian Chemical Society (2001, pp. 154-157, vol. 78 (3).

Takao Sakamoto et al., Palladium-catalyzed cyanation of aryl and heteroaryl Iodides with copper(1) cyanide, J. Chem. Soc. Perkin Trans (1999, pp. 2323-2326).

Tetsuzo Kato et al., Studies on Katene and its Derivatives. XL91) Reaction of alpha-Aminoketone with Diketene, Chem. Pharm. Bull (1971, pp. 292-296, vol. 19).

Theodora W. Greene et al., Protective Groups in Organic Synthesis. 3rd ed., Wiley, John Wiley & Sons, Inc. (1999, pp. 5-20).

Vitor F. Ferreira et al., Recent Advances in the Synthesis of Pyrroles, Organic Preparation and Procedures Inc. (2001, pp. 411-454, vol. 33).

W. Lubisch et al., Pyrrolylquinoxalinediones: The importance of pyrrolic substitution of AMP receptor binding, Bioorganic & Medicinal Chemistry Letters (1997, pp. 1101-1106, vol. 7, No. 9).

Wayne J. Thompson et al., Preparation of Methyl 2,5-Dioxohexnoate: A Highly Convenient Reagent for the Introduction of the 2-Carboalkoxy-1.5- dialkylpyrrole Nucleus, J. Org. Chem. (1983, pp. 2769-2772, vol. 48).

Werner W.K.R. Mederski et al., N-Aryl Heterocycles via Coupling Reactions with Arylboronic Acids, Tetrahedron (1999, pp. 12757-12770, vol. 55).

Yung-Chi Cheng et al., Relationship Between the inhibition Constant (K1) and the Concentration of Inhibition Which Causes 50 per cent inhibition (150) of an Enzymatic Reaction, Biochemical Pharmacology, (1973, pp. 3099-3108, vol. 22).

PYRROLE-DERIVATIVES AS FACTOR XA INHIBITORS

This application is a Continuation of International Application No. PCT/EP2005/001423, filed Feb. 12, 2005.

FIELD OF THE INVENTION

The present invention relates to compounds of the formulae I and Ia,

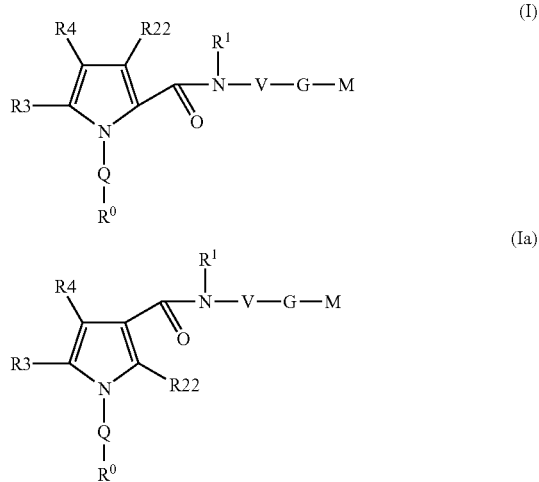

in which $R^0$; $R^1$; R3; R4; R22Q; V, G and M have the meanings indicated below. The compounds of the formulae I and Ia are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formulae I and Ia, their use, in particular as active ingredients in pharmaceuticals, and pharmaceutical preparations comprising them.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369-383).

Low molecular weight, factor Xa-specific blood clotting inhibitors that are effective but do not cause unwanted side effects have been described, for example, in WO-A-95/29189. However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa. However, the property profile of these compounds is still not ideal, and there is an ongoing need for further low molecular weight factor VIIa inhibitory blood clotting inhibitors The present invention satisfies the above needs by providing novel compounds of the formulae I and Ia, which exhibit better factor Xa and/or factor VIIa inhibitory activity and are favorable agents with high bioavailability.

SUMMARY OF THE INVENTION

Thus, the present invention relates to compounds of the formulae I and Ia,

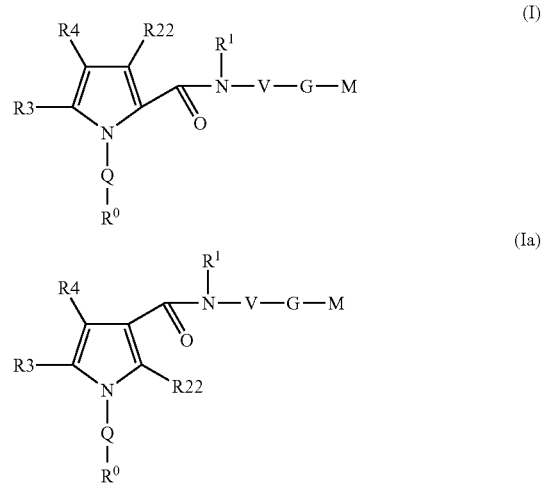

$R^0$ is 1) a monocyclic or bicyclic 6- to 14-membered aryl, wherein aryl is mono-, di- or trisubstituted independently of one another by R8,
2) a monocyclic or bicyclic 4- to 15-membered heterocyclyl out of the group pyridinyl, pyrimidinyl, indolyl, isoindolyl, indazolyl, phthalazinyl, quinolyl, isoquinolyl, benzothiophen, quinazolinyl and phenylpyridyl, wherein said heterocyclyl is unsubstituted or mono-, di- or trisubstituted independently of one another by R8, or
3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is 1) halogen,
2) —$NO_2$,
3) —OH,
4) —O—$CF_3$
5) a monocyclic or bicyclic 6- to 14-membered aryl, wherein aryl is mono-, di- or trisubstituted independently of one another by halogen or —O—($C_1$-$C_8$)-alkyl,
6) —($C_1$-$C_8$)-alkyl, wherein alkyl is unsubstituted or mono-, di- or trisubstituted independently of one another by halogen, —OH or a methoxy residue,
7) —O—($C_1$-$C_8$)-alkyl, wherein alkyl is unsubstituted or mono-, di- or trisubstituted independently of one another by halogen, $NH_2$, —OH or a methoxy residue,
8) —$SO_2$—$CH_3$ or
9) —$SO_2$—$CF_3$,
provided that R8 is at least one halogen or —O—($C_1$-$C_8$)-alkyl residue, if $R^0$ is a monocyclic or bicyclic 6- to 14-membered aryl, Q is —($C_0$-$C_2$)-alkylene-C(O)—$NR^{10}$—, —$NR^{10}$—C(O)—$NR^{10}$—, —$NR^{10}$—C(O)—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O) —$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or —($C_0$-$C_3$)-alkylene-C(O)—O—$(CH_2)_m$—,
wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —($C_3$-$C_6$)-cycloalkylen, wherein cycloalkylen is unsubstituted or mono-, di- or trisubstituted independently of one another by halogen, —$NH_2$ or —OH;

$R^1$ is a hydrogen atom, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—$R^{10}$, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —($C_1$-$C_3$)-perfluoroalkylene; —($C_1$-$C_3$)-alkylene-S(O) —($C_1$-$C_4$)-alkyl; —($C_1$-$C_3$)-alkylene-S(O)$_2$ —($C_1$-$C_3$)-alkyl; —($C_1$-$C_3$)-alkylene-S(O)$_2$—N($R^{4'}$)—$R^{5'}$; —($C_1$-$C_3$)-alkylene-O—($C_1$-$C_4$)-alkyl; —($C_0$-$C_3$)-alkylene-($C_3$-$C_8$)-cycloalkyl or —($C_0$-$C_3$)-alkylene-het, wherein het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, $R^{4'}$ and $R^5$ are independent of one another are identical or different and are hydrogen atom or —($C_1$-$C_4$)-alkyl, or $R^1$ and R22 together with the atoms to which they are bonded can form a 6- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, or $R^1$—N—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —($C_1$-$C_8$)-alkyl, —($C_1$-$C_4$)-alkoxy, —$NO_2$, —($C_0$-$C_4$)-alkyl-C(O)—O—$R^{18}$, —CN, —($C_0$-$C_4$)-alkyl-N($R^{18}$)—$R^{21}$, —($C_0$-$C_4$)-alkyl-O—$R^{18}$, —($C_0$-$C_4$)-alkyl-het, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$,
wherein $R^{18}$ and $R^{21}$ are independently from each other hydrogen atom, —($C_1$-$C_3$)-perfluoroalkyl or —($C_1$-$C_6$)-alkyl, V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, or
2) a monocyclic or bicyclic 4- to 15-membered heterocyclyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O) —$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—, n and m are independently of one another identical or different and are the integers zero, 1, 2, 3, 4, 5 or 6, M is 1) a hydrogen atom,
2) —($C_1$-$C_8$)-alkyl, wherein alkyl is unsubstituted or mono-, di- or trisubstituted independently of one another by R14,
3) —C(O)—N($R^{11}$)—$R^{12}$,
4) —$(CH_2)_m$—$NR^{10}$,
5) a 6- to 44-membered aryl, wherein aryl is unsubstituted or mono-, di- or trisubstituted independently of one another by R14, 6) a monocyclic or bicyclic 4- to 15-membered heterocyclyl, wherein heterocyclyl is unsubstituted or mono-, di- or trisubstituted independently of one another by R14,
7) —(C$_3$-C$_8$)-cycloalkyl, wherein said cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, R3, R4 and R22 are independent of one another are identical or different and are
1) hydrogen atom,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
   a) hydrogen atom,
   b) —(C$_1$-C$_4$)-alkyl, wherein alkyl is unsubstituted or mono-, di- or trisubstituted independently of one another by R13, or
   c) phenyl, wherein phenyl is unsubstituted or mono-, di- or trisubstituted independently of one another by R13,
   d) —CF$_3$, or
   e) —CHF$_2$,
7) —NO$_2$,
8) —CN,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —NR$^{10}$—SO$_2$—R$^{10}$,
16) —S—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)-O—C(O)—R17,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R15, R16)-O—C(O)—O—R17,
21) —(C$_0$-C$_4$)-alkylene-(C$_6$-C$_{14}$)-aryl, wherein aryl is mono-, di- or trisubstituted independently of one another by R13,
22) —(C$_0$-C$_4$)-alkylene-(C$_4$-C$_{15}$)-heterocyclyl, wherein heterocyclyl is unsubstituted or mono-, di- or trisubstituted independently of one another by R13
23) —(C$_0$-C$_4$)-alkylene-(C$_3$-C$_8$)-cycloalkyl, wherein cycloalkyl is unsubstituted or mono-, di- or trisubstituted independently of one another by R13,
24) —(C$_0$-C$_4$)-alkylene-het, wherein het is unsubstituted or mono-, di- or trisubstituted independently of one another by R13,
25) —(C$_0$-C$_4$)-alkylene-O—CH$_2$—(C$_1$-C$_3$)-perfluoroalkylene-CH$_2$—O—(C$_0$-C$_4$)-alkyl,
26) —SO$_w$—N(R$^{11}$)—R$^{13}$, wherein w is 1 or 2,
27) —(C$_0$-C$_4$)-alkylene-C(O)—N(R$^{11}$)—R13,
28) —(C$_0$-C$_4$)-alkylene-N(R$^{11}$)—R$^{13}$, or
29) a residue from the following list

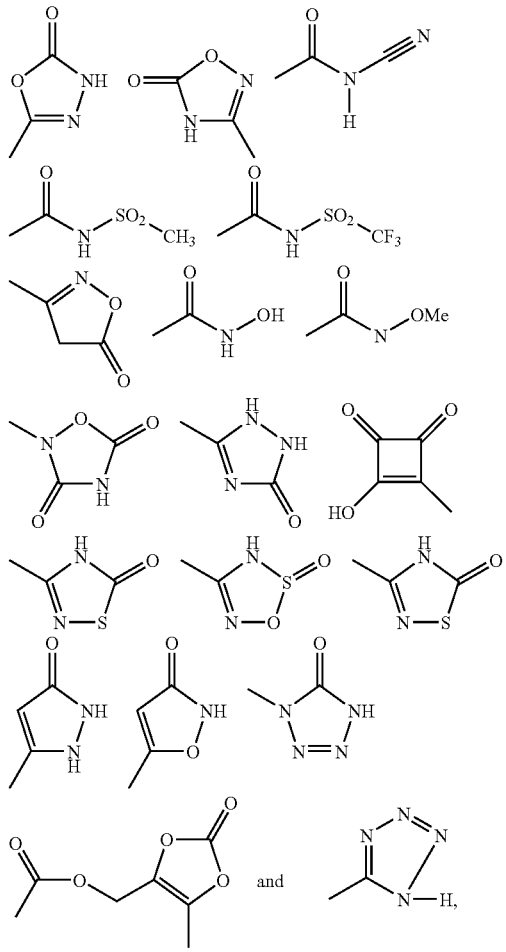

wherein Me is methyl, or
   if two —OR19 residues are attached to adjacent atoms they can form together with the atoms which they are attached to a 5- or 6-membered ring, which is unsubstituted or substituted one, two, three or four times by R13,
R11 and R$^{12}$ are independently of one another identical or different and are
   1) hydrogen atom,
   2) —(C$_1$-C$_6$)-alkyl, wherein alkyl is unsubstituted or mono-, di- or trisubstituted independently of one another by R13,
   3) —(C$_0$-C$_6$)-alkyl-(C$_3$-C$_8$)-cycloalkyl,
   4) —SO$_t$—R$^{10}$, wherein t is 1 or 2,
   5) —(C$_0$-C$_6$)-alkyl-(C$_6$-C$_{14}$)-aryl, wherein alkyl and aryl independently from one another are unsubstituted or mono-, di- or trisubstituted by R13,
   6) —(C$_1$-C$_3$)-perfluoroalkyl,
   7) —O—R$^{17}$, or
   8) —(C$_0$-C$_6$)-alkyl-(C$_4$-C$_{15}$)-heterocyclyl, wherein alkyl and heterocyclyl independently from one another are unsubstituted or mono-, di- or trisubstituted by R13, or
R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R4 and R22 in formula I or formula Ia together with the carbon atoms to which they are each bonded can form a phenyl residue, R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R15, R16)—O—C(O)—R17, —(C$_1$-C$_4$)-alkoxy-phenyl, —(C$_0$-C$_4$)-alkyl-C(O)—O—C(R15, R16)—O—C(O)—O—R17, —(C$_1$-C$_3$)-perfluoroalkyl, —O—R15, —NH—C(O)—NH—R$^{10}$, —NH—C(O)—O—R$^{10}$, or a residue from the following list

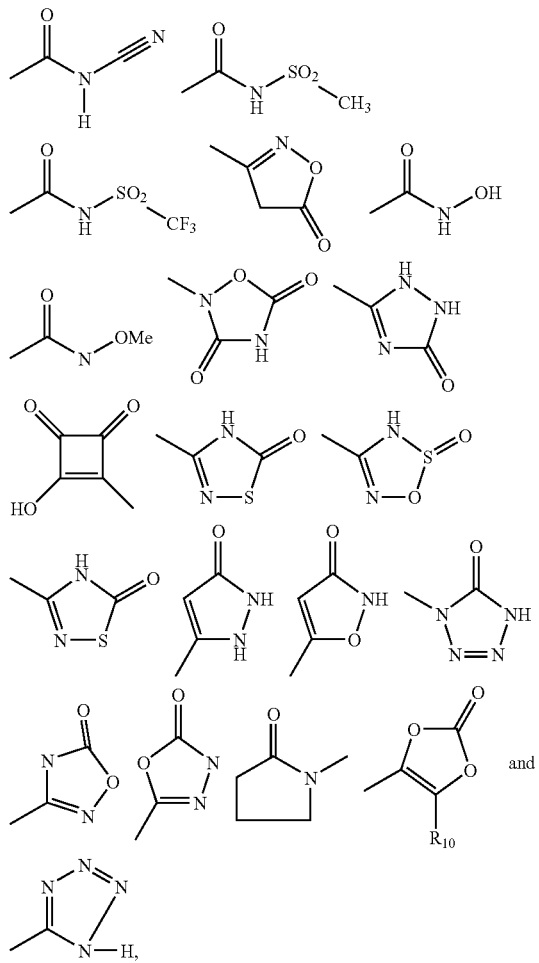

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-alkyl or —(C$_1$-C$_3$)-perfluoroalkyl, R15 and R16 are independently of one another hydrogen, —(C$_1$-C$_6$)-alkyl, or together with the carbon atom to which they are bonded they can form a 3- to 6 membered carbocyclic ring which is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

DETAILED DESCRIPTION OF THE INVENTION

2) The present invention also relates to compounds of the formula I, wherein

R$^0$ is 1) a monocyclic or bicyclic 6- to 14-membered aryl, wherein aryl is mono-, di- or trisubstituted independently of one another by R8, 2) a monocyclic or bicyclic 4- to 15-membered heterocyclyl out of the group benzothiophen, indazolyl, indolyl, isoindolyl, isoquinolyl, phenylpyridyl, phthalazinyl, pyridyl, pyridinyl, pyrimidinyl, quinazolinyl and quinolyl, wherein said heterocyclyl is unsubstituted or mono-, di- or trisubstituted independently of one another by R8, or 3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is 1) halogen,
2) —NO$_2$,
3) —OH,
4) —O—CF$_3$
5) a monocyclic or bicyclic 6- to 14-membered aryl, wherein aryl is mono-, di- or trisubstituted independently of one another by halogen or —O—(C$_1$-C$_8$)-alkyl,
6) —(C$_1$-C$_8$)-alkyl, wherein alkyl is unsubstituted or mono-, di- or trisubstituted independently of one another by halogen, —OH or a methoxy residue,
7) —O—(C$_1$-C$_8$)-alkyl, wherein alkyl is unsubstituted or mono-, di- or trisubstituted independently of one another by halogen, NH$_2$, —OH or a methoxy residue,
8) —SO$_2$—CH$_3$ or
9) —SO$_2$—CF$_3$, provided that R8 is at least one halogen or —O—(C$_1$-C$_8$)-alkyl residue, if R$^0$ is a monocyclic or bicyclic 6- to 14-membered aryl, Q is —(C$_0$-C$_2$)-alkylene-C(O)—NR$^{10}$—, —NR$^{10}$—C(O)—NR$^{10}$—, —NR$^{10}$C(O)—, —(C$_1$-C$_6$)-alkylene, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —(CH$_2$)$_m$—S—(CH$_2$)$_n$—, —(CH$_2$)$_m$—C(O)—(CH$_2$)$_n$—, —(CH$_2$)$_m$—SO$_2$—NR$^{10}$—(CH$_2$)$_n$—, —(CH$_2$)$_m$—NR$^{10}$—SO$_2$—(CH$_2$)$_n$—, —(CH$_2$)$_m$—NR$^{10}$—SO$_2$—NR$^{10}$—(CH$_2$)$_n$—, —(CH$_2$)$_m$—CH(OH)—(CH$_2$)$_n$—, —(CH$_2$)$_m$—O—C(O)—NR$^{10}$—(CH$_2$)$_n$—, —(C$_2$-C$_3$)-alkylene-O—(C$_0$-C$_3$)-alkylene-, —(C$_2$-C$_3$)-alkylene-S(O)—, —(C$_2$-C$_3$)-alkylene-S(O)$_2$—, —(CH$_2$)$_m$—NR$^{10}$—C(O)—O—(CH$_2$)$_n$—, —$(C_2$-$C_3)$-alkylene-S(O)$_2$—NH—$(R^{10})$—, —$(C_2$-$C_3)$-alkylene-N$(R^{10})$— or —$(C_0$-$C_3)$-alkylene-C(O)—O—$(CH_2)_m$—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —NH$_2$ or —OH; or —$(C_3$-$C_6)$-cycloalkylen, wherein cycloalkylen is unsubstituted or mono-, di- or trisubstituted independently of one another by halogen, —NH$_2$ or —OH;

$R^1$ is a hydrogen atom, —$(C_1$-$C_4)$-alkyl, wherein alkyl is unsubstituted or substituted one to three times by R13; —$(C_1$-$C_3)$-alkylene-C(O)—NH—$R^0$; —$(C_1$-$C_3)$-alkylene-C(O)—O—R15; a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —$(C_1$-$C_3)$-perfluoroalkylene; —$(C_1$-$C_3)$-alkylene-S(O)—$(C_1$-$C_4)$-alkyl; —$(C_1$-$C_3)$-alkylene-S(O)$_2$—$(C_1$-$C_3)$-alkyl; —$(C_1$-$C_3)$-alkylene-S(O)$_2$—N(R4')—$R^{5'}$; —$(C_1$-$C_3)$-alkylene-O—$(C_1$-$C_4)$-alkyl; —$(C_0$-$C_3)$-alkylene-$(C_3$-$C_8)$-cycloalkyl or —$(C_0$-$C_3)$-alkylene-het, wherein het is unsubstituted or mono-, di- or trisubstituted independently of one another by R14, $R^{4'}$ and $R^{5'}$ are independent of one another are identical or different and are hydrogen atom or —$(C_1$-$C_4)$-alkyl, or $R^1$ and R22 together with the atoms to which they are bonded can form a 6- to 8-membered cyclic group, containing up to 1, 2, 3 or 4 heteroatoms chosen from nitrogen, sulfur or oxygen, wherein said cyclic group is unsubstituted or mono-, di- or trisubstituted independently of one another by R14, or $R^1$—N—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —$(C_1$-$C_8)$-alkyl, —$(C_1$-$C_4)$-alkoxy, —NO$_2$, —$(C_0$-$C_4)$-alkyl-C(O)—O—$R^{18}$, —CN, —$(C_0$-$C_4)$-alkyl-N$(R^{18})$—$R^{21}$, —$(C_0$-$C_4)$-alkyl-O—$R^{18}$, —$(C_0$-$C_4)$-alkyl-het, —$(C_0$-$C_8)$-alkyl-SO$_2$—$(C_1$-$C_4)$-alkyl, —$(C_0$-$C_8)$-alkyl-SO$_2$—$(C_1$-$C_3)$-perfluoroalkyl, —$(C_0$-$C_8)$-alkyl-SO$_2$—N$(R^{18})$—$R^{21}$, —C(O)—NH—$(C_1$-$C_8)$-alkyl, —C(O)—N—[$(C_1$-$C_8)$-alkyl]$_2$, —$NR^{18}$—C(O)—NH—$(C_1$-$C_8)$-alkyl, —C(O)—NH$_2$, —S—$R^{18}$, or —$NR^{18}$—C(O)—NH—[$(C_1$-$C_8)$-alkyl]$_2$, wherein $R^{18}$ and $R^{21}$ are independently from each other hydrogen atom, —$(C_1$-$C_3)$-perfluoroalkyl or —$(C_1$-$C_6)$-alkyl, V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, or 2) a monocyclic or bicyclic 4- to 15-membered heterocyclyl, wherein said heterocyclyl is unsubstituted or mono-, di- or trisubstituted independently of one another by R14, G is a direct bond, —$(CH_2)_m$—$NR^{10}$—SO$_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)_m$—SO$_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—SO$_2$—$NR^{10}$—$(CH_2)_n$—, —$(CH_2)_m$—$NR^{10}$—SO$_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—, n and m are independently of one another identical or different and are the integers zero, 1, 2, 3, 4, 5 or 6, M is 1) a hydrogen atom,
2) —$(C_1$-$C_8)$-alkyl, wherein alkyl is unsubstituted or mono-, di- or trisubstituted independently of one another by R14,
3) —C(O)—N$(R^{11})$—R12,
4) —$(CH_2)_m$—$NR^{10}$,
5) —$(C_6$-$C_{14})$-aryl, wherein aryl is unsubstituted or mono-, di- or trisubstituted independently of one another by R14,
6) —$(C_4$-$C_{15})$-heterocyclyl, wherein heterocyclyl is unsubstituted or mono-, di- or trisubstituted independently of one another by R14,
7) —$(C_3$-$C_8)$-cycloalkyl, wherein said cycloalkyl is unsubstituted or mono-, di- or trisubstituted independently of one another by R14, or
8) a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, R3, R4 and R22 are independent of one another are identical or different and are
1) hydrogen atom,
2) halogen,
3) —$(C_1$-$C_4)$-alkyl, wherein alkyl is unsubstituted or mono-, di- or trisubstituted independently of one another by R13,
4) —$(C_1$-$C_3)$-perfluoroalkyl,
5) phenyl, wherein phenyl is unsubstituted or mono-, di- or trisubstituted independently of one another by R13,
6) —$(C_0$-$C_4)$-alkylene-O—R19, wherein R19 is
   a) hydrogen atom,
   b) —$(C_1$-$C_4)$-alkyl, wherein alkyl is unsubstituted or mono-, di- or trisubstituted independently of one another by R13, or
   c) phenyl, wherein phenyl is unsubstituted or mono-, di- or trisubstituted independently of one another by R13,
   d) —CF$_3$,
   e) —CHF$_2$,
7) —NO$_2$,
8) —CN,
9) —SO$_s$—$R^{11}$, wherein s is 1 or 2,
10) —SO$_t$—N$(R^{11})$—R12, wherein t is 1 or 2,
11) —$(C_0$-$C_4)$-alkylene-C(O)—$R^{11}$,
12) —$(C_0$-$C_4)$-alkylene-C(O)—O—$R^{11}$,
13) —$(C_0$-$C_4)$-alkylene-C(O)—N$(R^{11})$—$R^{12}$,
14) —$(C_0$-$C_4)$-alkylene-N$(R^{11})$—$R^{12}$,
15) —$NR^{10}$—SO$_2$—$R^{10}$,
16) —S—$R^{10}$,
17) —$(C_0$-$C_2)$alkylene-C(O)—O—$(C_{2-4})$-alkylene-O—C(O)—$(C_1$-$C_4)$-alkyl,
18) —C(O)—O—C(R15, R16)—O—C(O)—R17,
19) —$(C_0$-$C_2)$alkylene-C(O)—O—$(C_2$-$C_4)$-alkylene-O—C(O)—O—$(C_1$-$C_6)$-alkyl,
20) —C(O)—O—C(R15, R16)—O—C(O)—O—R17,
21) —$(C_0$-$C_4)$-alkylene-$(C_6$-$C_{14})$-aryl, wherein aryl is mono-, di- or trisubstituted independently of one another by R13,
22) —$(C_0$-$C_4)$-alkylene-$(C_4$-$C_{15})$-heterocyclyl, wherein heterocyclyl is unsubstituted or mono-, di- or trisubstituted independently of one another by R13

23) —$(C_0\text{-}C_4)$-alkylene-$(C_3\text{-}C_8)$-cycloalkyl, wherein cycloalkyl is unsubstituted or mono-, di- or trisubstituted independently of one another by R13,
24) —$(C_0\text{-}C_4)$-alkylene-het, wherein het is unsubstituted or mono-, di- or trisubstituted independently of one another by R13,
25) —$(C_0\text{-}C_3)$-alkylene-O—$CH_2$—$(C_1\text{-}C_3)$-perfluoroalkylene-$CH_2$—O—$(C_0\text{-}C_3)$-alkyl, or
26) —$SO_w$—$N(R^{11})$—$R^{13}$, wherein w is 1 or 2,
27) —$(C_0\text{-}C_4)$-alkylene-C(O)—$N(R^{11})$—$R^{13}$,
28) —$(C_0\text{-}C_4)$-alkylene-$N(R^{11})$—$R^{13}$, or
29) a residue from the following list

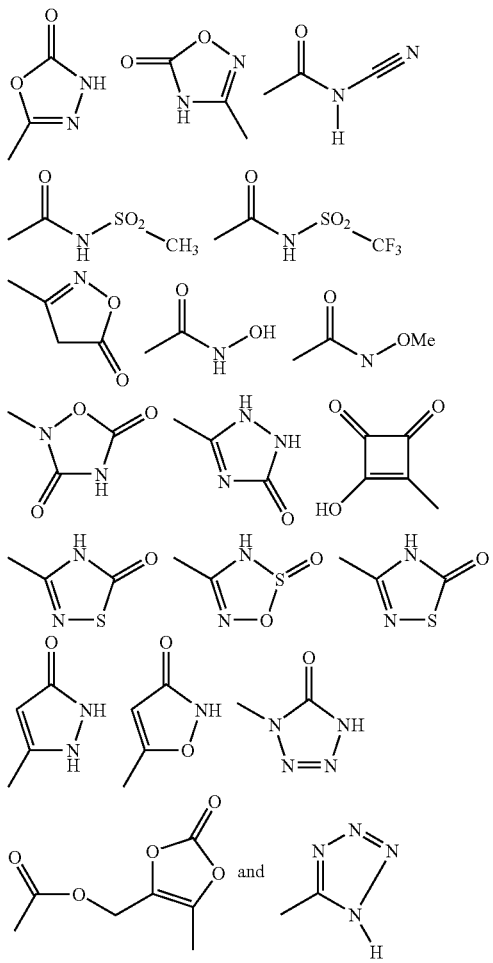

wherein Me is methyl, or
if two —OR19 residues are attached to adjacent atoms they can form together with the atoms which they are attached to a 5- or 6-membered ring, which is unsubstituted or substituted one, two, three or four times by R13, R11 and R12 are independently of one another identical or different and are
1) hydrogen atom,
2) —$(C_1\text{-}C_6)$-alkyl, wherein alkyl is unsubstituted or mono-, di- or trisubstituted independently of one another by R13,
3) —$(C_0\text{-}C_6)$-alkyl-$(C_3\text{-}C_8)$-cycloalkyl,
4) —$SO_t$—$R^{10}$, wherein t is 1 or 2,
5) —$(C_0\text{-}C_6)$-alkyl-$(C_6\text{-}C_{14})$-aryl, wherein alkyl and aryl independently from one another are unsubstituted or mono-, di- or trisubstituted by R13, 6) —$(C_1\text{-}C_3)$-perfluoroalkyl,
7) —O—$R^{17}$, or
8) —$(C_0\text{-}C_6)$-alkyl-$(C_4\text{-}C_{15})$-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R4 and R22 in formula I or formula Ia together with the carbon atoms to which they are each bonded can form a phenyl residue, R13 is halogen, —$NO_2$, —CN, =O, —OH, —$CF_3$, —C(O)—O—$R^{10}$, —C(O)—$N(R^{10})$—$R^{20}$, —$N(R^{10})$—$R^{20}$, —$(C_3\text{-}C_8)$-cycloalkyl, —$(C_0\text{-}C_3)$-alkylene-O—$R^{10}$, —$Si\text{-}(CH_3)_3$, —$N(R^{10})$—$S(O)_u$—$R^{10}$, wherein u is 1 or 2, S—$R^{10}$, —$SO_r$—$R^{10}$, wherein r is 1 or 2, —$S(O)_v$—N$(R^{10})$—$R^{20}$, wherein v is 1 or 2, —C(O)—$R^{10}$, —$(C_1\text{-}C_8)$-alkyl, —$(C_1\text{-}C_8)$-alkoxy, phenyl, phenyloxy-, —O—$CF_3$, —$(C_0\text{-}C_4)$-alkyl-C(O)—O—C(R15, R16)—O—C(O)—R17, —$(C_1\text{-}C_4)$-alkoxy-phenyl, —$(C_0\text{-}C_4)$-alkyl-C(O)—O—C(R15, R16)—O—C(O)—O—R17, —$(C_1\text{-}C_3)$-perfluoroalkyl, —O—R15; —NH—$R^{10}$, —NH—C(O)—O—$R^{10}$, or a residue from the following list

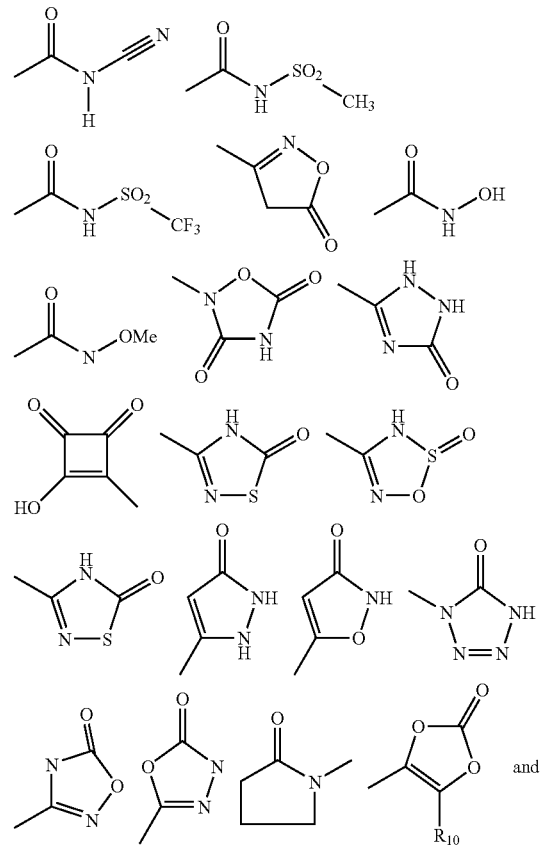

-continued

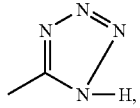

$R^{10}$ and $R^{20}$ are independently of one another hydrogen, —$(C_1$-$C_6)$-alkyl or —$(C_1$-$C_3)$-perfluoroalkyl, R15 and R16 are independently of one another hydrogen, —$(C_1$-$C_6)$-alkyl, or together with the carbon atom to which they are bonded they can form a 3- to 6 membered carbocyclic ring which is unsubstituted or substituted one to three times by $R^{10}$, and R17 is —$(C_1$-$C_6)$-alkyl, —$(C_1$-$C_6)$-alkyl-OH, —$(C_1$-$C_6)$-alkyl-O—$(C_1$-$C_6)$-alkyl, —$(C_3$-$C_8)$-cycloalkyl, —$(C_1$-$C_6)$-alkyl-O—$(C_1$-$C_8)$-alkyl-$(C_3$-$C_8)$-cycloalkyl, —$(C_1$-$C_6)$-alkyl-$(C_3$-$C_8)$-cycloalkyl, wherein said cycloalkyl ring is unsubstituted or substituted one, two or three times by —OH, —O—$(C_1$-$C_4)$-alkyl or $R^{10}$, in all its stereoisomeric forms and mixtures thereof in any ratio, and its physiologically tolerable salts 3) Thus, the present invention relates to compounds of the formula I, wherein $R^0$ is 1) a monocyclic or bicyclic 6- to 14-membered aryl out of the group phenyl, naphthyl, biphenylyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridinyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl, wherein heterocyclyl is selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R8, and which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1) halogen,
  2) —$NO_2$,
  3) —OH,
  4) —O—$CF_3$ 5) a monocyclic or bicyclic 6- to 14-membered aryl, wherein aryl is mono-, di- or trisubstituted independently of one another by halogen or —O—($C_1$-$C_8$)-alkyl,
6) —($C_1$-$C_8$)-alkyl, wherein alkyl is unsubstituted or mono-, di- or trisubstituted independently of one another by halogen, —OH or a methoxy residue,
7) —O—($C_1$-$C_8$)-alkyl, wherein alkyl is unsubstituted or mono-, di- or trisubstituted independently of one another by halogen, $NH_2$, —OH or a methoxy residue,
8) —$SO_2$—$CH_3$ or
9) —$SO_2$—$CF_3$, provided that R8 is at least one halogen or —O—($C_1$-$C_8$)-alkyl residue, if $R^0$ is a monocyclic or bicyclic 6- to 14-membered aryl, Q is —($C_0$-$C_2$)-alkylene-C(O)—$NR^{10}$—, —$NR^{10}$—C(O)—$NR^{10}$—, —$NR^{10}$—C(O)—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or —($C_0$-$C_3$)-alkylene-C(O)—O—$(CH_2)_m$—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —($C_3$-$C_6$)-cycloalkylen, wherein cycloalkylen is unsubstituted or mono-, di- or trisubstituted independently of one another by halogen, —$NH_2$ or —OH;

$R^1$ is a hydrogen atom, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—R15, an aryl residue out of the group phenyl, naphthyl, biphenylyl, anthryl or fluorenyl, wherein aryl is mono-, di- or trisubstituted independently of one another by R8, wherein R8 is as defined above;
a monocyclic or bicyclic 4- to 15-membered heterocyclyl, which is as defined above; —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a residue selected out of the group azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxathiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan,
thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen atom or —($C_1$-$C_4$)-alkyl, or $R^1$ and R22 together with the atoms to which they are bonded can form a 6- to 8-membered cyclic residue selected out of the group azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, [oxocane, oxocan-2-one, piperazine, piperidine, pyran, pyrazine, pyridazine, pyrimidine or 5,6,7,8-tetrahydro-1H-azocin-2-one, wherein said cyclic group is unsubstituted or mono-, di- or trisubstituted independently of one another by R14, or $R^1$—N—V can form a 4- to 8-membered cyclic group selected out of the group azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is halogen, —OH, =O, —($C_1$-$C_8$)-alkyl, —($C_1$-$C_4$)-alkoxy, —$NO_2$, —($C_0$-$C_4$)-alkyl-C(O)—O—$R^{18}$, —CN, —($C_0$-$C_4$)-alkyl-N($R^{18}$)—$R^{21}$, —($C_0$-$C_4$)-alkyl-O—$R^{18}$, —($C_0$-$C_4$)-alkyl-het, wherein het is a residue selected from azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazapane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$, wherein $R^{18}$ and $R^{21}$ are independently from each other hydrogen atom, —($C_1$-$C_3$)-perfluoroalkyl or —($C_1$-$C_6$)-alkyl, V is a heterocyclyl out of the group acridinyl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R14, G is a direct bond, $-(CH_2)_m-NR^{10}-SO_2-NR^{10}-(CH_2)_n-$, $-(CH_2)_m-CH(OH)-(CH_2)_n-$, $-(CH_2)_m-$, $-(CH_2)_m-O-(CH_2)_n-$, $-(CH_2)_m-C(O)-NR^{10}-(CH_2)_n-$, $-(CH_2)-SO_2-(CH_2)_n-$, $-(CH_2)_m-NR^{10}-C(O)-NR^{10}-(CH_2)_n-$, $-(CH_2)_m-NR^{10}-C(O)-(CH_2)_n-$, $-(CH_2)_m-C(O)-(CH_2)_n-$, $-(CH_2)-S-(CH_2)_n-$, $-(CH_2)_m-SO_2-NR^{10}-(CH_2)_n-$, $-(CH_2)_m-NR^{10}-SO_2-(CH_2)_n-$, $-(CH_2)_m-NR^{10}-$, $-(CH_2)_m-O-C(O)-NR^{10}-(CH_2)_n-$ or $-(CH_2)_m-NR^{10}-C(O)-O-(CH_2)_n-$, n and m are independently of one another identical or different and are the integers zero, 1, 2, 3, 4, 5 or 6, M is 1) a hydrogen atom,
2) $-(C_1-C_8)$-alkyl, wherein alkyl is unsubstituted or mono-, di- or trisubstituted independently of one another by R14,
3) $-C(O)-N(R11)-R12$,
4) $-(CH_2)_m-NR^{10}$,
5) $-(C_6-C_{14})$-aryl, wherein aryl is as defined above and wherein aryl is unsubstituted or mono-, di- or trisubstituted independently of one another by R14,
6) $-(C_4-C_{15})$-heterocyclyl, wherein heterocyclyl is as defined above and is unsubstituted or mono-, di- or trisubstituted independently of one another by R14, or
7) $-(C_3-C_8)$-cycloalkyl, wherein said cycloalkyl is unsubstituted or mono-, di- or trisubstituted independently of one another by R14, R3, R4 and R22 are independent of one another are identical or different and are
1) hydrogen atom,
2) halogen,
3) $-(C_1-C_4)$-alkyl, wherein alkyl is unsubstituted or mono-, di- or trisubstituted independently of one another by R13,
4) $-(C_1-C_3)$-perfluoroalkyl,
5) phenyl, wherein phenyl is unsubstituted or mono-, di- or trisubstituted independently of one another by R13,
6) $-(C_0-C_4)$-alkylene-O$-$R19, wherein R19 is
  a) hydrogen atom,
  b) $-(C_1-C_4)$-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) $-CF_3$,
  e) $-CHF_2$,
7) $-NO_2$,
8) $-CN$,
9) $-SO_s-R^{11}$, wherein s is 1 or 2,
10) $-SO_t-N(R^{11})-R^{12}$, wherein t is 1 or 2,
11) $-(C_0-C_4)$-alkylene-C(O)$-R^{11}$,
12) $-(C_0-C_4)$-alkylene-C(O)$-O-R^{11}$,
13) $-(C_0-C_4)$-alkylene-C(O)$-N(R^{11})-R^{12}$,
14) $-(C_0-C_4)$-alkylene-N(R^{11})-R^{12}$,
15) $-NR^{10}-SO_2-R^{10}$,
16) $-S-R^{10}$,
17) $-(C_0-C_2)$alkylene-C(O)$-O-(C_{2-4})$-alkylene-O$-C(O)-(C_1-C_4)$-alkyl,
18) $-C(O)-O-C(R15, R16)-O-C(O)-R17$,
19) $-(C_0-C_2)$alkylene-C(O)$-O-(C_2-C_4)$-alkylene-O$-C(O)-O-(C_1-C_6)$-alkyl,
20) $-C(O)-O-C(R15, R16)-O-C(O)-O-R17$,
21) $-(C_0-C_4)$-alkylene-$(C_6-C_{14})$-aryl, wherein aryl is mono-, di- or trisubstituted independently of one another by R13,
22) $-(C_0-C_4)$-alkylene-$(C_4-C_{15})$-heterocyclyl, wherein heterocyclyl is unsubstituted or mono-, di- or trisubstituted independently of one another by R13
23) $-(C_0-C_4)$-alkylene-$(C_3-C_8)$-cycloalkyl, wherein cycloalkyl is unsubstituted or mono-, di- or trisubstituted independently of one another by R13,
24) $-(C_0-C_4)$-alkylene-het, wherein het is unsubstituted or mono-, di- or trisubstituted independently of one another by R13,
25) $-(C_0-C_3)$-alkylene-O$-CH_2-(C_1-C_3)$-perfluoroalkylene-$CH_2-O-(C_0-C_3)$-alkyl, or
26) $-SO_w-N(R^{11})-R13$, wherein w is 1 or 2,
27) $-(C_0-C_4)$-alkylene-C(O)$-N(R^{11})-R13$,
28) $-(C_0-C_4)$-alkylene-N(R^{11})-R13$, or
29) a residue from the following list

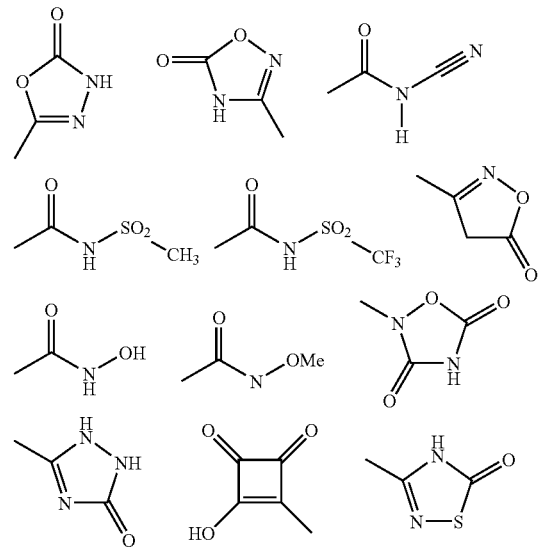

-continued

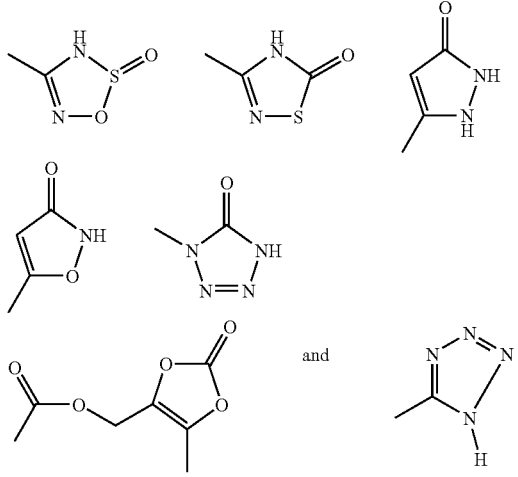

wherein Me is methyl, or
if two —OR19 residues are attached to adjacent atoms they can form together with the atoms which they are attached to a 1,3-dioxole ring or a 2,3-dihydro-[1,4] dioxine ring, which is substituted one, two, three or four times by R13, R11 and R12 are independently of one another identical or different and are
1) hydrogen atom,
2) —($C_1$-$C_6$)-alkyl, wherein alkyl is unsubstituted or mono-, di- or trisubstituted independently of one another by R13,
3) —($C_0$-$C_6$)-alkyl-($C_3$-$C_8$)-cycloalkyl,
4) —$SO_t$—$R^{10}$, wherein t is 1 or 2,
5) —($C_0$-$C_6$)-alkyl-($C_6$-$C_{14}$)-aryl, wherein alkyl and aryl independently from one another are unsubstituted or mono-, di- or trisubstituted by R13,
6) —($C_1$-$C_3$)-perfluoroalkyl,
7) —O—R17, or
8) —($C_0$-$C_6$)-alkyl-($C_4$-$C_{15}$)-heterocyclyl, wherein alkyl and heterocyclyl are as defined above and are independently from one another unsubstituted or mono-, di- or trisubstituted by R13, or R11 and R12 together with the nitrogen atom to which they are bonded form a heterocyclic ring out of the group azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, 1,4-oxazepinyl, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R13, R4 and R22 in formula I or formula Ia together with the carbon atoms to which they are each bonded can form a phenyl residue, R13 is halogen, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_3$-$C_8$)-cycloalkyl, —($C_0$-$C_3$)-alkylene-O—$R^{10}$, —Si—($CH_3$)$_3$, —N($R^{10}$)—S(O)$_u$—$R^{10}$, wherein u is 1 or 2, —S—$R^{10}$, —$SO_r$—$R^{10}$, wherein r is 1 or 2, —S(O)$_v$—N($R^{10}$)—$R^{20}$, wherein v is 1 or 2, —C(O)—$R^{10}$, —($C_1$-$C_8$)-alkyl, —($C_1$-$C_8$)-alkoxy, phenyl, phenyloxy-, —O—$CF_3$, —($C_0$-$C_4$)-alkyl-C(O)—O—C(R15, R16)—O—C(O)—R17, —($C_0$-$C_4$)-alkoxy-phenyl, —($C_0$-$C_4$)-alkyl-C(O)—O—C(R15, R16)—O—C(O)—O—$R^7$, —($C_1$-$C_3$)-perfluoroalkyl, —O—R15, —NH—C(O)—NH—$R^{10}$, —NH—C(O)—O—$R^{10}$ or a residue from the following list

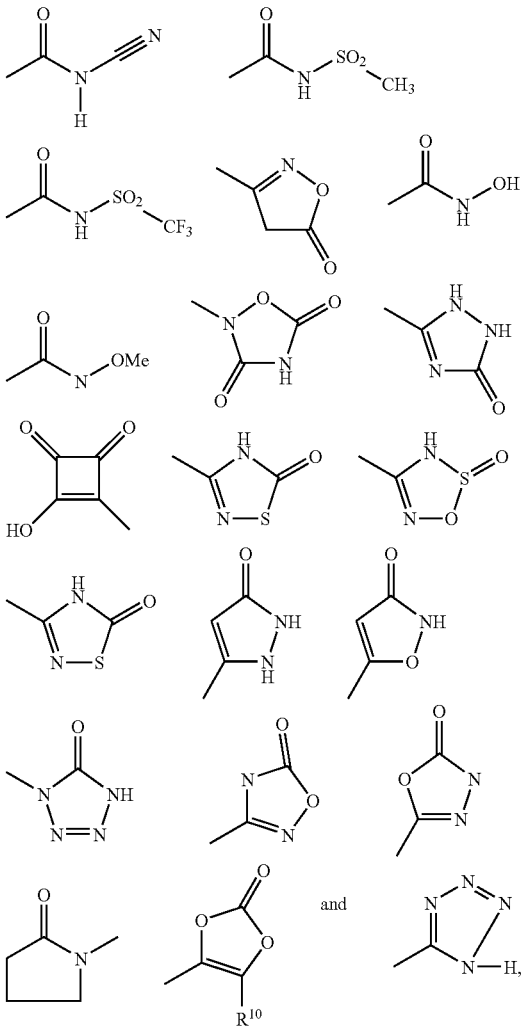

wherein Me is methyl,
$R^{10}$ and $R^{20}$ are independently of one another hydrogen, —($C_1$-$C_6$)-alkyl, —($C_0$-$C_4$)-alkyl-OH, —($C_0$-$C_4$)-alkyl-O—($C_1$-$C_4$)-alkyl or —($C_1$-$C_3$)-perfluoroalkyl,
R15 and R16 are independently of one another hydrogen, —($C_1$-$C_6$)-alkyl, cyclopropyl, cyclobutyl, cyclopentyl or cyclohexyl, wherein each ring is unsubstituted or substituted one to three times by $R^{10}$, and
R17 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts 4) The present invention also relates to the compounds of the formula I, wherein $R^0$ is 1) a monocyclic or bicyclic 6- to 14-membered aryl out of the group phenyl, naphthyl, biphenyl, anthryl or fluorenyl, wherein aryl is mono-, di- or trisubstituted independently of one another by R8,
  2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridinyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
  3) a heterocyclyl out of the group azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl or 3-thienyl, which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl,
  wherein heterocyclyl is unsubstituted or mono-, di- or trisubstituted independently of one another by R8, R8 is 1) fluorine, chlorine or bromine,
  2) —$NO_2$,
  3) —OH,
  4) —O—$CF_3$
  5) a monocyclic or bicyclic 6- to 14-membered aryl, wherein aryl is mono-, di- or trisubstituted independently of one another by halogen or —O—($C_1$-$C_8$)-alkyl,
  6) —($C_1$-$C_8$)-alkyl, wherein alkyl is unsubstituted or mono-, di- or trisubstituted independently of one another by halogen, —OH or a methoxy residue,
  7) —O—($C_1$-$C_8$)-alkyl, wherein alkyl is unsubstituted or mono-, di- or trisubstituted independently of one another by halogen, $NH_2$, —OH or a methoxy residue,
  8) —$SO_2$—$CH_3$ or
  9) —$SO_2$—$CF_3$,
  provided that R8 is at least one halogen or —O—($C_1$-$C_8$)-alkyl residue, if $R^0$ is an aryl or a heterocyclyl, which are as defined above, Q is —($C_0$-$C_2$)-alkylene-C(O)—$NR^1$—, —$NR^{10}$—C(O)—$NR^{10}$—, —$NR^{10}$—C(O)—, —($C_1$-$C_6$)-alkylene, —($C_0$-$C_3$)-alkylene-C(O)—O—($C_0$-$C_2$)-alkylene, $R^1$ is a hydrogen atom, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—R15, —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^5$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a residue selected out of the group azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen atom or —($C_1$-$C_4$)-alkyl, or $R^1$—N—V form a 4- to 8-membered cyclic group selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =o, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —($C_0$-$C_4$)-alkyl-$SO_2$—($C_1$-$C_4$)-alkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$,
  wherein $R^{18}$ and $R^{21}$ are independently from each other hydrogen atom, —($C_1$-$C_3$)-perfluoroalkyl or —($C_1$-$C_6$)-alkyl, V is a heterocyclyl residue out of the group azaindole (1H-pyrrolopyridine), azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, which is as defined above and wherein het is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—,
  n and m are independently of one another identical or different and are the integers zero, 1, 2, 3, 4, 5 or 6, M is 1) a hydrogen atom,
  2) —($C_1$-$C_8$)-alkyl, wherein alkyl is unsubstituted or mono-, di- or trisubstituted independently of one another by R14,
  3) —C(O)—N(R11)—R12,
  4) —$(CH_2)_m$—$NR^{10}$,
  5) phenyl or naphthyl, wherein phenyl or naphthyl are unsubstituted or mono-, di- or trisubstituted independently of one another by R14,
  6) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiophene, thiomorpholine, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, or
  7) —($C_3$-$C_8$)-cycloalkyl, wherein said cycloalkyl is unsubstituted or mono-, di- or trisubstituted independently of one another by R14, R3, R4 and R22 are independent of one another are identical or different and are
  1) hydrogen atom,
  2) halogen,
  3) —($C_1$-$C_4$)-alkyl, wherein alkyl is unsubstituted or mono-, di- or trisubstituted independently of one another by R13,
  4) —($C_1$-$C_3$)-perfluoroalkyl,
  5) phenyl, wherein phenyl is unsubstituted or mono-, di- or trisubstituted independently of one another by R13,
  6) ($C_0$-$C_4$) alkylene-O—R19, wherein R19 is
    a) hydrogen atom,
    b) —($C_1$-$C_4$)-alkyl, wherein alkyl is unsubstituted or mono-, di- or trisubstituted independently of one another by R13, or
    c) phenyl, wherein phenyl is unsubstituted or mono-, di- or trisubstituted independently of one another by R13,
    d) —$CF_3$, or
    e) $CHF_2$,
  7) —CN,
  8) —($C_0$-$C_4$)-alkylene-($C_4$-$C_{15}$)-heterocyclyl, wherein heterocyclyl is a defined above and is unsubstituted or mono-, di- or trisubstituted independently of one another by R13,
  9) —$SO_s$—$R^{11}$, where s is 1 or 2,
  10) —$SO_t$—N($R^{11}$)—$R^{12}$, wherein t is 1 or 2,
  11) —($C_0$-$C_4$)-alkylene-C(O)—$R^{11}$,
  12) —($C_0$-$C_4$)-alkylene-C(O)—O—$R^{11}$,
  13) —($C_0$-$C_4$)-alkylene-C(O)—N($R^{11}$)—$R^{12}$,
  14) —($C_0$-$C_4$)-alkylene-N($R^{11}$)—$R^{12}$,
  15) —$NR^{10}$—$SO_2$—$R^{10}$,
  16) —($C_0$-$C_4$)-alkylene-het, wherein het is as defined above and is unsubstituted or mono-, di- or trisubstituted independently of one another by R13,
  17) —($C_0$-$C_2$)alkylene-C(O)—O—($C_2$-$C_4$)-alkylene-O—C(O)—($C_1$-$C_4$)-alkyl,
  18) —C(O)—O—C(R15,R16)-O—C(O)—R17,
  19) —($C_0$-$C_2$)alkylene-C(O)—O—($C_2$-$C_4$)-alkylene-O—C(O)—O—($C_1$-$C_6$)-alkyl,
  20) —C(O)—O—C(R15, R16)-O—C(O)—O—R17,
  21) —($C_0$-$C_4$)-alkylene-($C_6$-$C_{14}$)-aryl, wherein aryl is a defined above and is mono-, di- or trisubstituted independently of one another by R13,
  22) —($C_0$-$C_4$)-alkylene-($C_3$-$C_8$)-cycloalkyl, wherein cycloalkyl is unsubstituted or mono-, di- or trisubstituted independently of one another by R13,
  23) —($C_0$-$C_3$)-alkylene-O—$CH_2$—$CF_2$—$CH_2$—O—($C_0$-$C_3$)-alkyl,
  24) —($C_0$-$C_3$)-alkylene-O—$CH_2$—$CF_2$—$CF_2$—$CH_2$—O—($C_0$-$C_3$)-alkyl,
  25) —($C_0$-$C_3$)-alkylene-O—$CH_2$—($C_1$-$C_3$)-perfluoroalkylene-$CH_2$—OH,
  26) —$SO_w$—N($R^{11}$)—R13, wherein w is 1 or 2,
  27) —($C_0$-$C_4$)-alkylene-C(O)—N($R^{11}$)—R13,
  28) —($C_0$-$C_4$)-alkylene-N($R^{11}$)—R13, or
  29) a residue from the following list

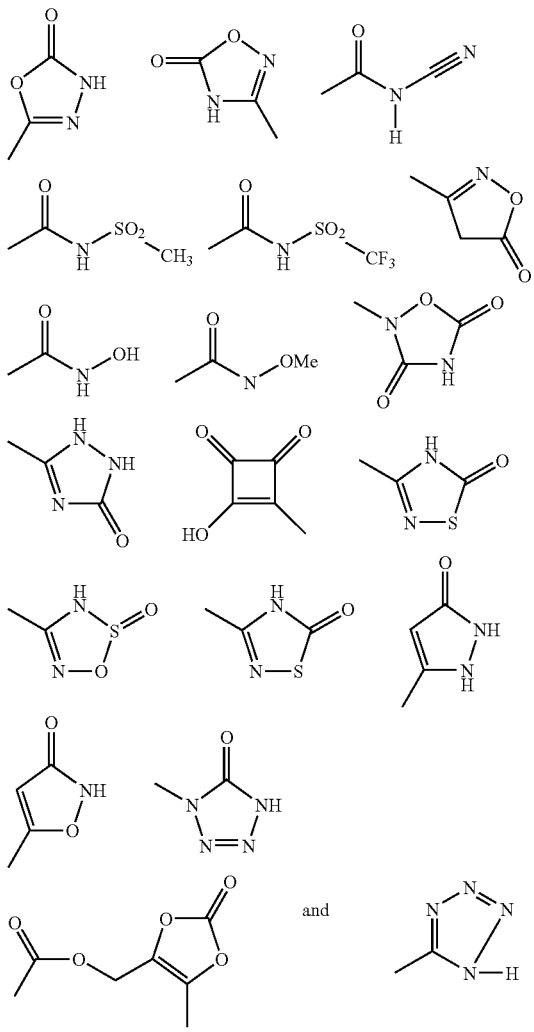

wherein Me is methyl,
if two —OR19 residues are attached to adjacent atoms they can form together with the atoms which they are attached to a 1,3-dioxole ring or a 2,3-dihydro-[1,4]dioxine ring, which is substituted one, two, three or four times by R13,
R11 and R12 are independently of one another identical or different and are
1) hydrogen atom,
2) —($C_1$-$C_6$)-alkyl, wherein alkyl is unsubstituted or mono-, di- or trisubstituted independently of one another by R13,
3) —($C_0$-$C_6$)-alkyl-($C_6$-$C_{14}$)-aryl, wherein aryl is as defined above and wherein alkyl and aryl are independently from one another unsubstituted or mono-, di- or trisubstituted by R13,
4) —O—$R^{17}$, or
5) —($C_0$-$C_6$)-alkyl-(4-$C_{15}$)-heterocyclyl, wherein alkyl and heterocyclyl is as defined above and independently from one another are unsubstituted or mono-, di- or trisubstituted by R13,
R11 and R12 together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, 1,4-oxazepine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, which is unsubstituted or mono-, di- or trisubstituted independently of one another by R13,
R4 and R22 in formula I or formula Ia together with the carbon atoms to which they are each bonded can form a phenyl residue,
R13 is fluorine, chlorine, bromine, iodine, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_0$-$C_3$)-alkylene-O—$R^{10}$, —Si—$(CH_3)_3$, —N($R^{10}$)—S(O)$_2$—$R^{10}$, —S—$R^{10}$, —$SO_2$—$R^{10}$, —S(O)$_2$—N($R^{10}$)—$R^{20}$, —C(O)—$R^{10}$, —($C_1$-$C_8$)-alkyl, —($C_1$-$C_8$)-alkoxy, phenyl, phenyl oxy-, —O—$CF_3$, —($C_1$-$C_3$)-perfluoroalkyl, —($C_0$-$C_4$)-alkyl-C(O)—O—C(R15, R16)—O—C(O)—R17, —($C_1$-$C_4$)-alkoxy-phenyl, —($C_0$-$C_4$)-alkyl-C(O)—O—C(R15, R16)—O—C(O)—O—R17, —O—R15, —NH—C(O)—NH—$R^{10}$, —NH—C(O)—O—$R^{10}$, or a residue from the following list

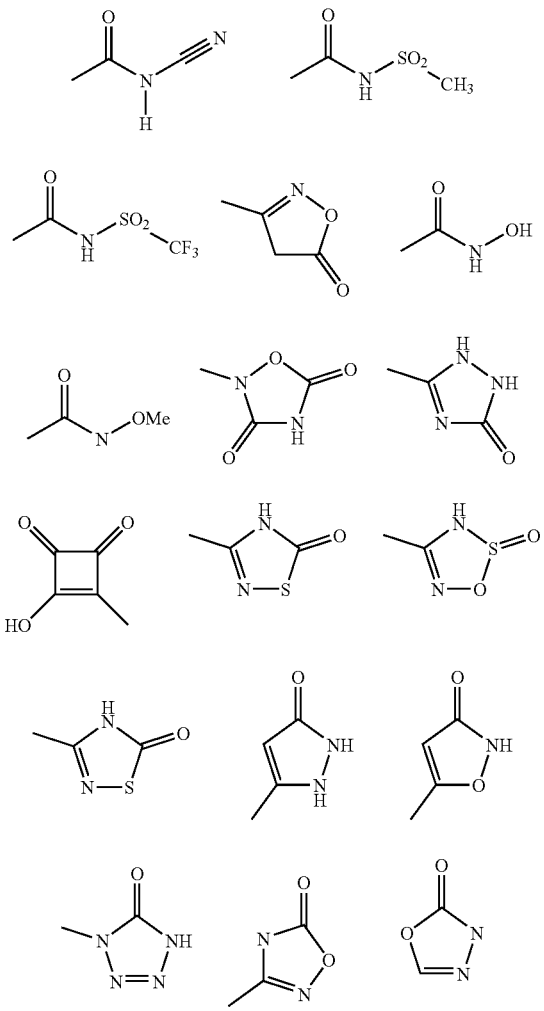

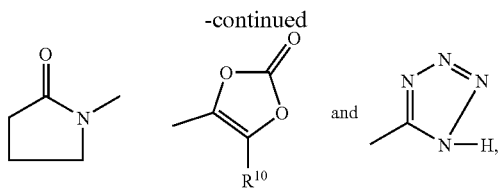

and wherein Me is methyl,
$R^{10}$ and $R^{20}$ are independently of one another hydrogen, —$(C_1$-$C_6)$-alkyl, —$(C_0$-$C_4)$-alkyl-OH, —$(C_0$-$C_4)$-alkyl-O—$(C_1$-$C_4)$-alkyl or —$(C_1$-$C_3)$-perfluoroalkyl,
R15 and R16 are independently of one another hydrogen, —$(C_1$-$C_6)$-alkyl, or together form a ring out of the group cyclopropyl, cyclobutyl, cyclopentyl or cyclohexyl, wherein each ring is unsubstituted or substituted one to three times by $R^{10}$, and
R17 is —$(C_1$-$C_6)$-alkyl, —$(C_1$-$C_6)$-alkyl-OH, —$(C_1$-$C_6)$-alkyl-O—$(C_1$-$C_6)$-alkyl, —$(C_3$-$C_8)$-cycloalkyl, —$(C_1$-$C_6)$-alkyl-O—$(C_1$-$C_8)$-alkyl-$(C_3$-$C_8)$-cycloalkyl, —$(C_1$-$C_6)$-alkyl-$(C_3$-$C_8)$-cycloalkyl, wherein said cycloalkyl ring is unsubstituted or substituted one, two or three times by —OH, —O—$(C_1$-$C_4)$-alkyl or $R^{10}$, in all its stereoisomeric forms and mixtures thereof in any ratio, and its physiologically tolerable salts.
5) The present invention also relates to the compounds of the formula I, wherein
R0 is 1) phenyl, wherein phenyl is unsubstituted or mono-, di- or trisubstituted independently of one another by R8,
  2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridinyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
  3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8,
  and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8
R8 is 1) F, Cl, Br or J,
  2) —$(C_1$-$C_4)$-alkyl, wherein alkyl is unsubstituted or mono-, di- or trisubstituted independently of one another by halogen, —OH or a methoxy residue, or
  3) —O—$(C_1$-$C_4)$-alkyl, wherein alkyl is unsubstituted or mono-, di- or
  trisubstituted independently of one another by halogen or a methoxy residue, provided that R8 is at least one halogen or —O—$(C_1$-$C_8)$-alkyl residue, if R0 is an aryl or a heterocyclyl, which are as defined above,
Q is —C(O)—-$(C_1$-$C_6)$-alkylene, —$(C_1$-$C_2)$-alkylene-C(O)—$NR^{10}$— or —$(C_0$-$C_3)$-alkylene-C(O)—O—$(C_0$-$C_2)$-alkylene,
$R^1$ is hydrogen atom, —$(C_1$-$C_2)$-alkyl, —$(C_1$-$C_3)$-alkylene-C(O)—NH—R0, —$(C_1$-$C_3)$-perfluoroalkylene, —$(C_1$-$C_3)$-alkylene-C(O)—O—R15, —$(C_1$-$C_3)$-alkylene-S(O)$_2$—$(C_1$-$C_3)$-alkyl or —$(C_1$-$C_3)$-alkylene-S(O)$_2$—N($R^{4'}$)—$R^{5'}$, wherein $R^{4'}$ and $R^{5'}$ are independent of one another are identical or different and are hydrogen atom or —$(C_1$-$C_4)$-alkyl,
$R^1$—N—V can form a 4- to 7-membered cyclic group out of the group azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14,
R14 is fluorine, chlorine, —OH, =O, —$(C_1$-$C_8)$-alkyl, —C(O)—OH, —CN, —NH$_2$, —C(O)—O—$(C_1$-$C_4)$-alkyl, —C(O)—NH—$(C_1$-$C_8)$-alkyl, —C(O)—N—[($C_1$-$C_8)$-alkyl]$_2$, —C(O)—NH$_2$ or —N($R^{18}$)—$R^{21}$, wherein $R^{18}$ and $R^{21}$ are independently from each other hydrogen atom, —$(C_1$-$C_3)$-perfluoroalkyl or —$(C_1$-$C_4)$-alkyl,
V is a heterocyclyl residue out of the group containing compounds which are derived from azaindole (1H-pyrrolopyridine), aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine, wherein said heterocyclyl residue is unsubstituted or mono-, di- or trisubstituted independently of one another by R14,
G is a direct bond, —(CH$_2$)$_m$—, or —(CH$_2$)$_m$—$NR^{10}$—,
m is the integers zero, 1, 2, 3 or 4,
M is 1) a hydrogen atom,
  3) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, 3) —($C_1$-$C_6$)-alkyl, wherein alkyl is unsubstituted or mono-, di- or trisubstituted independently of one another by R14,
4) ($C_3$-$C_6$)-cycloalkyl, or
5) —C(O)—N($R^{11}$)—$R^{12}$, R3, R4 and R22 are independent of one another are identical or different and are
1) hydrogen atom,
2) halogen,
3) —($C_1$-$C_4$)-alkyl, wherein alkyl is unsubstituted or mono-, di- or trisubstituted independently of one another by R13,
4) —($C_1$-$C_3$)-perfluoroalkyl,
5) phenyl, wherein phenyl is unsubstituted or mono-, di- or trisubstituted independently of one another by R13,
6) —($C_0$-$C_4$)-alkylene-O—R19, wherein R19 is
  a) hydrogen atom,
  b) —($C_1$-$C_4$)-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) —$CF_3$, or
  e) $CHF_2$,
7) —CN,
8) —$NR^{10}$—$SO_2$—$R^{10}$,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-c(0)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^{11}$)—$R^{12}$,
15) —($C_0$-$C_2$)alkylene-C(O)—O—($C_{2-4}$)-alkylene-O—C(O)—($C_1$-$C_4$)-alkyl,
16) —C(O)—O—C(R15, R16)—O—C(O)—R17,
17) —($C_0$-$C_2$)alkylene-C(O)—O—($C_2$-$C_4$)-alkylene-O—C(O)—O—($C_1$-$C_6$)-alkyl,
18) —C(O)—O—C(R15, R16)—O—C(O)—O—R17,
19) —($C_0$-$C_4$)-alkylene-($C_3$-$C_6$)-cycloalkyl, wherein cycloalkyl is unsubstituted or mono-, di- or trisubstituted independently of one another by R13, or
20) —($C_0$-$C_3$)-alkylene-O—$CH_2$—$CF_2$—$CH_2$—O—($C_0$-$C_3$)-alkyl
21) —($C_0$-$C_3$)-alkylene-O—$CH_2$—$CF_2$—$CF_2$—$CH_2$—O—($C_0$-$C_3$)-alkyl,
22) —($C_0$-$C_3$)-alkylene-O—$CH_2$—($C_1$-$C_3$)-perfluoroalkylene-$CH_2$—OH, or
23) —$SO_w$—N($R^{11}$)—$R^{13}$, wherein w is 1 or 2,
24) —($C_0$-$C_4$)-alkylene-C(O)—N($R^{11}$)—$R^{13}$,
25) —($C_0$-$C_4$)-alkylene-N($R^{11}$)—$R^{13}$, or
26) a residue from the following list

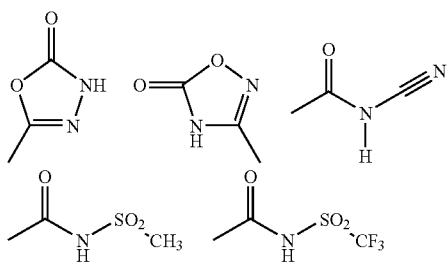

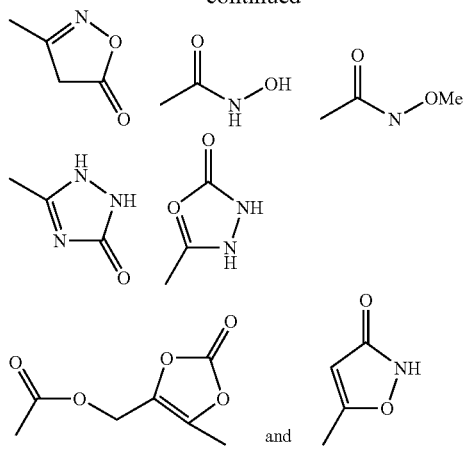
-continued wherein Me is methyl,
if two —OR19 residues are attached to adjacent atoms they can form together with the atoms which they are attached to a 1,3-dioxole ring or a 2,3-dihydro-[1,4]dioxine ring, which is substituted one, two, three or four times by R13, $R^{11}$ and $R^{12}$ together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, 1,4-oxazepine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said ring is unsubstituted or mono-, di- or trisubstituted independently of one another by R13, R4 and R22 in formula I or formula Ia together with the carbon atoms to which they are each bonded can form a phenyl residue, R13 is fluorine, chlorine, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_0$-$C_3$)-alkylene-O—$R^{10}$, —Si-$(CH_3)_3$, —N($R^{10}$)—$S(O)_2$—$R^{10}$, —S—$R^{10}$, —$SO_2$—$R^{10}$, —S(O)$_2$—N($R^{10}$)—$R^{20}$, —C(O)—$R^{10}$, —($C_1$-$C_8$)-alkyl, —($C_1$-$C_8$)-alkoxy, phenyl, phenyloxy-, —O—$CF_3$, —($C_1$-$C_3$)-perfluoroalkyl, —NH—C(O)—NH—$R^{10}$, —($C_0$-$C_4$)-alkyl-C(O)—O—C(R15, R16)—O—C(O)—R17, —($C_1$-$C_4$)-alkoxy-phenyl, —($C_0$-$C_4$)-alkyl-C(O)—O—C(R15, R16)—O—C(O)—O—R17, —O—R15, —NH—C(O)—O—$R^{10}$, or a residue from the following list

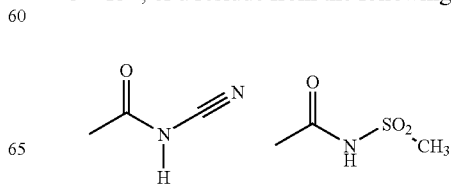

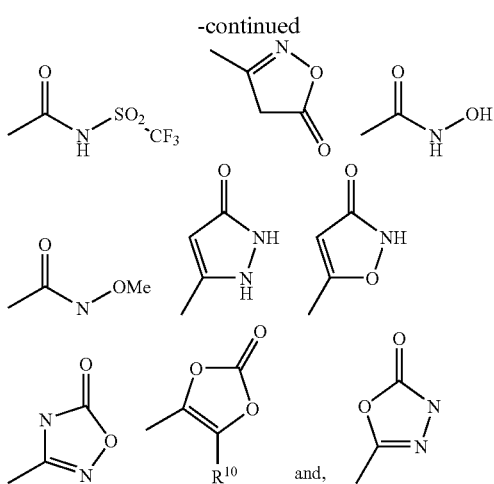

wherein Me is methyl,

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-alkyl or —(C$_1$-C$_3$)-perfluoroalkyl, R15 and R16 are independently of one another hydrogen, —(C$_1$-C$_6$)-alkyl, or together form a ring out of the group cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-O H, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

6) The present invention also relates to the compounds of the formula I, wherein R0 is 1) phenyl, wherein phenyl is unsubstituted or mono-, di- or trisubstituted independently of one another by R8, 2) a heterocyclyl selected out of the group indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, pyridinyl, purinyl and pteridinyl, wherein said heterocyclyl is unsubstituted or mono-, di- or trisubstituted independently of one another by R8, 3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1) is F, Cl, Br, J,

2) —(C$_1$-C$_4$)-alkyl, wherein alkyl is unsubstituted or mono-, di- or trisubstituted independently of one another by halogen, —OH or a methoxy residue, or 3) —O—(C$_1$-C$_4$)-alkyl, wherein alkyl is unsubstituted or mono-, di- or trisubstituted independently of one another by halogen or a methoxy residue, provided that R8 is at least one halogen or —O—(C$_1$-C$_8$)-alkyl residue, if R0 is an aryl or a heterocyclyl, which are as defined above, Q is —C(O)—; —C(O)—O-methylene, —(C$_1$-C$_4$)-alkylene or —(C$_0$-C$_2$)-alkylene-C(O)—NR$^{10}$—, R$^1$ is hydrogen atom or —(C$_1$-C$_2$)-alkyl, or R$^1$—N—V can form a 4- to 7-membered cyclic group out of the group piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluoro, chlorine, —(C$_1$-C$_4$)-alkyl or —NH$_2$, V is a heterocyclyl residue out of the group containing compounds, which are derived from azaindolyl (1H-pyrrolopyridyl), azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole, wherein said heterocyclyl residue is unsubstituted or mono-, di- or trisubstituted independently of one another by R14, G is a direct bond, —(CH$_2$)$_m$— or —(CH$_2$)$_m$—NR$^{10}$—, m is the integers zero, 1, 2, 3 or 4, M is 1) a hydrogen atom, 2) heterocyclyl, wherein heterocyclyl is a residue out of the group which can be derived from 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, wherein said heterocyclyl is unsubstituted or mono-, di- or trisubstituted independently of one another by R14, 3) —(C$_1$-C$_6$)-alkyl, wherein alkyl is unsubstituted or mono-, di- or trisubstituted independently of one another by R14, or 4) (C$_3$-C$_6$)-cycloalkyl, R3, R4 and R22 are independent of one another are identical or different and are
1) hydrogen atom,
2) halogen,
3) —($C_1$-$C_4$)-alkyl, wherein alkyl is unsubstituted or mono-, di- or trisubstituted independently of one another by R13,
4) —($C_1$-$C_3$)-perfluoroalkyl,
5) phenyl, wherein phenyl is unsubstituted or mono-, di- or trisubstituted independently of one another by R13,
6) —($C_0$-$C_4$)-alkylene-O—R19, wherein R19 is
   a) hydrogen atom,
   b) —($C_1$-$C_4$)-alkyl, wherein alkyl is unsubstituted or mono-, di- or trisubstituted independently of one another by R13, or
   c) phenyl, wherein phenyl is unsubstituted or mono-, di- or trisubstituted independently of one another by R13,
   d) —$CF_3$, or
   e) —$CHF_2$,
7) —CN,
8) —$NR^{10}$—$SO_2$—$R^{10}$,
9) —$SO_s$—$R^{11}$, wherein s is 1 or 2,
10) —$SO_t$—$N(R^{11})$—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—$N(R^{11})$—$R^{12}$,
14) —($C_0$-$C_4$)-alkylene-$N(R^{11})$—$R^{12}$,
15) —($C_0$-$C_2$)alkylene-C(O)—O—($C_{2-4}$)-alkylene-O—C(O)—($C_1$-$C_4$)-alkyl,
16) —C(O)—O—C(R15, R16)—O—C(O)—R17,
17) —($C_0$-$C_2$)alkylene-c(O)—O—($C_2$-$C_4$)-alkylene-O—C(O)—O—($C_1$-$C_6$)-alkyl,
18) —C(O)—O—C(R15, R16)—O—C(O)—O—R17,
19) —($C_0$-$C_3$)-alkylene-($C_3$-$C_6$)-cycloalkyl, wherein cycloalkyl is unsubstituted or mono-, di- or trisubstituted independently of one another by R13,
20) —($C_0$-$C_4$)-alkylene-($C_3$-$C_6$)-cycloalkyl, wherein cycloalkyl is unsubstituted or mono-, di- or trisubstituted independently of one another by R13, or
21) —($C_0$-$C_3$)-alkylene-O—$CH_2$—$CF_2$—$CH_2$—O—($C_0$-$C_3$)-alkyl,
22) —($C_0$-$C_3$)-alkylene-O—$CH_2$—$CF_2$—$CF_2$—$CH_2$—O—($C_0$-$C_3$)-alkyl,
23) —($C_0$-$C_3$)-alkylene-O—$CH_2$—($C_1$-$C_3$)-perfluoroalkylene-$CH_2$—OH, or
24) —$SO_w$—$N(R^{11})$—$R^{13}$, wherein w is 1 or 2,
25) —($C_0$-$C_4$)-alkylene-c(O)—$N(R^{11})$—$R^{13}$,
26) —($C_0$-$C_4$)-alkylene-$N(R^{11})$—R13, or
27) a residue from the following list

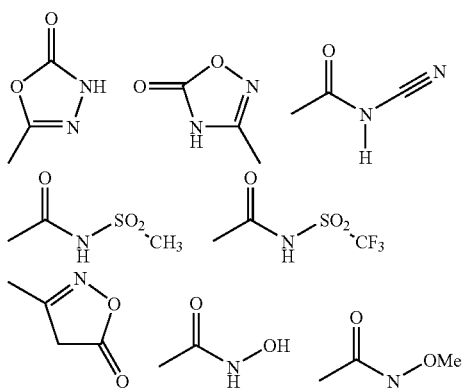

-continued

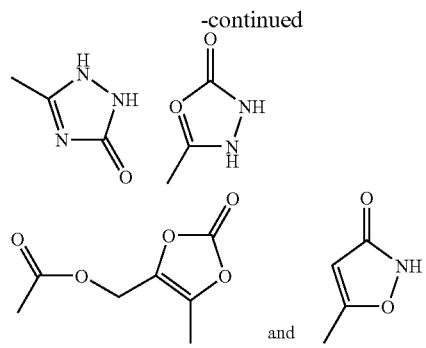

and wherein Me is methyl,
R11 and R12 are independently of one another identical or different and are
1) hydrogen atom,
2) —($C_1$-$C_4$)-alkyl, wherein alkyl is unsubstituted or mono-, di- or trisubstituted independently of one another by R13,
3) —($C_0$-$C_6$)-alkyl-($C_3$-$C_6$)-cycloalkyl,
4) —O—R17, or
5) —($C_0$-$C_6$)-alkyl-($C_4$-$C_{15}$)-heterocyclyl, wherein alkyl and heterocyclyl independently from one another are unsubstituted or mono-, di- or trisubstituted by R13 and wherein heterocyclyl is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, or
R11 and R12 together with the nitrogen atom to which they are bonded form a heterocyclic ring, which is selected out of the group azetidine, cyclopropyl, cyclobutyl, 4,5-dihydro-oxazole, imidazolidine, morpholine, (1,4)-oxazepane, 1,4-oxazepine, oxazolidine, piperidine, piperazine, pyrrolidine, tetrahydrothiophene, thiazolidine or thiomorpholine,
R4 and R22 in formula I or formula Ia together with the carbon atoms to which they are each bonded can form a phenyl residue,
R13 is fluorine, —CN, =O, —OH, —$CF_3$, —C(O)—O—$R^{10}$, —C(O)—$N(R^{10})$—$R^{20}$, —$N(R^{10})$—$R^{20}$, —($C_3$-$C_6$)-cycloalkyl, —($C_0$-$C_3$)-alkylene-O—$R^{10}$, —Si—$(CH_3)_3$, —S—$R^{10}$, —$SO_2$—$R^{10}$, —($C_1$-$C_3$)-perfluoroalkyl, or a residue from the following list

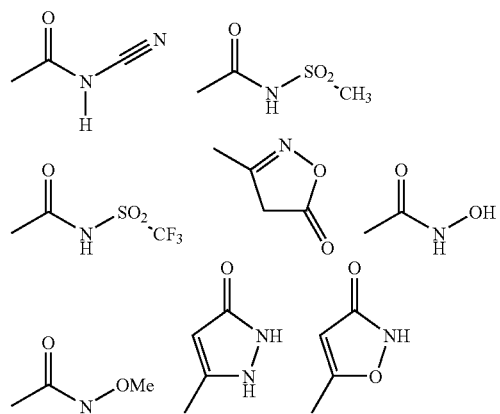

-continued

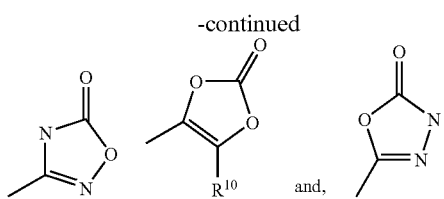

wherein Me is methyl,

R$^{10}$ and R$^{20}$ are independently of one another hydrogen, —(C$_1$-C$_4$)-alkyl or —(C$_1$-C$_3$)-perfluoroalkyl, R$^{15}$ and R$^{16}$ are independently of one another hydrogen, —(C$_1$-C$_4$)-alkyl, or together form a ring out of the group cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

7) The present invention also relates to the compounds of the formula I, wherein R0 is 1) phenyl, wherein phenyl is unsubstituted or mono- or disubstituted independently of one another by R8,
   2) pyridyl, wherein pyridyl is unsubstituted or mono- or disubstituted independently of one another by R8, or
   3) a heterocyclyl out of the group thienyl, thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8, R8 is F, Cl, Br, —O—CH$_3$ or —O—CF$_3$, Q is —C(O)—; —C(O)—O-methylene, —CH$_2$—C(O)—NH—, methylene or ethylene, R$^1$ is hydrogen atom, R$^1$—N—V can form a 4- to 8-membered cyclic group out of the group azetidine, pyrrolidine, piperidine and piperazine, R14 is fluorine, chlorine, methyl, ethyl or —NH$_2$, V is a heterocyclyl out of the group containing compounds which is derived from azaindolyl (1H-pyrrolopyridyl), azetidine, 1,4-diazepane, isoxazole, isoquinoline, piperazine, piperidine, pyrazine, pyridazine, pyrimidine, pyrrolidine, quinazoline, quinoline or tetrahydropyrane,
   wherein said heterocyclyl residue is unsubstituted or mono- or disubstituted independently of one another by R14, G is a direct bond, —(CH$_2$)$_m$—, or —(CH$_2$)$_m$—NR$^{10}$—, m is the integers zero, 1 or 2, M is a hydrogen atom, (C$_2$-C$_4$)-alkyl, isopropyl, azepanyl, cyclopropyl, cyclobutyl, cyclopentyl, cyclohexyl, imidazolyl, ketomorpholinyl, morpholinyl, [1,4]Oxazepanyl, piperidinyl, piperidonyl, pyrazinyl, pyrazolyl, pyridazinyl, pyridinyl, pyrimidyl, pyrrolidinyl, 1,4,5,6-tetrahydro-pyridazinyl, or tetrahydropyranyl, wherein the residues are unsubstituted or mono- or disubstituted independently of one another by R14

R3, R4 and R22 are independent of one another are identical or different and are
   1) hydrogen atom,
   2) fluorine, chlorine, bromine, iodine,
   3) —(C$_1$-C$_4$)-alkyl, wherein alkyl is unsubstituted or mono-, di- or trisubstituted independently of one another by R13,
   4) —(C$_1$-C$_3$)-perfluoroalkyl,
   5) phenyl, wherein phenyl is unsubstituted or mono-, di- or trisubstituted independently of one another by R13,
   6) —(C$_0$-C$_2$)-alkylene-O—R19, wherein R19 is
     a) hydrogen atom,
     b) —(C$_1$-C$_4$)-alkyl, wherein alkyl is unsubstituted or mono-, di- or trisubstituted independently of one another by R13, or
     c) phenyl, wherein phenyl is unsubstituted or mono-, di- or trisubstituted independently of one another by R13,
     d) —CF$_3$, or
     e) —CHF$_2$
   7) —NO$_2$,
   8) —NR$^{10}$—SO$_2$—R$^{10}$,
   9) —SO$_s$—R$^{11}$, wherein s is 1 or 2,
   10) —SO$_t$—N(R$^{11}$)—R$^{12}$, wherein t is 1 or 2,
   11) —(C$_0$-C$_4$)-alkylene-C(O)—R$^{11}$,
   12) -(Co-4)-alkylene-C(O)—O—R$^{11}$,
   13) —(C$_0$-C$_4$)-alkylene-C(O)—N(R$^{11}$)—R$^{12}$,
   14) -(C$_0$-C$_4$)-alkylene-N(R$^{11}$)—R$^{12}$,
   15) —(C$_0$-C$_2$)alkylene-C(O)—O—(C$_{2-4}$)-alkylene-O—C(O)—(C$_1$-C$_4$)-alkyl,
   16) —C(O)—O—C(R15, R16)—O—C(O)—R17,
   17) —(C$_0$-C$_2$)alkylene-C(O)—O—(C$_2$-C$_4$)-alkylene-O—C(O)—O—(C$_1$-C$_6$)-alkyl,
   18) —C(O)—O—C(R15, R16)—O—C(O)—O—R17,
   19) —(C$_0$-C$_3$)-alkylene-phenyl, wherein phenyl is unsubstituted or mono-, di- or trisubstituted independently of one another by R13,
   20) pyridinyl, wherein pyridinyl is unsubstituted or mono-, di- or trisubstituted independently of one another by R13,
   21) thiazolyl, wherein thiazolyl is unsubstituted or mono-, di- or trisubstituted independently of one another by R13,
   22) —(C$_0$-C$_4$)-alkylene-(C$_3$-C$_6$)-cycloalkyl, wherein cycloalkyl is unsubstituted or mono-, di- or trisubstituted independently of one another by R13,
   23) —(C$_0$-C$_3$)-alkylene-O—CH$_2$—CF$_2$—CH$_2$—O—(C$_0$-C$_3$)-alkyl,
   24) —(C$_0$-C$_3$)-alkylene-O—CH$_2$—CF$_2$—CF$_2$—CH$_2$—O—(C$_0$-C$_3$)-alkyl,
   25) —(C$_0$-C$_3$)-alkylene-O—CH$_2$—(C$_1$-C$_3$)-perfluoroalkylene-CH$_2$—OH, or
   26) a residue from the following list

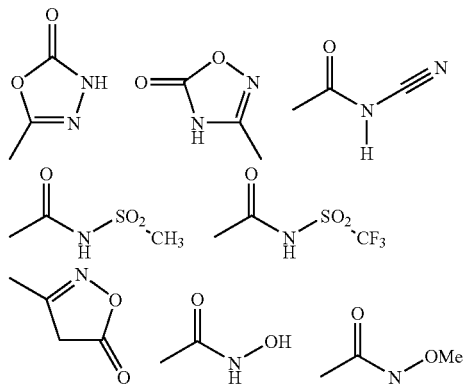

-continued

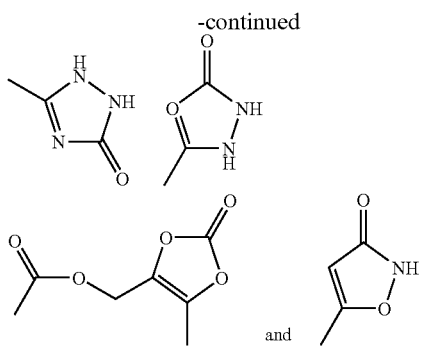

wherein Me is methyl,
R11 and R12 are independently of one another identical or different and are
1) hydrogen atom,
2) —(C$_1$-C$_4$)-alkyl, wherein alkyl is unsubstituted or mono-, di- or trisubstituted independently of one another by R13,
3) —(C$_0$-C$_6$)-alkyl-phenyl,
4) —O—R$^{17}$, or
5) —(C$_0$-C$_6$)-alkyl-heterocyclyl, wherein alkyl and heterocyclyl independently from one another are unsubstituted or mono-, di- or trisubstituted by R13 and wherein heterocyclyl is selected out of the group azetidine, imidazolidine, morpholine, (1,4)-oxazepane or piperidine or R11 and R12 together with the nitrogen atom to which they are bonded can form a ring, which is selected out of the group azetidine, imidazolidine, morpholine, (1,4)-oxazepane, 1,4-oxazepine, piperazine, piperidine, pyrrolidine or thiomorpholine, R13 is fluorine, chlorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_6$)-cycloalkyl, —(C$_0$-C$_3$)-alkylene-O—R$^{10}$, —Si—(CH$_3$)$_3$, —S—R$^{10}$, —SO$_2$—R$^{10}$, —(C$_1$-C$_4$)-alkyl, —(C$_1$-C$_3$)-perfluoroalkyl, or a residue from the following list

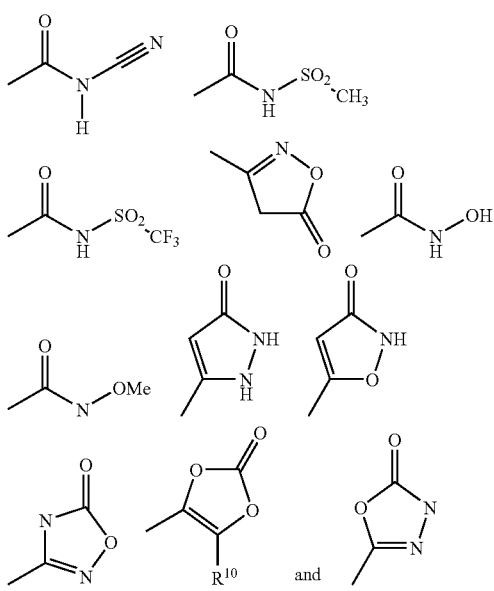

wherein Me is methyl,
R$^{10}$ and R$^{20}$ are independently of one another hydrogen, —(C$_1$-C$_4$)-alkyl or —(C$_1$-C$_3$)-perfluoroalkyl,
R$^{15}$ and R$^{16}$ are independently of one another hydrogen, —(C$_1$-C$_4$)-alkyl, or together form a ring out of the group cyclopropyl, cyclobutyl, cyclopentyl or cyclohexyl, wherein each ring is unsubstituted or substituted one to three times by R$^{10}$, and
R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

The present invention also relates to the compounds of the formulae I and Ia, which are 1-[5-(5-Chloro-thiophen-2-yl)-isoxazol-3-ylmethyl]-1H-pyrrole-2-carboxylic acid (1-isopropyl-piperidin-4-yl)-amide 1-(3-Methoxy-benzyl)-1H-pyrrole-2-carboxylic acid (1-isopropyl-piperidin-4-yl)-amide 1-[5-(5-Chloro-thiophen-2-yl)-isoxazol-3-ylmethyl]-4-nitro-1H-pyrrol e-2-carboxylic acid (1-isopropyl-piperidin-4-yl)-amide 1-[5-(5-Chloro-thiophen-2-yl)-isoxazol-3-ylmethyl]-3,5-dimethyl-1H-pyrrole-2-carboxylic acid (1-isopropyl-piperidin-4-yl)-amide 1-[(5-Chloro-pyridin-2-ylcarbamoyl)-methyl]-4-(perhydro-1,4-oxazepine-4-carbonyl)-1H-pyrrole-2-carboxylic acid (1-isopropyl-piperidin-4-yl)-amide 1-[(5-Chloro-pyridin-2-ylcarbamoyl)-methyl]-5-(perhydro-1,4-oxazepine-4-carbonyl)-1H-pyrrole-2-carboxylic acid (1-isopropyl-piperidin-4-yl)-amide 1-[5-(5-Chloro-thiophen-2-yl)-isoxazol-3-ylmethyl]-5-(perhydro-1,4-oxazepine-4-carbonyl)-1H-pyrrole-2-carboxylic acid (1-isopropyl-piperidin-4-yl)-amide 3-[1-[5-(5-Chloro-thiophen-2-yl)-isoxazol-3-ylmethyl]-5-(1-isopropyl-piperidin-4-yl carbamoyl)-2,4-dimethyl-1H-pyrrol-3-yl]-propionic acid 1-[5-(5-Chloro-thiophen-2-yl)-isoxazol-3-ylmethyl]-5-(1-isopropyl-piperidin-4-ylcarbamoyl)-1H-pyrrole-2-carboxylic acid benzyl ester, 1-[5-(5-Chloro-thiophen-2-yl)-isoxazol-3-ylmethyl]-5-(1-isopropyl-piperidin-4-yl carbamoyl)-1H-pyrrole-2-carboxylic acid methyl ester, 1-[5-(5-Chloro-thiophen-2-yl)-isoxazol-3-ylmethyl]-5-(1-isopropyl-piperidin-4-ylcarbamoyl)-1H-pyrrole-2-carboxylic acid, 1-[(5-Chloro-pyridin-2-ylcarbamoyl)-methyl]-4-(1-isopropyl-piperidin-4-yl carbamoyl)-1H-pyrrole-2-carboxylic acid benzyl ester, 1-[5-(5-Chloro-thiophen-2-yl)-isoxazol-3-ylmethyl]-4-(1-isopropyl-piperidin-4-ylcarbamoyl)-1H-pyrrole-2-carboxylic acid benzyl ester, 1-[(5-Chloro-pyridin-2-yl carbamoyl)-methyl]-4-nitro-1H-pyrrole-2-carboxylic acid (1-isopropyl-piperidin-4-yl)-amide, 1-[(5-Chloro-pyridin-2-yl carbamoyl)-methyl]-4-(1-isopropyl-piperidin-4-ylcarbamoyl)-1H-pyrrol e-2-carboxylic acid methyl ester, 1-[5-(5-Chloro-thiophen-2-yl)-isoxazol-3-ylmethyl]-4-(1-isopropyl-piperidin-4-ylcarbamoyl)-1H-pyrrole-2-carboxylic acid methyl ester, 1-[5-(5-Chloro-thiophen-2-yl)-isoxazol-3-ylmethyl]-4-(1-isopropyl-piperidin-4-ylcarbamoyl)-1H-pyrrole-2-carboxylic acid, 1-[5-(5-Chloro-thiophen-2-yl)-isoxazol-3-ylmethyl]-5-(3-methoxy-azetidine-1-carbonyl)-1H-pyrrole-2-carboxylic acid (1-isopropyl-piperidin-4-yl)-amide, 1-[5-(5-Chloro-thiophen-2-yl)-isoxazol-3-ylmethyl]-1H-pyrrole-2,5-dicarboxylic acid 2-[(1-isopropyl-piperidin-4-yl)-amide] 5-[(2-methoxy-ethyl)-amide], 1-[5-(5-Chloro-thiophen-2-yl)-isoxazol-3-ylmethyl]-1H-pyrrole-2,5-dicarboxylic acid 2-[(1-isopropyl-piperidin-4-yl)-amide] 5-[(2-methoxy-ethyl)-methyl-amide], 1-[5-(5-Chloro-thiophen-2-yl)-isoxazol-3-ylmethyl]-5-phenyl-1H-pyrrole-2-carboxylic acid (1-isopropyl-piperidin-4-yl)-amide or 1-[5-(5-Chloro-thiophen-2-yl)-isoxazol-3-ylmethyl]-3,5-dimethyl-4-(perhydro-1,4-oxazepine-4-sulfonyl)-1H-pyrrole-2-carboxylic acid (1-isopropyl-piperidin-4-yl)-amide.

In general, the meaning of any group, residue, heteroatom, number etc., which can occur more than once in the compounds of the formulae I and Ia is independent of the meaning of this group, residue, heteroatom, number etc. in any other occurrence. All groups, residues, heteroatoms, numbers etc., which can occur more than once in the compounds of the formulae I and Ia can be identical or different.

As used herein, the term alkyl is to be understood in the broadest sense to mean hydrocarbon residues which can be linear, i.e. straight-chain, or branched. Examples of "—($C_1$-$C_8$)-alkyl" or "—($C_1$-$C_8$)-alkylene" are alkyl residues containing 1, 2, 3, 4, 5, 6, 7 or 8 carbon atoms are methyl, methylene, ethyl, ethylene. propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—($C_0$-$C_6$)-alkyl" or "—($C_0$-$C_8$)-alkylene" is a hydrocarbon residue containing 1, 2, 3, 4, 5, 6, 7 or 8 carbon atoms. The term "—$C_0$-alkyl" or "—$C_0$-alkylene" is a covalent bond.

Examples of —($C_3$-$C_8$)-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The terms "a monocyclic or bicyclic 6- to 14-membered aryl" or "—($C_6$-$C_{14}$)-aryl" are understood as meaning aromatic hydrocarbon radicals containing from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "mono- or bicyclic 4- to 15-membered heterocyclyl" or "—($C_4$-$C_{15}$)-heterocyclyl" refer to heterocycles in which one or more of the 4 to 15 ring carbon atoms are replaced by heteroatoms such as nitrogen, oxygen or sulfur.

Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxol enyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

Preferred are heterocyclyls, such as benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl and 3-thienyl.

Also preferred are:

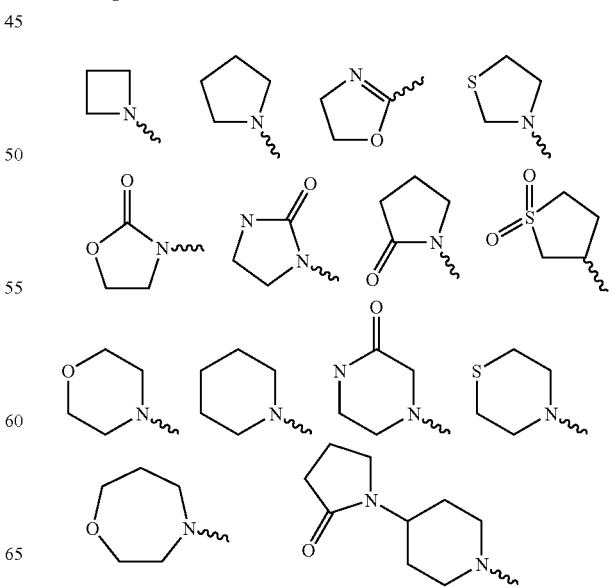

-continued

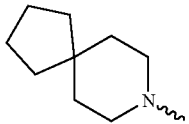

The terms "het" or "a 3- to 7-membered cyclic residue, containing up to 1, 2, 3 or 4 heteroatoms" refer to structures of heterocycles which can be derived from compounds such as azepine, azetidine, aziridine, azirine, 1,4diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "$R^1$—N—V can form a 4- to 8-membered cyclic group" or "$R^{11}$ and $R^{12}$ together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which can be derived from compounds such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "$R^{15}$ and $R^{16}$ together with the carbon atom to which they are bonded can form a 3to 6 membered carbocyclic ring" refer to structures, which can be derived from compounds such as cyclopropyl, cyclobutyl, cyclopentyl or cyclohexyl.

The term "$R^1$ and R22 together with the atoms to which they are bonded can form a 6- to 8-membered cyclic group, containing up to 1, 2, 3 or 4 heteroatoms chosen from nitrogen, sulfur or oxygen" refers to structures of heterocycles which can be derived from compounds such as azocane, azocane-2-one, cyloheptyl cyclohexyl, cyclooctane, cyclooctene, 1,4-diazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,4-oxazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxa-thiepane, 1,2-oxazine, 1,3-oxazine, 1,4-oxazine, [1,4]oxazocane, [1,3]oxazocan-2-one, oxocane, oxocan-2-one, phenyl, piperazine, piperidine, pyran, pyrazine, pyridazine, pyrimidine, 5,6,7,8-tetrahydro-1H-azocin-2-one or thiomorpholine.

The fact that many of the before-listed names of heterocycles are the chemical names of unsaturated or aromatic ring systems does not imply that the, the 4-15 membered mono- or polycyclic group could only be derived from the respective unsaturated ring system. The names here only serve to describe the ring system with respect to ring size and the number of the heteroatoms and their relative positions. As explained above, the 4-15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc. The term "—$(C_1$-$C_3)$-perfluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—$(C_1$-$C_3)$-perfluoroalkylene" is a partial or totally fluorinated alkylene-residue, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$-, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—, —$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—, —$CF_2$—$CH_2$—$CF_2$—, —$CF_2$—$CH_2$—$CHF$—, —$CF_2$—$CF_2$—$CF_2$—, or —$CF_2$—$CF_2$—$CHF$.

Halogen is fluorine, chlorine, bromine or iodine, preferably fluorine, chlorine or iodune, particularly preferably chlorine or iodine.

Optically active carbon atoms present in the compounds of the formulae I or Ia can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formulae I and Ia, and it comprises all ratios of the stereoisomers in the mixtures. In case the compounds of the formulae I and Ia can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I or Ia.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formulae I or Ia can also be obtained by employing stereochemically uniform starting materials or by using stereoselective reactions.

Physiologically tolerable salts of the compounds of formulae I and Ia are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formulae I and Ia, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formulae I and Ia, which simultaneously contain a basic group and an acidic group, for example a guanidino group and a carboxyl group, can also be present as zwitterions (betaines), which are likewise included in the present invention.

Salts of compounds of the formulae I and Ia can be obtained by customary methods known to those skilled in the art, for example by combining a compound of the formulae I and Ia with an inorganic or organic acid or base in a solvent or dispersant, or from other salts by cation exchange or anion exchange. The present invention also includes all salts of the compounds of the formulae I and Ia which, because of low physiologically tolerability, are not directly suitable for use in pharmaceuticals but are suitable, for example, as intermediates for carrying out further chemical modifications of the compounds of the formulae I and Ia or as starting materials for the preparation of physiologically tolerable salts.

The present invention furthermore includes all solvates of compounds of the formulae I and Ia, for example hydrates or adducts with alcohols.

The invention also includes derivatives and modifications of the compounds of the formulae I and Ia, for example prodrugs, protected forms and other physiologically tolerable derivatives, as well as active metabolites of the compounds of the formulae I and Ia. The invention relates in particular to prodrugs and protected forms of the compounds of the formulae I and Ia, which can be converted into compounds of the formulae I and Ia under physiological conditions. Suitable prodrugs for the compounds of the formulae I and Ia, i.e. chemically modified derivatives of the compounds of the formulae I and Ia having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formulae I and Ia are especially acyl prodrugs and carbamate prodrugs of acylatable nitrogen-containing groups such as amino groups and the guanidino group and also ester prodrugs and amide prodrugs of carboxylic acid groups which may be present in compounds of the formulae I and Ia. In the acyl prodrugs and carbamate prodrugs one or more, for example one or two, hydrogen atoms on nitrogen atoms in such groups are replaced with an acyl group or a carbamate, preferably a —($C_1$-$C_6$)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, ($C_1$-$C_8$)-alkyl, ($C_3$-$C_8$)-cycloalkyl, ($C_3$-$C_3$)-cycloalkyl-($C_1$-$C_4$)-alkyl-, ($C_6$-$C_{14}$)-aryl, Het-, ($C_6$-$C_{14}$)-aryl-($C_1$-$C_4$)-alkyl- or Het-($C_1$-$C_4$)-alkyl- and in which $R^{p2}$ has the meanings indicated for $R^{p1}$ with the exception of hydrogen.

Especially preferred compounds of the formulae I and Ia are those wherein two or more residues are defined as indicated before for preferred compounds of the formulae I and Ia, or residues can have one or some of the specific denotations of the residues given in their general definitions or in the definitions of preferred compounds before. All possible combinations of definitions given for preferred definitions and of specific denotations of residues explicitly are a subject of the present invention.

Also with respect to all preferred compounds of the formulae I and Ia all their stereoisomeric forms and mixtures thereof in any ratio and their physiologically acceptable salts explicitly are a subject of the present invention, as well as are their prodrugs. Similarly, also in all preferred compounds of the formulae I and Ia, all residues that are present more than one time in the molecule are independent of each other and can be identical or different.

The compounds of the formulae I and Ia can be prepared by utilising procedures and techniques, which per se are well known and appreciated by one of ordinary skill in the art. Starting materials or building blocks for use in the general synthetic procedures that can be applied in the preparation of the compounds of formulae I and Ia are readily available to one of ordinary skill in the art. In many cases they are commercially available or have been described in the literature. Otherwise they can be prepared from readily available precursor compounds analogously to procedures described in the literature, or by procedures or analogously to procedures described in this application.

The compounds of the formulae I and Ia can be prepared by utilising procedures and techniques, which per se are well known and appreciated by one of ordinary skill in the art. Starting materials or building blocks for use in the general synthetic procedures that can be applied in the preparation of the compounds of formulae I and Ia are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formulae I and Ia can be prepared, for example in the course of a convergent synthesis, by linking two or more fragments which can be derived retrosynthetically from the formulae I and Ia. More specifically, suitably substituted starting pyrrole derivatives are employed as building blocks in the preparation of the compounds of formulae I and Ia. If not commercially available, such pyrrole derivatives can be prepared according to the well-known standard procedures for the formation of the pyrrole ring system. By choosing suitable precursor molecules, these pyrrole syntheses allow the introduction of a variety of substituents into the various positions of the pyrrole system, which can be chemically modified in order to finally arrive at the molecule of the formulae I and Ia having the desired substituent pattern. As one of the comprehensive reviews in which numerous details and literature references on the chemistry of pyrrole and on synthetic procedures for their preparation can be found, C. W. Bird in "*Comprehensive Heterocyclic Chemistry*" Vol. 4, C. W. Bird and G. W. H. Cheeseman, eds., Pergamon Press, Oxford, 1984; R. J. Sundberg in "*Comprehensive Heterocyclic Chemistry II*" Vol. 2, A. Katritzky, Ch. Rees, E. Scriven, eds., Elsevier 1996; A. Gossauer in Houben-Weyl, "*Methoden der Organischen Chemie*" (Methods of Organic Chemistry), Thieme, Stuttgart, Germany 1994, Vol. E6a "*Hetarene I*"; D. M. Ketcha, *Progress in Heterocydic Chemistry* 2002, 14, 114-138; D. M. Ketcha, *Progress in Heterocyclic Chemistry* 2001, 13, 111-129; D. M. Ketcha, *Progress in Heterocyclic Chemistry* 2000, 12, 114-133; D. S. Black, *Science of Synthesis* 2002, 9, 441-552; D. van Leusen, A. M. van Leusen, *Organic Reactions* 2001, 57, 417-666; V. F. Ferreira et al., *Org. Prep. Proced. Int.* 2001,33, 411-454.

If starting pyrrole derivatives are not commercially available and have to be synthesized this can be done, for example, according to the well-known pyrrole syntheses mentioned above. In the following procedures of particular interest for the embodiment of this invention are listed and referenced briefly, however, they are standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modern separation techniques like, for example, preparative HPLC.

Illustrative Examples for Some General Methods:

1) Preparation of pyrroles from β-dicarbonyl compounds, a-halo carbonyl compounds and amines (Hantzsch synthesis):

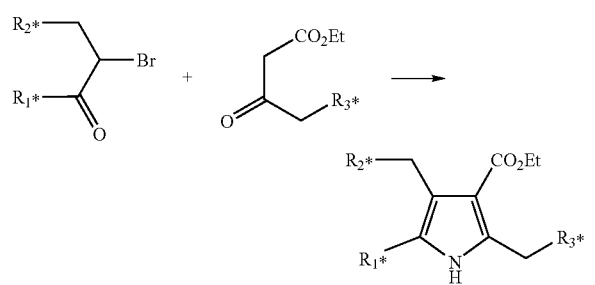

A. Hantzsch, *Ber. Dtsch. Chem. Ges.* 1890,23,1474

2) Pyrroles from 1,4-diketo compounds and amino compounds (Paal-Knorr-Synthesis):

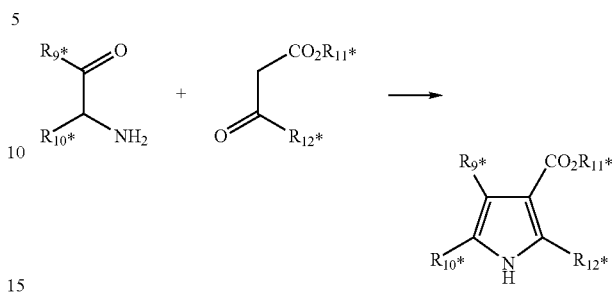

a) W. J. Thomson and L. A. Buhr, *J. Org. Chem.* 1983, 48, 2769 b) H. Stetter and R. Lauterbach, Liebigs Ann. Chem. 1962, 655, 20

3) Pyrroles from α-aminocarbonyl compounds and activated ketones (Knorr Synthesis):

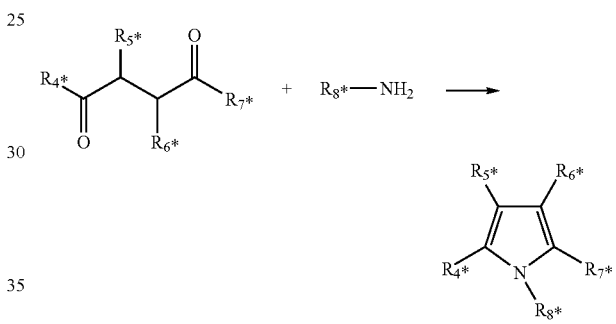

a) H. Ogoshi et al., *Tetrahedron Lett.* 1983,24, 929 b) J. V. Cooney, E. J. Beal and R. N. Hazlett, *Org. Prep. Proced. Int.* 1983, 15, 292 c) J. M. Hamby and J. C. Hodges, *Heterocycles* 1993, 35, 843

4) 2-Hydroxypyrroles can be obtained by intramolecular aldol condensation of α-acylamino ketones:

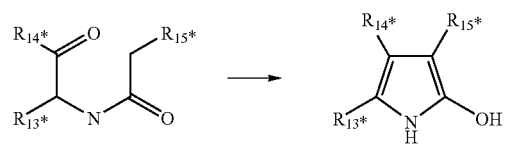

a) T. Kato, M. Sato and T. Yoshida, *Chem. Pharm. Bull.* 1971, 19, 292 b) R. L. Wineholt, E. Wyss and J. A. Moore, *J. Org. Chem.* 1966,31,48

5) Synthesis of 2-aminopyrroles:

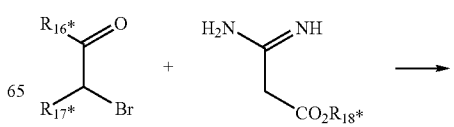

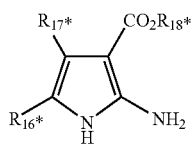

M. T. Cocco et al., *Farmaco Ed. Sci.* 1988, 43, 103

6) 2,5-unsubstituted pyrroles:

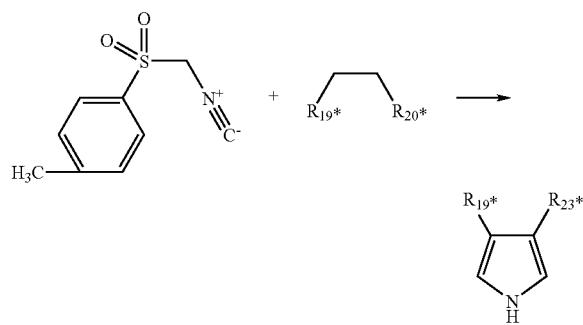

A. M. van Leusen et al., *Tetrahedron Lett.* 1972, 5337

7) Reaction of 1,3-dicarbonyl compounds and glycine esters to form pyrrole-2-esters:

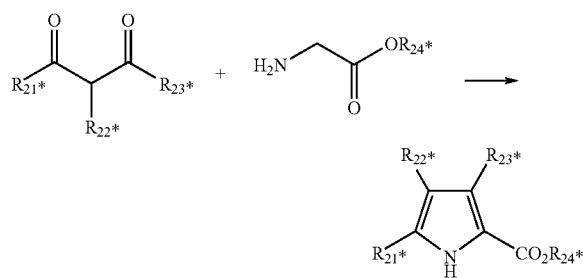

a) S. Mataka et al., *Synthesis* 1982, 157
b) G. H. Walizei and E. Breitmaier, *Synthesis* 1989, 337
c) H. K. Hombrecher and G. Horter, *Synthesis* 1990, 389

Further, in order to obtain the desired substituents at the pyrrole ring system in the formulae I and Ia, the functional groups introduced into the ring system during the pyrrole synthesis can be chemically modified. Especially the groups present in the pyrrole ring system can be modified by a variety of reactions and thus the desired residues be obtained. For example, a pyrrole carrying a hydrogen atom in the 2- or 3-position can also be obtained by saponification and subsequent decarboxylation of pyrrole carrying an ester group in the respective position. Alkyl- or hydroxymethyl groups as well as formyl groups attached to the pyrrole core can be transformed to a variety of functional groups, for example, to the corresponding carboxylic acid or carboxylic ester by many oxidative reactions well known to those skilled in the art. Moreover a nitrile group attached to the pyrrole ring can, for example, easily be converted into the desired acid under acidic or basic conditions. In addition, carboxylic acid groups and acetic acid groups in the 2-position, the 3-position, the 4-position and the 5-position can be converted into their homologues by usual reactions for chain elongation of carboxylic acids. Halogen atoms can be introduced into the 2-position, the 3-position, the 4-position and the 5-position, for example according to procedures like the following described in the literature. For the fluorination of pyrroles 1-chloromethyl-4-fluoro-1,4-diazoniabicyclo[2.2.2] octane bis(tetrafluoroborate) ("selectfluor") can be employed, see J. Wang and A. I. Scott, *J. Chem. Soc., Chem. Commun.* 1995, 2399. However, other suitable fluorinating reagents may also be employed where appropriate, e.g. xenon difluoride (J. Wang and A. I. Scott, *Tetrahedron* 1994, 50, 6181). The chlorination, bromination, or iodination of pyrroles can be accomplished by the reaction with elemental halogens or by the use of NCS, NBS or NIS and many other reagents well known to those skilled in the art. In addition suitable procedures are for example reported by H. J. Anderson and S.-F. Lee, *Can. J. Chem.* 1965, 43, 409; H. M. Gilow, D. E. Burton, *J. Org. Chem.* 1981, 46, 2221; S. Petruso et al., *J. Heterocycl. Chem.* 1990, 27, 1209; M. D'Auria et al., *J. Chem. Soc., Perkin Trans.* 1 1997, 2369. Depending on the reaction conditions, reagent, stocheiometry and substitution pattern the halogen is introduced in the 2-position and/or 3-position and/or 4-position and/or 5-position. By selective halogen/metal exchange or metalation by selective hydrogen/metal exchange and subsequent reaction with a wide range of electrophiles various substituents can be introduced at the heterocyclic nucleus (J. A. Ganske et al., *J. Org. Chem.* 1989, 54,4801; D. Monti and G. Sleiter, *Gazz. Chim. Ital.* 1990, 120, 587; A. Furstner, R. Singer and P. Knochel, *Tetrahedron Lett.* 1994, 35,1047; A. Minato et al., Tetrahedron Lett. 1981, 22, 5319). Halogens or hydroxy groups (via their triflates or nonaflates)—or primary amines (via their diazonium salts) present in the pyrrole structure—can be converted directly, or after interconversion to the corresponding stannane, or boronic acid, into a variety of other functional groups like for example —CN, —CF$_3$, —C$_2$F$_5$, ethers, acids, amides, amines, alkyl- or aryl-groups mediated by means of transition metals, namely palladium or nickel catalysts or copper salts and reagents for example referred to below (F. Diederich, P. Stang, "*Metal-catalyzed Cross-coupling Reactions*", Wiley-VCH, 1998; or M. Beller, C. Bolm, "*Transition Metals for Organic Synthesis*", Wiley-VCH, 1998; J. Tsuji, "*Palladium Reagents and Catalysts*", Wiley, 1996; J. Hartwig, *Angew. Chem.* 1998, 110,2154; B. Yang, S. Buchwald, *J. Organomet Chem.* 1999, 576,125; T. Sakamoto, K. Ohsawa, *J. Chem. Soc. Perkin Trans I* 1999, 2323; D. Nichols, S. Frescas, D. Marona-Lewicka, X. Huang, B. Roth, G. Gudelsky, J. Nash, *J. Med. Chem.* 1994, 37,4347; P. Lam, C. Clark, S. Saubern, J. Adams, M. Winters, D. Chan, A. Combs, *Tetrahedron Lett.* 1998, 39, 2941; D. Chan, K. Monaco, R. Wang, M. Winters, *Tetrahedron Lett.* 1998, 39, 2933; V. Farina, V. Krishnamurthy, W. Scott, "*The Stille Reaction*", Wiley, 1994; F. Qing et al., *J. Chem. Soc. Perkin Trans. 1* 1997, 3053; S. Buchwald et al., *J. Am. Chem. Soc.* 2001, 123, 7727; S. Buchwald et al., *Organic Lett.* 2002, 4, 581; T. Fuchikami et al., *Tetrahedron Lett.* 1991,32, 91; Q. Chen et al., *Tetrahedron Lett.* 1991,32, 7689).

For example, nitro groups can be reduced to amino groups by means of various reducing agents, such as sulfides, dithionites, complex hydrides or by catalytic hydrogenation. A reduction of a nitro group may also be carried out at a later stage of the synthesis of a compound of the formulae I and Ia, and a reduction of a nitro group to an amino group may also occur simultaneously with a reaction performed on another functional group, for example when reacting a group like a cyano group with hydrogen sulfide or when hydrogenating a group. In order to introduce the residues $R^{1a}$, $R^{1b}$ in formula 2, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the pyrrole nucleus can be hydrolyzed to the corresponding carboxylic acids (or, in the case of occasionally substituted or unsubstituted benzyl esters transformed to the corresponding carboxylic acids by hydrogenation methods), which after activation can then be reacted with amines or alcohols under standard conditions to give amides or alcohols, respectively. Ester groups present in the pyrrole nucleus can be converted to other esters by transesterification. Carboxylic acids attached to a suitable pyrrole nucleus can also be alkylated to give esters. Ether groups present at the pyrrole nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{87}$ or $R^{8'}$ in formulae 2 and 3 attached to the pyrrole ring system by application of parallel synthesis methodology, a variety of reactions can be extremely useful, including, for example, palladium, nickel or copper catalysis. Such reactions are described for example in F. Diederich, P. Stang, "*Metal-catalyzed Cross-coupling Reactions*", Wiley-VCH, 1998; or M. Beller, C. Bolm, "*Transition Metals for Organic Synthesis*", Wiley-VCH, 1998; J. Tsuji, "*Palladium Reagents and Catalysts*", Wiley, 1996; J. Hartwig, *Angew. Chem.* 1998, 110, 2154; B. Yang, S. Buchwald, *J. Organomet. Chem.* 1999, 576,125; P. Lam, C. Clark, S. Saubern, J. Adams, M. Winters, D. Chan, A. Combs, *Tetrahedron Lett.* 1998, 39, 2941; D. Chan, K. Monaco, R. Wang, M. Winters, *Tetrahedron Lett.* 1998, 39, 2933; J. Wolfe, H. Tomori, J. Sadight, J. Yin, S. Buchwald, *J. Org. Chem.* 2000, 65,1158; V. Farina, V. Krishnamurthy, W. Scott, "*The Stille Reaction*", Wiley, 1994; S. Buchwald et al., *J. Am. Chem. Soc* 2001, 123, 7727; S. Buchwald et al., *Org. Lett.* 2002, 4, 581.

The previously-mentioned reactions for the conversion of functional groups are furthermore, in general, extensively described in textbooks of organic chemistry like M. Smith, J. March, "*March's Advanced Organic Chemistry*", Wiley-VCH, 2001 and in treatises like Houben-Weyl, "*Methoden der Organischen Chemie*" (*Methods of Organic Chemistry*), Georg Thieme Verlag, Stuttgart, Germany, or "*Organic Reactions*", John Wiley & Sons, New York, or R. C. Larock, "*Comprehensive Organic Transformations*", Wiley-VCH, $2^{nd}$ ed 1999, B. Trost, I. Fleming (eds.) "*Comprehensive Organic Synthesis*", Pergamon, 1991; A. Katritzky, C. Rees, E. Scriven, "*Comprehensive Heterocyclic Chemistry II*", Elsevier Science, 1996) in which details on the reactions and primary source literature can be found. Due to the fact that in the present case the functional groups are attached to an pyrrole ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding out suitable reaction variants and reaction conditions in such cases does not cause any problems for one skilled in the art.

The structural elements present in the residues attached at the 1-position of the pyrrole ring in the compounds of the formulae I and Ia and in the $COR^{8'}$ group present in the 2-position and/or in the 3,4 and/or 5-position of the pyrrole ring can be introduced into the starting pyrrole derivative obtainable as outlined above by consecutive reaction steps using synthesis methodologies like those outlined below using procedures which per se are well known to one skilled in the art.

The residues $R^{8'}$ that can be introduced in formula 2, for example, by condensing a corresponding carboxylic acid of the formula 2 with a compound of the formula $HR^{8'}$, i.e. with an amine of the formula $HN(R^{1'})$—V—G—M to give a compound of the formula 3. The compound of the formula 3 thus obtained can already contain the desired final groups, i.e. the groups $R^{8'}$ and $R^{87}$ can be the groups —$N(R^{1'})$—V—G—M and $R^0$—Q— as defined in the formulae I and Ia, or optionally in the compound of the formula 3 thus obtained subsequently the residue or the residues $R^{8'}$ and the residue $R^{87}$ are converted into the residues —$N(R^1)$—V—G—M and $R^0$—Q—, respectively, to give the desired compound of the formulae I and Ia.

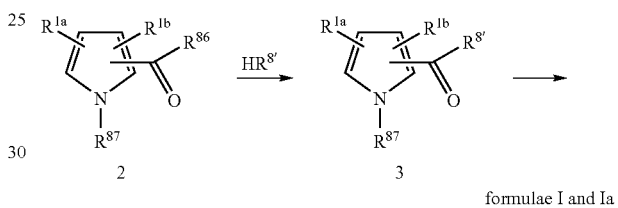

formulae I and Ia

Thus, the residues $R^{8'}$ and the residues $R^{8'}$ and —V—G—M contained therein can have the denotations of $R^1$ and —V—G—M, respectively, given above or in addition in the residues $R^{1'}$ and —V—G—M functional groups can also be present in the form of groups that can subsequently be transformed into the final groups $R^1$ and —V—G—M, i.e. functional groups can be present in the form of precursor groups or of derivatives, for example in protected form. In the course of the preparation of the compounds of the formulae I and Ia, it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, T. W. Greene and P. G. M. Wuts, "*Protective Groups in Organic Synthesis*", $3^{rd}$ ed., Wiley, 1999, or P. Kocienski, "Protecting Groups", Thieme, 1994). As examples of precursor groups cyano groups and nitro groups may be mentioned. The cyano group can in a later step be transformed into carboxylic acid derivatives or by reduction into aminomethyl groups, or the nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (K. Burgess (ed.), "*Solid Phase Organic Synthesis*", New York, Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{87}$ in the compounds of the formulae 2 and 3 can denote the group —Q—$R^0$ as defined above which finally is to be present in the desired target molecule of the formulae I and Ia, or it can denote a group which can subsequently be transformed into the group —Q—$R^0$, for example a precursor group or a derivative of the group —Q—$R^0$ in which functional groups are present in protected form, or $R^{87}$ can denote a hydrogen atom or a protective group for the nitrogen atom of the pyrrole ring. Similarly, the residues $R^{1a}$ and $R^{1b}$ in the formula 2 and 3 have the corresponding definitions of R4, and $R^3$ in formulae I and Ia as defined above, however, for the synthesis of the compounds of the formulae I and Ia these residues, too, can in principle be present at the stage of the condensation of a compound of the formula 2 with a compound of the formula $HR^{8'}$ giving a compound of the formula 3 in the form of precursor groups or in protected form.

The residues $R^{86}$ in the compounds of the formula 2 which can be identical or different, can be, for example, hydroxy or $(C_1-C_4)$-alkoxy, i.e., the groups $COR^{86}$ present in the compounds of the formula 2 can be, for example, the free carboxylic acids or esters thereof like alkyl esters as can be the groups $COR^{8'}$ in the compounds of the formulae I and Ia. The groups $COR^{86}$ can also be any other activated derivative of a carboxylic acid which allows amide formation, ester formation or thioester formation with a compound of the formula $HR^{8'}$. The group $COR^{86}$ can be, for example, an acid chloride, an activated ester like a substituted phenyl ester or an N-hydroxysuccinimide or a hydroxybenzotriazole ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula $HR^{8'}$ under standard conditions. A carboxylic acid group COOH representing $COR^{86}$ in a compound of the formula 2 can be obtained, for example, from an ester group introduced into the pyrrole system during a pyrrole synthesis by standard hydrolysis procedures. It can also be obtained, for example, by hydrolysis of a nitrile group introduced into the pyrrole system during a pyrrole sysnthesis.

Compounds of the formulae I and Ia in which a group $COR^{8'}$ is an ester group can also be prepared from compounds of the formula 2 in which $COR^{86}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formulae I and Ia in which a group $COR^{8'}$ is an amide group can be prepared from amines and compounds of the formula 2 in which $COR^{86}$ is a carboxylic acid group or an ester thereof by common amination reactions. Especially for the preparation of amides the compounds of the formula 2 in which $COR^{86}$ is a carboxylic acid group can be condensed under standard conditions with compounds of the formula $HR^{8'}$ which are amines by means of common coupling reagents used in peptide synthesis. Such coupling reagents are, for example, carbodiimides like dicyclohexylcarbodiimide (DCC), N-(3-dimethylamino-propyl)-N'-ethyl-carbodiimide (EDCI) or diisopropylcarbodiimide, carbonyldiazoles like carbonyldiimidazole (CDI) and similar reagents, propylphosphonic an hydride, O-((cyano-(ethoxycarbonyl)-methylene)amino)-N,N,N',N'-tetramethyl uronium tetrafluoroborate (TOTU), diethylphosphoryl cyanide (DEPC), bromotripyrrolidinophosphonium hexafluorophosphate (PyBroP) or bis-(2-oxo-3-oxazolidinyl)-phosphoryl chloride (BOP-Cl) and many others.

If the residue —Q—$R^0$ present in an pyrrole of the formulae I and Ia or the residue $R^{87}$ present in a pyrrole of the formula 2, or a residue in which functional groups within the residue —Q—$R^0$ or $R^{87}$ are present in protected form or in the form of a precursor group, have not already been introduced during a preceding step, for example during a synthesis of the pyrrole nucleus, these residues can, for example, be introduced into the 1-position of the pyrrole system by conventional literature procedures well known to one skilled in the art for N-alkylation, reductive amination, N-arylation, N-acylation or N-sulfonylation of ring nitrogen atoms of heterocycles. The starting pyrrole derivative that is to be employed in such a reaction carries a hydrogen atom in the 1-position. N-Alkylation of a ring nitrogen atom can, for example, be performed under standard conditions, preferably in the presence of a base like $K_2CO_3$, $Cs_2CO_3$, NaH, KOH or KOtBu, using an alkylating compound of the formula LG—Q—$R^0$ or of the formula $R^{87}$—LG, wherein the atom in the group Q or in the group $R^{87}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated in a well-known Mitsunobu reaction by a conventional activating agent.

For the preparation of compounds in which A is a direct linkage and an aromatic group is directly bonded to the 1-position of the imidazole system, conventional arylation procedures can be used. For example aryl fluorides like alkyl fluorobenzoates or 4-fluorophenyl methyl sulfones can be employed as arylating agents. Such processes are described, for example, by M. Yamada et al. J. Med. Chem. 1996, 39, 596; J. Ohmori et al. J. Med. Chem. 1996, 39, 3971. Alternatively a wide variety of substituted aryl iodides, aryl bromides or aryl triflates can serve as arylating agents at the 1-position of the heterocyclic nitrogen in a copper salt or palladium mediated reaction according for example to P. Cozzi et al. Farmaco 1987, 42, 205; P. Unangst, D. Connor, R. Stabler, R. Weikert, J. Heterocycl. Chem. 1987, 24, 811; G. Tokmakov, I. Grandberg, Tetrahedron 1995, 51,2091; D. Old, M. Harris, S. Buchwald, Org. Lett. 2000, 2, 1403, G. Mann, J. Hartwig, M. Driver, C. Fernandez-Rivas, J. Am. Chem. Soc. 1998,120, 827; J. Hartwig, M. Kawatsura, S. Hauk, K. Shaughnessy, L. J. Org. Chem. 1999, 64, 5575; S. Buchwald et al., J. Am. Chem. Soc. 2001,123, 7727. Moreover such arylations can also be accomplished by reaction of a wide range of substituted aryl boronic acids as demonstrated for example by W. Mederski, M. Lefort, M. Germann, D. Kux, Tetrahedron 1999, 55,12757; J. Collman et al., J. Org. Chem. 2001, 66, 7892. Preferred methods include, but are not limited to those described in the examples.

The compounds of the present invention are serine protease inhibitors, which inhibit the activity of the blood coagulation enzyme factors Xa and/or factor VIIa. In particular, they are highly active inhibitors of factor Xa. They are specific serine protease inhibitors inasmuch as they do not substantially inhibit the activity of other proteases whose inhibition is not desired. The activity of the compounds of the formulae I and Ia can be determined, for example, in the assays described below or in other assays known to those skilled in the art. With respect to factor Xa inhibition, a preferred embodiment of the invention comprises compounds which have a Ki<1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa and/or factor VIIa the compounds of the formulae I and Ia and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formulae I and Ia and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

The present invention also relates to the compounds of the formulae I and Ia and/or their physiologically tolerable salts and/or their prodrugs for use as pharmaceuticals (or medicaments), to the use of the compounds of the formulae I and Ia and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formulae I and Ia and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formulae I and Ia and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer. The compounds of the present invention can also be used to reduce an inflammatory response. Examples of specific disorders for the treatment or prophylaxis of which the compounds of the formulae I and Ia can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formulae I and Ia and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formulae I and Ia and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I and Ia and/or their physiologically tolerable salts and/or their prodrugs. The amount of the active ingredient of the formulae I and Ia and/or its physiologically tolerable salts and/or its prodrugs in the pharmaceutical preparations normally is from about 0.5 mg to about 1000 mg, preferably from about 1 mg to about 500 mg.

In addition to the active ingredients of the formulae I and Ia and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I and Ia, and/or their physiologically tolerable salts and/or their prodrugs. In case a pharmaceutical preparation contains two or more compounds of the formulae I and Ia, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I and Ia allows a great deal of control over the biological and physico-chemical properties of the compounds and thus allows the selection of such desired compounds. Furthermore, in addition to at least one compound of the formulae I and Ia and/or a physiologically tolerable salt and/or its prodrug, the pharmaceutical preparations can also contain one or more other therapeutically or prophylactically active ingredients.

When using the compounds of the formulae I and Ia the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I and Ia can also advantageously be used as an anticoagulant outside an individual. For example, an effective amount of a compound of the invention can be contacted with a freshly drawn blood sample to prevent coagulation of the blood sample. Further, a compound of the formulae I and Ia or its salts can be used for diagnostic purposes, for example in in vitro diagnoses, and as an auxiliary in biochemical investigations. For example, a compound of the formulae I and Ia can be used in an assay to identify the presence of factor Xa and/or factor VIIa or to isolate factor Xa and/or factor VIIa in a substantially purified form. A compound of the invention can be labeled with, for example, a radioisotope, and the labeled compound bound to factor Xa and/or factor VIIa is then detected using a routine method useful for detecting the particular label. Thus, a compound of the formulae I and Ia or a salt thereof can be used as a probe to detect the location or amount of factor Xa and/or factor VIIa activity in vivo, in vitro or ex vivo.

Furthermore, the compounds of the formulae I and Ia can be used as synthesis intermediates for the preparation of other compounds, in particular of other pharmaceutical active ingredients, which are obtainable from the compounds of the formulae I and Ia, for example by introduction of substituents or modification of functional groups. The general synthetic sequences for preparing the compounds useful in the present invention our outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention. It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Abbreviations used:

| | |
|---|---|
| $NEt_3$ | triethyl amine |
| $Bu_4NI$ | tetra-n-butylammonium iodide |
| $Cs_2CO_3$ | cesium carbonate |
| DCM | dichloromethane |
| DIEA | ethyl-diisopropyl-amine |
| DME | 1,2-dimethoxy-ethane |
| DMF | N,N-dimethylformamide |
| EDCl | N-(3-Dimethylamino-propyl)-tripyrrolidinophosphonium N'-ethyl-carbodiimide |
| HATU | [dimethylamino-([1,2,3]triazolo[4,5-b] pyridin-3-yloxy)-methylene]-dimethyl-ammonium hexafluoro phosphate |
| HOAt | 1-hydroxy-7-azabenzotriazole ([1,2,3]triazolo[4,5-b]pyridin-1-ol) |
| HPLC | high pressure liquid chromatography |
| LiOH | lithium hydroxide |
| MeOH | methanol |
| MTBE | tert-butyl methyl ether (2-methoxy-2-methyl-propane) |
| NBS | N-bromosuccinimide |
| NCS | N-chlorosuccinimide |
| NIS | N-iodosuccinimide |
| $POCl_3$ | phosphorus oxychloride |
| PyBroP | bromo-hexafluorophosphate |
| RT | room temperature |
| TFA | trifluoroacetic acid |
| THF | tetrahydrofuran |

Example 1

1-[5-(5-Chloro-thiophen-2-yl)-isoxazol-3-ylmethyl]-1H-pyrrol e-2-carboxylic acid (1-isopropyl-piperidin-4-yl)-amide (i) 1-[5-(5-Chloro-thiophen-2-yl)-isoxazol-3-ylmethyl]-1H-pyrrole-2-carboxylic acid ethyl ester To a solution of 1H-pyrrole-2-carboxylic acid ethyl ester (70 mg) in MeCN was added 3-bromomethyl-5-(5-chloro-thiophen-2-yl)-isoxazole (139 mg), $Cs_2CO_3$ (180 mg), $Bu_4NI$ (2 mg) and hexa-n-decyltri-n-butyl phosphonium bromide (10 mg). The mixture was stirred for 4 h at 60° C., whereupon it was cooled to RT and concentrated in vacuo. The residue was partitioned between water and ethyl acetate. The layers were separated and the aqueous phase was extracted with ethyl acetate. The combined organic phases were dried over anhydrous MgSO$_4$ and concentrated in vacuo to provide 1-[5-(5-chloro-thiophen-2-yl)-isoxazol-3-ylmethyl]-1H-pyrrole-2-carboxylic acid ethyl ester (169 mg) which was directly used in the next step. MS (ESI+): m/e 337 [M+H]$^+$, chloro pattern.

(ii) 1-[5-(5-Chloro-thiophen-2-yl)-isoxazol-3-ylmethyl]-1H-pyrrole-2-carboxylic acid To a solution of 1-[5-(5-chloro-thiophen-2-yl)-isoxazol-3-ylmethyl]-1H-pyrrole-2-carboxylic acid ethyl ester (135 mg) in MeOH/THF/H$_2$O (3:1:1, 5 mL) was added LiOH monohydrate (100 mg). The mixture was refluxed for 2 h after which it was cooled to RT and concentrated. The mixture was acidified by the addition of 1 N aqueous KHSO$_4$ solution and extracted with ethyl acetate. The combined organic phases were dried (MgSO$_4$) and concentrated in vacuo to provide crude 1-[5-(5-chloro-thiophen-2-yl)-isoxazol-3-ylmethyl]-1H-pyrrole-2-carboxylic acid (148 mg) which was directly used in the next step. MS (ESI−): m/e=307 [M−H]$^-$, chloro pattern.

(iii) 1-[5-(5-Chloro-thiophen-2-yl)-isoxazol-3-ylmethyl]-1H-pyrrole-2-carboxylic acid (1-isopropyl-piperidin-4-yl)-amide To 1-[5-(5-chloro-thiophen-2-yl)-isoxazol-3-ylmethyl]-1H-pyrrole-2-carboxylic acid (62 mg) in DCM (5 mL) was added HOAt (27 mg), EDCI hydrochloride (38 mg) and DIEA (106 µL). The mixture was stirred for 30 min at RT. 1-Isopropyl-piperidin-4-ylamine dihydrochloride (47 mg) and DME (1 mL) were added and stirring was continued for 16 h at RT. The mixture was concentrated in vacuo and the residue was purified by preparative HPLC. The fractions containing the product were evaporated to provide 66 mg of 1-[5-(5-chloro-thiophen-2-yl)-isoxazol-3-ylmethyl]-1H-pyrrole-2-carboxylic acid (1-isopropyl-piperidin-4-yl)-amide as its trifluoroacetate salt, MS (ESI+): m/e 433 [M+H]$^+$, chloro pattern.

Example 2

1-(3-Methoxy-benzyl)-1H-pyrrole-2-carboxylic acid (1-isopropyl-piperidin-4-yl)-amide Following the procedure from example 1 replacing 3-bromomethyl-5-(5-chloro-thiophen-2-yl)-isoxazole by 1-bromomethyl-3-methoxy-benzene in step (i), 1-(3-methoxy-benzyl)-1H-pyrrole-2-carboxylic acid (1-isopropyl-piperidin-4-yl)-amide was isolated after HPLC purification of the crude reaction mixture as its trifluoroacetate salt. MS (ESI+): m/e=356 [M+H]$^+$.

Example 3

1-[5-(5-Chloro-thiophen-2-yl)-isoxazol-3-ylmethyl]-4-nitro-1H-pyrrole-2-carboxylic acid (1-isopropyl-piperidin-4-yl)-amide Following the procedure from example 1 replacing 1H-pyrrole-2-carboxylic acid ethyl ester by 4-nitro-1H-pyrrole-2-carboxylic acid ethyl ester in step (i), 1-[5-(5-chloro-thiophen-2-yl)-isoxazol-3-ylmethyl]-4-nitro-1H-pyrrole-2-carboxylic acid (1-isopropyl-piperidin-4-yl)-amide was isolated after HPLC purification of the crude reaction mixture as its trifluoroacetate salt. MS (ESI+): m/e 478 [M+H]$^+$, chloro pattern.

Example 4

1-[5-(5-Chloro-thiophen-2-yl)-isoxazol-3-ylmethyl]-3,5-dimethyl-1H-pyrrole-2-carboxylic acid (1-isopropyl-piperidin-4-yl)-amide Following the procedure from example 1 replacing 1H-pyrrole-2-carboxylic acid ethyl ester by 3,5-dimethyl-1H-pyrrole-2-carboxylic acid ethyl ester in step (i), 1-[5-(5-chloro-thiophen-2-yl)-isoxazol-3-ylmethyl]-3,5-dimethyl-1H-pyrrole-2-carboxylic acid (1-isopropyl-piperidin-4-yl)-amide was isolated after HPLC purification of the crude reaction mixture as its trifluoroacetate salt. MS (ESI+): m/e 461 [M+H]$^+$, chloro pattern.

Example 5

1-[(5-Chloro-pyridin-2-yl carbamoyl)-methyl]-4-(perhydro-1,4-oxazepine-4-carbonyl)-1H-pyrrole-2-carboxylic acid (1-isopropyl-piperidin-4-yl)-amide (i) 4-Formyl-1H-pyrrole-2-carboxylic acid methyl ester and 5-formyl-1H-pyrrole-2-carboxylic acid methyl ester Both formyl-pyrrole derivatives were prepared adopting a procedure described by C. Schmuck, *Tetrahedron* 2001, 57, 3063: To DMF (1.61 g) was added POCl$_3$ (3.37 g) dropwise under Ar at 0° C. The mixture was allowed to warm to RT after which it was diluted with DCM (11 mL). A solution of 1H-pyrrole-2-carboxylic acid methyl ester (2.51 g) in DCM (11 mL) was added dropwise. The mixture was refluxed for 30 min whereupon it was cooled to 10° C. and quenched with a solution of potassium acetate (10.8 g) in water (28 mL). The phases were separated and the aqueous layer was extracted with MTBE. The combined organic phases were washed with saturated aqueous K$_2$CO$_3$ solution and concentrated in vacuo. The residue was purified by flash column chromatography on silica (ethyl acetate/heptane 1:5) to yield 4-formyl-1H-pyrrole-2-carboxylic acid methyl ester (589 mg) and 5-formyl-1H-pyrrole-2-carboxylic acid methyl ester (1.60 g) as solids.

(ii) 1H-Pyrrole-2,4-dicarboxylic acid 2-methyl ester

To a solution of 4-formyl-1H-pyrrole-2-carboxylic acid methyl ester (589 mg) in acetone/water (50 mL, 1:1) was added a solution of KMnO$_4$ in acetone/water (70 mL, 1:1) dropwise within one hour. The mixture was stirred for 3 h at RT whereupon it was poured into a solution of NaHSO$_3$ (10% in 1 N HCl, 100 mL). The resulting mixture was extracted with ethyl acetate. The combined organic phases were washed with water and extracted with 2N aqueous K$_2$CO$_3$ solution. The basic aqueous phase was acidified with 2N HCl and extracted with ethyl acetate The combined organic phases were dried (MgSO$_4$) and concentrated in vacuo to provide 1H-pyrrole-2,4-dicarboxylic acid 2-methyl ester (530 mg) which was used directly in the next step.

(iii) 4-([1,4]Oxazepane-4-carbonyl)-1H-pyrrole-2-carboxylic acid ethyl ester To 1H-pyrrole-2,4-dicarboxylic acid 2-methyl ester (291 mg) in DCM (18 mL) was added [1,4]oxazepane hydrochloride (236 mg), PyBroP (802 mg) and DIEA (878 μL). The mixture was stirred for 3 h at RT after which it was washed with saturated aqueous NaHCO$_3$ solution and 1 N HCl. The organic phase was dried (MgSO$_4$) and concentrated in vacuo. The residue was purified by flash column chromatography on silica (ethyl acetate) to provide 4-([1,4]oxazepane-4-carbonyl)-1H-pyrrole-2-carboxylic acid ethyl ester (533 mg). This material was used directly used in the next step although traces of phosphine oxide impurities resulting from the coupling reagent were still present.

(iv) 4-([1,4]oxazepane-4-carbonyl)-1H-pyrrole-2-carboxylic acid

To a solution of the foregoing ester (434 mg) in ethanol (16 mL) was added 1 N NaOH (1.82 mL). The mixture was stirred for two days at room temperature, concentrated, acidified with 2N HCl and extracted with ethyl acetate. The combined organic phases were dried over anhydrous MgSO$_4$ and concentrated in vacuo to provide crude 4-([1,4]Oxazepane-4-carbonyl)-1H-pyrrole-2-carboxylic acid (293 mg) which was directly used in the next step.

(v) 4-([1,4]oxazepane-4-carbonyl)-1H-pyrrol e-2-carboxylic acid (1-isopropyl-piperidin-4-yl)-amide To the foregoing carboxylic acid (293 mg) in DCM (10 mL) was added HOAt (167 mg), EDCI hydrochloride (236 mg) and DIEA (627 μL). The mixture was stirred for 30 min at RT. 1-Isopropyl-piperidin-4-ylamine dihydrochloride (265 mg) was added and stirring was continued for 16 h at RT. The reaction mixture was washed with 2N NaOH and concentrated. The residue was purified by flash column chromatography on silica (ethyl acetate/MeOH/NEt$_3$ 20:2:1) to provide 4-([1,4]oxazepane-4-carbonyl)-1H-pyrrole-2-carboxylic acid (1-isopropyl-piperidin-4-yl)-amide (72 mg), MS (ESI+): m/e=363 [M+H]$^+$.

(vi) 1-[(5-Chloro-pyridin-2-yl carbamoyl)-methyl]-4-(perhydro-1,4-oxazepine-4-carbonyl)-1H-pyrrole-2-carboxylic acid (1-isopropyl-piperidin-4-yl)-amide To the foregoing pyrrole (72 mg) in anhydrous DMF (2.5 mL) was added NaH (20 mg, 60% in mineral oil). The mixture was stirred for 30 min at RT. A solution of 2-bromo-N-(5-chloro-pyridin-2-yl)-acetamide (49 mg) in DMF (0.5 mL) was added dropwise and stirring was continued for 5 h at RT. The mixture was quenched by dropwise addition of acetic acid after which it was concentrated. The residue was purified by preparative HPLC. The fractions containing the product were evaporated to provide 11 mg of 1-[(5-chloro-pyridin-2-ylcarbamoyl)-methyl]-4-(perhydro-1,4-oxazepine-4-carbonyl)-1H-pyrrol e-2-carboxyl i c acid (1-isopropyl-piperidin-4-yl)-amide as its trifluoroacetate salt, MS (ESI+): m/e=531 [M+H]$^+$, chloro pattern.

Example 6

1-[(5-Chloro-pyridin-2-yl carbamoyl)-methyl]-5-(perhydro-1,4-oxazepine-4-carbonyl)-1H-pyrrole-2-carboxylic acid (1-isopropyl-piperidin-4-yl)-amide

(i) 1H-Pyrrole-2,5-dicarboxylic acid 2-methyl ester was prepared according to the procedure described in example 5, step (ii) using 5-formyl-1H-pyrrole-2-carboxylic acid

(ii) 5-(1-Isopropyl-piperidin-4-ylcarbamoyl)-1H-pyrrole-2-carboxylic acid ethyl ester To the foregoing carboxylic acid (845 mg) in DCM (50 mL) was added HOAt (680 mg), EDCI hydrochloride (960 mg) and DIEA (2.55 mL). The mixture was stirred for 30 min at RT. 1-Isopropyl-piperidin-4-ylamine dihydrochloride (1.08 g) was added and stirring was continued for 16 h at RT. The reaction mixture was washed with saturated aqueous KHCO$_3$ solution and water and concentrated in vacuo to yield 1.05 g of 5-(1-isopropyl-piperidin-4-ylcarbamoyl)-1H-pyrrole-2-carboxylic acid ethyl ester which was directly used in the next step.

(iii) Sodium 5-(1-isopropyl-piperidin-4-ylcarbamoyl)-1H-pyrrole-2-carboxylate The foregoing ester was dissolved in ethanol (33 mL) and 1 N NaOH (3.58 mL). The solution was stirred for 3 days at RT and concentrated in vacuo to give crude sodium 5-(1-isopropyl-piperidin-4-ylcarbamoyl)-1H-pyrrole-2-carboxylate (1.05 g) which was used without further purification.

(iv) 5-([1,4]oxazepane-4-carbonyl)-1H-pyrrol e-2-carboxylic acid (1-isopropyl-piperidin-4-yl)-amide was prepared by a carbodiimide mediated coupling according to example 5, step (v) using the foregoing carboxylate and [1,4]oxazepane hydrochloride as reactants

(v) 1-[(5-Chloro-pyridin-2-ylcarbamoyl)-methyl]-5-(perhydro-1,4-oxazepine-4-carbonyl)-1H-pyrrole-2-carboxylic acid (1-isopropyl-piperidin-4-yl)-amide Following the procedure from example 5 replacing 4-([1,4]Oxazepane-4-carbonyl)-1H-pyrrole-2-carboxylic acid (1-isopropyl-piperidin-4-yl)-amide by 5-([1,4]Oxazepane-4-carbonyl)-1H-pyrrole-2-carboxylic acid (1-isopropyl-piperidin-4-yl)-amide in step (vi), 1-[(5-chloro-pyridin-2-ylcarbamoyl)-methyl]-5-(perhydro-1,4-oxazepine-4-carbonyl)-1H-pyrrole-2-carboxylic acid (1-isopropyl-piperidin-4-yl)-amide was isolated after HPLC purification of the crude reaction mixture as its trifluoroacetate salt. MS (ESI+): m/e=531 [M+H]$^+$, chloro pattern.

Example 7

1-[5-(5-Chloro-thiophen-2-yl)-isoxazol-3-ylmethyl]-5-(perhydro-1,4-oxazepine-4-carbonyl)-1H-pyrrole-2-carboxylic acid (1-isopropyl-piperidin-4-yl)-amide Following the procedure from example 6 replacing 2-bromo-N-(5-chloro-pyridin-2-yl)-acetamide by 3-bromomethyl-5-(5-chloro-thiophen-2-yl)-isoxazole in step (v), 1-[5-(5-chloro-thiophen-2-yl)-isoxazol-3-ylmethyl]-5-(perhydro-1,4-oxazepine-4-carbonyl)-1H-pyrrol e-2-carboxylic acid (1-isopropyl-piperidin-4-yl)-amide was isolated as its trifluoroacetate salt after HPLC purification of the crude reaction mixture. MS (ESI+): m/e=560 [M+H]$^+$, chloro pattern.

Example 8

3-[1-[5-(5-Chloro-thiophen-2-yl)-isoxazol-3-ylmethyl]-5-(1-isopropyl-piperidin-4-ylcarbamoyl)-2,4-dimethyl-1H-pyrrol-3-yl]-propionic acid (i) 4-(2-Methoxycarbonyl-ethyl)-3,5-dimethyl-1H-pyrrole-2-carboxylic acid 4-(2-methoxycarbonyl-ethyl)-3,5-dimethyl-1H-pyrrole-2-carboxylic acid benzyl ester (390 mg, 1.24 mmol) was dissolved in anhydrous MeOH (20 mL). The solution was evacuated and rinsed with argon several times. 120 mg of palladium on charcoal (10%) were added and again the mixture was evacuated and rinsed with argon several times. Finally argon was exchanged by hydrogen (balloon filled with hydrogen) and the mixture was stirred for 3 h at room temperature. The reaction mixture was filtered over celite and the filter residue was washed with MeOH (150 mL). The filtrate was concentrated in vacuo to give pure 4-(2-methoxycarbonyl-ethyl)-3,5-dimethyl-1H-pyrrole-2-carboxylic acid as a colorless solid (263 mg). MS (ESI−): m/e=225 [M−H]−.

(ii) 3-[5-(1-Isopropyl-piperidin-4-ylcarbamoyl)-2,4-dimethyl-1H-pyrrol-3-yl]-propionic acid methyl ester 263 mg of (1.17 mmol) 4-(2-methoxycarbonyl-ethyl)-3,5-dimethyl-1H-pyrrole-2-carboxylic acid were dissolved in DMF (10 mL). 488.4 mg (1.28 mmol) of HATU and DIEA (224 µl) were added and the resulting mixture was stirred for 45 minutes at RT. A solution of 276.3 mg (1.28 mmol) of 1-isopropyl-piperidine-4-ylamine-dihydrochloride and 448 µl of DIEA was added. The reaction mixture was stirred over night after which it was concentrated. The residue was diluted with DCM and washed with a saturated $NaHCO_3$ solution and brine. The organic layer was dried over $MgSO_4$ and concentrated. Preparative HPLC($CH_3CN/H_2O$ gradient+0.05% formic acid) gave pure 3-[5-(1-isopropyl-piperidin-4-ylcarbamoyl)-2,4-dimethyl-1H-pyrrol-3-yl]-propionic acid methyl ester (166 mg) as a colorless amorphous material. MS (ESI+): m/e=351 [M+H]+.

(iii) 3-[1-[5-(5-Chloro-thiophen-2-yl)-isoxazol-3-ylmethyl]-5-(1-isopropyl-piperidin-4-ylcarbamoyl)-2,4-dimethyl-1H-pyrrol-3-yl]-propionic acid methyl ester 55 mg (0.16 mmol) of 3-[5-(1-isopropyl-piperidin-4-ylcarbamoyl)-2,4-dimethyl-1H-pyrrol-3-yl]-propionic acid methyl ester were dissolved in DMF (5 mL). Subsequently 103 mg (2 equiv.) of $Cs_2CO_3$ and 65.8 mg (1.5 equiv.) of 3-bromomethyl-5-(5-chloro-thiophen-2-yl)-isoxazole were added and the resulting mixture was stirred for 4 h at 800 C. Because of low conversion 206 mg (4 equiv.) of $Cs_2CO_3$ were added stirring was continued for 7 h at 80° C. The reaction mixture was acidified by the addition of acetic acid and concentrated. The residue was purified by preparative HPLC ($CH_3CN/H_2O$ gradient+0.05% formic acid) to give 3-[1-[5-(5-chloro-thiophen-2-yl)-isoxazol-3-ylmethyl]-5-(1-isopropyl-piperidin-4-ylcarbamoyl)-2,4-dimethyl-1H-pyrrol-3-yl]-propionic acid methyl ester (34 mg) as a colorless amorphous material. MS (ESI+): m/e=548 [M+H]+, chloro pattern.

(iv) 3-[1-[5-(5-Chloro-thiophen-2-yl)-isoxazol-3-ylmethyl]-5-(1-isopropyl-piperidin-4-ylcarbamoyl)-2,4-dimethyl-1H-pyrrol-3-yl]-propionic acid To 34 mg (0.06 mmol) of 3-[1-[5-(5-chloro-thiophen-2-yl)-isoxazol-3-ylmethyl]-5-(1-isopropyl-piperidin-4-ylcarbamoyl)-2,4-dimethyl-1H-pyrrol-3-yl]-propionic acid methyl ester in MeOH (4 mL) 1 M aqueous LiOH-solution (0.3 mL) was added and the resulting mixture was stirred at 60° C. for 5 h. The mixture was acidified by the addition of a 1 M HCl-solution (pH 5) and concentrated under reduced pressure. Final purification by preparative HPLC($CH_3CN/H_2O$ gradient+0.05% formic acid) gave pure 3-[1-[5-(5-chloro-thiophen-2-yl)-isoxazol-3-ylmethyl]-5-(1-isopropyl-piperidin-4-ylcarbamoyl)-2,4-dimethyl-1H-pyrrol-3-yl]-propionic acid as a colorless amorphous material. The product was obtained as its hydroformiate (11 mg). MS (ESI+): m/e=534 [M+H]+, chloro pattern.

Example 9

1-[5-(5-Chloro-thiophen-2-yl)-isoxazol-3-ylmethyl]-5-(1-isopropyl-piperidin-4-yl carbamoyl)-1H-pyrrole-2-carboxylic acid benzyl ester (i) 5-Formyl-1H-pyrrole-2-carboxylic acid benzyl ester and 4-Formyl-1H-pyrrole-2-carboxylic acid benzyl ester To DMF (5.93 g) was added $POCl_3$ (12.45 g) dropwise at 0° C. The mixture was warmed to RT, diluted with DCM (40 mL) and cooled again to 0° C. A solution of 1H-pyrrole-2-carboxylic acid benzyl ester (15.00 g, prepared by adopting a procedure from J. Barry, G. Bram and A. Petit, *Heterocycles* 1985, 23, 875-880) in DCM (40 mL) was added dropwise at such a rate that the temperature of the reaction mixture did not rise above 0° C. The reaction was the heated to reflux for 30 min whereupon it was cooled to 10° C. A solution of sodium acetate (28g) in water (90 mL) was added carefully. After stirring for 15 min the two resulting phases were separated and the aqueous phase was washed with DCM (3×75 mL). The combined organic phases were washed with saturated $Na_2CO_3$ solution and brine, dried over $MgSO_4$ and concentrated. The residue was purified by flash column chromatography on silica (ethyl acetate/heptanes 1:2) to provide 5-formyl-1H-pyrrole-2-carboxylic acid benzyl ester (8.0 g) and 4-formyl-1H-pyrrole-2-carboxylic acid benzyl ester (4.0 g).

(ii) 1H-Pyrrole-2,5-dicarboxylic acid monobenzyl ester

To a solution of 5-formyl-1H-pyrrole-2-carboxylic acid benzyl ester (8.0 g) in n-butanol (300 mL) and water (112 mL) was added sodium dihydrogen phosphate (6.28 g), sodium chlorite (9.47 g) and isobutene (58g). The mixture was stirred for 20 h at RT after which it was concentrated. After purification of the residue by flash column chromatography on silica (DCM/MeOH 15:1 to 1:1) 10.0 g of 1H-pyrrole-2,5-dicarboxylic acid monobenzyl ester were obtained.

(iii) 5-(1-Isopropyl-piperidin-4-ylcarbamoyl)-1H-pyrrole-2-carboxylic acid benzyl ester The foregoing acid (1.72 g) in DCM (35 mL) a few drops of DMF were added followed by slow addition of oxalyl chloride (1.34 g). The mixture was heated to reflux for 3 h and then concentrated. To a solution of the resulting acid chloride in THF was added 1-isopropyl-piperidin-4-ylamine (1.00 g) and NEt$_3$ (3.89 mL) in THF (35 mL). The resulting mixture was stirred for 20 h at RT whereupon it was concentrated. The residue was partitioned between ethyl acetate and saturated aqueous NaHCO$_3$ solution. The phases were separated and the organic phase was washed with saturated aqueous NaHCO$_3$ solution and brine, dried over MgSO$_4$ and concentrated. Preparative HPLC (CH$_3$CN/H$_2$O gradient+0.05% TFA) gave 5-(1-isopropyl-piperidin-4-ylcarbamoyl)-1H-pyrrole-2-carboxylic acid benzyl ester (287 mg).

(iv) 1-[-(5-Chloro-thiophen-2-yl)-isoxazol-3-ylmethyl]-5-(1-isopropyl-piperidin-4-yl carbamoyl)-1H-pyrrole-2-carboxylic acid benzyl ester To a solution of 5-(1-isopropyl-piperidin-4-ylcarbamoyl)-1H-pyrrole-2-carboxylic acid benzyl ester (20 mg) in DMF (1 mL) was added Cs$_2$CO$_3$ (µl mg). The mixture was stirred for 30 min at RT. 3-Bromomethyl-5-(5-chloro-thiophen-2-yl)-isoxazole (15 mg) was added and stirring was continued for 20 h at RT whereupon the mixture was filtered. The filtrate was directly subjected to preparative HPLC(CH$_3$CN/H$_2$O gradient+0.05% TFA). Pure 1-[5-(5-Chloro-thiophen-2-yl)-isoxazol-3-ylmethyl]-5-(1-isopropyl-piperidin-4-ylcarbamoyl)-1H-pyrrol e-2-carboxylic acid benzyl ester (15 mg) was obtained as its trifluoroacetate salt. MS (ESI$^+$): m/e=567 [M+H]$^+$, chloro pattern.

Example 10

1-[5-(5-Chloro-thiophen-2-yl)-isoxazol-3-ylmethyl]-5-(1-isopropyl-piperidin-4-ylcarbamoyl)-1H-pyrrole-2-carboxylic acid methyl ester The product was obtained by transesterification of the product of example 9, step (iv): The crude reaction mixture from example 9, step (iv) was triturated with MeOH for a few minutes after which it was filtered and concentrated. 1-[5-(5-Chloro-thiophen-2-yl)-isoxazol-3-ylmethyl]-5-(1-isopropyl-piperidin-4-ylcarbamoyl)-1H-pyrrole-2-carboxylic acid methyl ester was obtained as its 5 trifluoroacetate salt after preparative HPLC(CH$_3$CN/H$_2$O gradient+0.05% TFA) of the residue. MS (ESI$^+$): m/e=491 [M+H]$^+$, chloro pattern.

Example 11

1-[5-(5-Chloro-thiophen-2-yl)-isoxazol-3-ylmethyl]-5-(1-isopropyl-piperidin-4-ylcarbamoyl)-1H-pyrrole-2-carboxylic acid To a solution of 1-[5-(5-Chloro-thiophen-2-yl)-isoxazol-3-ylmethyl]-5-(1-isopropyl-piperidin-4-ylcarbamoyl)-1H-pyrrole-2-carboxylic acid methyl ester (example 10, 30 mg) in 5 mL of THF/water(3:1) was added LiOH (9 mg) The mixture was stirred for 2 h at 45° C. after which it was cooled to RT, acidified with TFA and concentrated. 1-[5-(5-Chloro-thiophen-2-yl)-isoxazol-3-ylmethyl]-5-(1-isopropyl-piperidin-4-ylcarbamoyl)-1H-pyrrole-2-carboxylic acid was obtained after preparative HPLC(CH$_3$CN/H$_2$O gradient+0.05% TFA) of the residue. MS (ESI$^+$): m/e=477 [M+H]$^+$, chloro pattern.

Example 12

1-[(5-Chloro-pyridin-2-yl carbamoyl)-methyl]-4-(1-isopropyl-piperidin-4-ylcarbamoyl)-1H-pyrrole-2-carboxylic acid benzyl ester (i) 1H-Pyrrole-2,4-dicarboxylic acid 2-benzyl ester Following the procedure from example 9, step (ii) 1H-pyrrole-2,4-dicarboxylic acid 2-benzyl ester was obtained from oxidation of 4-formyl-1H-pyrrole-2-carboxylic acid benzyl ester.

(ii) 4-(1-Isopropyl-piperidin-4-ylcarbamoyl)-1H-pyrrole-2-carboxylic acid benzyl ester This compound was obtained by following the procedure from example 9, step (iii) replacing 1H-pyrrole-2,5-dicarboxylic acid monobenzyl ester by 1H-pyrrole-2,4-dicarboxylic acid 2-benzyl ester.

(iii) 1-[(5-Chloro-pyridin-2-ylcarbamoyl)-methyl]-4-(1-isopropyl-piperidin-4-ylcarbamoyl)-1H-pyrrole-2-carboxylic acid benzyl ester To a solution of 4-(1-Isopropyl-piperidin-4-ylcarbamoyl)-1H-pyrrole-2-carboxylic acid benzyl ester (50 mg) in DMF (2 mL) was added Cs$_2$CO$_3$ (176 mg), followed by 2-bromo-N-(5-chloro-pyridin-2-yl)-acetamide (34 mg). The mixture was stirred for 20 h at RT whereupon it was filtered. The filtrates were directly subjected to preparative HPLC(CH$_3$CN/H$_2$O gradient+0.05% TFA). Pure 1-[(5-chloro-pyridin-2-ylcarbamoyl)-methyl]-4-(1-isopropyl-piperidin-4-ylcarbamoyl)-1H-pyrrole-2-carboxylic acid benzyl ester (28.5 mg) was obtained as its trifluoroacetate salt. MS (ESI$^+$): m/e=538 [M+H]$^+$, chloro pattern.

Example 13

1-[5-(5-Chloro-thiophen-2-yl)-isoxazol-3-ylmethyl]-4-(1-isopropyl-piperidin-4-ylcarbamoyl)-1H-pyrrole-2-carboxylic acid benzyl ester This compound was prepared by following the procedure from example 12 replacing 2-bromo-N-(5-chloro-pyridin-2-yl)-acetamide by 3-bromomethyl-5-(5-chloro-thiophen-2-yl)-isoxazole. It was obtained as its trifluoroacetate salt after preparative HPLC(CH$_3$CN/H$_2$O gradient+0.05% TFA). MS (ESI$^+$): m/e=567 [M+H]$^+$, chloro pattern.

Example 14

1-[(5-Chloro-pyridin-2-yl carbamoyl)-methyl]-4-nitro-1H-pyrrole-2-carboxylic acid (1-isopropyl-piperidin-4-yl)-amide (i) 4-Nitro-1H-pyrrole-2-carboxylic acid (1-isopropyl-piperidin-4-yl)-amide To 4-nitro-1H-pyrrole-2-carboxylic acid (200 mg) in DCM (10 mL) was added DIEA (436 µL), HATU (487 mg) and 1-isopropyl-piperidin-4-ylamine (182 mg). The mixture was stirred for 1 h at RT after which it was concentrated. The residue was purified by preparative HPLC to give 4-nitro-1H-pyrrole-2-carboxylic acid (1-isopropyl-piperidin-4-yl)-amide as its trifluoroacetate salt (50 mg).

(ii) 1-[(5-Chloro-pyridin-2-ylcarbamoyl)-methyl]-4-nitro-1H-pyrrole-2-carboxylic acid (1-isopropyl-piperidin-4-yl)-amide To a solution of 4-nitro-1H-pyrrole-2-carboxylic acid (1-isopropyl-piperidin-4-yl)-amide trifluoroacetate salt (30 mg) in DMF (4 mL) was added $Cs_2CO_3$ (70 mg). The mixture was stirred for 30 min at RT after which 2-bromo-N-(5-chloro-pyridin-2-yl)-acetamide (27 mg) was added. Stirring was continued for 20 h at RT. The mixture was filtered and directly subjected to preparative HPLC($CH_3CN/H_2O$ gradient+0.05% TFA) to give 1-[(5-chloro-pyridin-2-ylcarbamoyl)-methyl]-4-nitro-1H-pyrrole-2-carboxylic acid (1-isopropyl-piperidin-4-yl)-amide (15 mg) as its trifluoroacetate salt. MS (ESI$^+$): m/e=449 [M+H]$^+$, chloro pattern.

Example 15

1-[(5-Chloro-pyridin-2-yl carbamoyl)-methyl]-4-(1-isopropyl-piperidin-4-yl carbamoyl)-1H-pyrrole-2-carboxylic acid methyl ester The product was obtained by transesterification of the product of example 12: The crude reaction mixture from example 12 was triturated with MeOH for a few minutes after which it was filtered and concentrated. 1-[(5-Chloro-pyridin-2-ylcarbamoyl)-methyl]-4-(1-isopropyl-piperidin-4-ylcarbamoyl)-1H-pyrrole-2-carboxylic acid methyl ester was obtained as its trifluoroacetate salt after preparative HPLC ($CH_3CN/H_2O$ gradient+0.05% TFA) of the residue. MS (ESI$^+$): m/e=462 [M+H]$^+$, chloro pattern.

Example 16

1-[5-(5-Chloro-thiophen-2-yl)-isoxazol-3-ylmethyl]-4-(1-isopropyl-piperidin-4-ylcarbamoyl)-1H-pyrrole-2-carboxylic acid methyl ester The product was obtained by transesterification of the product of example 13: The crude reaction mixture from example 13 was triturated with MeOH for a few minutes whereupon it was filtered and concentrated. 1-[5-(5-Chloro-thiophen-2-yl)-isoxazol-3-ylmethyl]-4-(1-isopropyl-piperidin-4-ylcarbamoyl)-1H-pyrrole-2-carboxylic acid methyl ester was obtained as its trifluoroacetate salt after preparative HPLC($CH_3CN/H_2O$ gradient+0.05% TFA) of the residue. MS (ESI$^+$): m/e=491 [M+H]$^+$, chloro pattern.

Example 17

1-[5-(5-Chloro-thiophen-2-yl)-isoxazol-3-ylmethyl]-4-(1-isopropyl-piperidin-4-ylcarbamoyl)-1H-pyrrole-2-carboxylic acid To a solution of 1-[5-(5-chloro-thiophen-2-yl)-isoxazol-3-ylmethyl]-4-(1-isopropyl-piperidin-4-ylcarbamoyl)-1H-pyrrole-2-carboxylic acid methyl ester (example 16, 60 mg) in 15 mL of THF/water(3:1) was added LiOH monohydrate (50 mg) The mixture was stirred for 2 h at 45° C. whereupon it was cooled to RT, acidified with TFA and concentrated. 1-[5-(5-Chloro-thiophen-2-yl)-isoxazol-3-ylmethyl]-4-(1-isopropyl-piperidin-4-ylcarbamoyl)-1H-pyrrole-2-carboxylic acid (33 mg) was obtained after HPLC purification ($CH_3CN/H_2O$ gradient+0.05% TFA) of the crude product. MS (ESI$^+$): m/e=477 [M+H]$^+$, chloro pattern.

Example 18

1-[5-(5-Chloro-thiophen-2-yl)-isoxazol-3-ylmethyl]-5-(3-methoxy-azetidine-1-carbonyl)-1H-pyrrole-2-carboxylic acid (1-isopropyl-piperidin-4-yl)-amide To a solution of 1-[5-(5-chloro-thiophen-2-yl)-isoxazol-3-ylmethyl]-4-(1-isopropyl-piperidin-4-ylcarbamoyl)-1H-pyrrole-2-carboxylic acid (example 17, 9 mg) in DCM (2 mL) was added HATU (7.2 mg), DIEA (13 µL) and 3-methoxy-azetidine. The mixture was stirred for 1 h at RT and then concentrated. The residue was purified by preparative HPLC ($CH_3CN/H_2O$ gradient+0.05% TFA) to give 1-[5-(5-Chloro-thiophen-2-yl)-isoxazol-3-ylmethyl]-5-(3-methoxy-azetidine-1-carbonyl)-1H-pyrrole-2-carboxylic acid (1-isopropyl-piperidin-4-yl)-amide (4.3 mg) as its trifluoroacetate salt. MS (ESI$^+$): m/e=546 [M+H]$^+$, chloro pattern.

Example 19

1-[5-(5-Chloro-thiophen-2-yl)-isoxazol-3-ylmethyl]-1H-pyrrole-2,5-di carboxylic acid 2-[(1-isopropyl-piperidin-4-yl)-amide] 5-[(2-methoxy-ethyl)-amide]

This compound was prepared by following the procedure described in example 18 replacing 3-methoxy-azetidine by 2-methoxy-ethylamine. 1-[5-(5-Chloro-thiophen-2-yl)-isoxazol-3-ylmethyl]-1H-pyrrole-2,5-dicarboxylic acid 2-[(1-isopropyl-piperidin-4-yl)-amide] 5-[(2-methoxy-ethyl)-amide] was obtained as its trifluoroacetate salt after HPLC purification ($CH_3CN/H_2O$ gradient+0.05% TFA) of the crude product. MS (ESI$^+$): m/e=534 [M+H]$^+$, chloro pattern.

Example 20

1-[5-(5-Chloro-thiophen-2-yl)-isoxazol-3-ylmethyl]-1H-pyrrole-2,5-dicarboxylic acid 2-[(1-isopropyl-piperidin-4-yl)-amide] 5-[(2-methoxy-ethyl)-methyl-amide]

This compound was prepared by following the procedure described in example 18 replacing 3-methoxy-azetidine by (2-Methoxy-ethyl)-methyl-amine. 1-[5-(5-Chloro-thiophen-2-yl)-isoxazol-3-ylmethyl]-1H-pyrrole-2,5-dicarboxylic acid 2-[(1-isopropyl-piperidin-4-yl)-amide] 5-[(2-methoxy-ethyl)-methyl-amide] was obtained as its trifluoroacetate salt after HPLC purification ($CH_3CN/H_2O$ gradient+0.05% TFA) of the crude product. MS (ESI$^+$): m/e=548 [M+H]$^+$, chloro pattern.

Example 21

1-[5-(5-Chloro-thiophen-2-yl)-isoxazol-3-ylmethyl]-5-phenyl-1H-pyrrole-2-carboxylic acid (1-isopropyl-piperidin-4-yl)-amide

(i) 5-Phenyl-1H-pyrrole-2-carboxylic acid (1-isopropyl-piperidin-4-yl)-amide To 1-isopropyl-piperidin-4-ylamine (350 mg) in DCM (15 mL) was added DIEA (1.67 mL), followed by HATU (935 mg) and 5-phenyl-1H-pyrrole-2-carboxylic acid (461 mg). The mixture was stirred for 1 h at RT whereupon it was washed two times with saturated aqueous $NaHCO_3$ solution, dried over $MgSO_4$ and concentrated to give crude 5-phenyl-1H-pyrrole-2-carboxylic acid (1-isopropyl-piperidin-4-yl)-amide which was used directly in the following step.

(ii) 1-[5-(5-Chloro-thiophen-2-yl)-isoxazol-3-ylmethyl]-5-phenyl-1H-pyrrol e-2-carboxylic acid (1-isopropyl-piperidin-4-yl)-amide To a solution of 5-phenyl-1H-pyrrole-2-carboxylic acid (1-isopropyl-piperidin-4-yl)-amide (50 mg) in DMF (2 mL) was added $Cs_2CO_3$ (105 mg). The mixture was stirred for 30 min at RT. 3-Bromomethyl-5-(5-chloro-thiophen-2-yl)-isoxazole (45 mg) was added and stirring was continued for 3 h at RT. The mixture was filtered and directly subjected to preparative HPLC($CH_3CN/H_2O$ gradient+0.05% TFA) to give 1-[5-(5-chloro-thiophen-2-yl)-isoxazol-3-ylmethyl]-5-phenyl-1H-pyrrole-2-carboxylic acid (1-isopropyl-piperidin-4-yl)-amide (15 mg) as its trifluoroacetate salt. MS ($ESI^+$): m/e=509 $[M+H]^+$, chloro pattern.

Example 22

1-[5-(5-Chloro-thiophen-2-yl)-isoxazol-3-ylmethyl]-3,5-dimethyl-4-(perhydro-1,4-oxazepine-4-sulfonyl)-1H-pyrrole-2-carboxylic acid (1-isopropyl-piperidin-4-yl)-amide (i) 3,5-Dimethyl-4-([1,4]oxazepane-4-sulfonyl)-1H-pyrrole-2-carboxylic acid ethyl ester To [1,4]oxazepane hydrochloride (400 mg) in DCM (45 mL) was added DIEA (2.70 mL) followed by 4-chlorosulfonyl-3,5-dimethyl-1H-pyrrole-2-carboxylic acid ethyl ester (1.05 g). The mixture was stirred for 1 h at RT after which water was added and the resulting two phases were separated. The organic phase was washed two times with saturated aqueous $NaHCO_3$ solution, dried over $MgSO_4$ and concentrated to give crude) 3,5-dimethyl-4-([1,4]oxazepane-4-sulfonyl)-1H-pyrrole-2-carboxylic acid ethyl ester (970 mg) which was used directly in the following step.

(ii) 1-[5-(5-Chloro-thiophen-2-yl)-isoxazol-3-ylmethyl]-3,5-dimethyl-4-([1,4]oxazepane-4-sulfonyl)-1H-pyrrole-2-carboxylic acid ethyl ester:

To a solution of 3,5-dimethyl-4-([1,4]oxazepane-4-sulfonyl)-1H-pyrrole-2-carboxylic acid ethyl ester (100 mg) in DMF (5 mL) was added $Cs_2CO_3$ (197 mg). The mixture was stirred for 30 min at RT after which 3-bromomethyl-5-(5-chloro-thiophen-2-yl)-isoxazole (84 mg) was added. Stirring was continued for 20 h at RT whereupon the mixture was filtered and directly subjected to preparative HPLC($CH_3CN/H_2O$ gradient+0.05% TFA) to give 1-[5-(5-chloro-thiophen-2-yl)-isoxazol-3-ylmethyl]-3,5-dimethyl-4-([1,4]oxazepane-4-sulfonyl)-1H-pyrrole-2-carboxylic acid ethyl ester (100 mg).

(iii) 1-[5-(5-Chloro-thiophen-2-yl)-isoxazol-3-ylmethyl]-3,5-dimethyl-4-([1,4]oxazepane-4-sulfonyl)-1H-pyrrole-2-carboxylic acid To a solution of [5-(5-chloro-thiophen-2-yl)-isoxazol-3-ylmethyl]-3,5-dimethyl-4-([1,4]oxazepane-4-sulfonyl)-1H-pyrrole-2-carboxylic acid ethyl ester (100 mg) in 20 mL of THF/water(3:1) was added LiOH monohydrate (200 mg) The mixture was stirred for 2h at 45° C. and for 6 h at 60° C. whereupon it was cooled to RT, concentrated, acidified with 2M HCl to pH=2 and extracted with DCM (3×30 mL). The combined organic layers were dried ($MgSO_4$) and concentrated to give crude 1-[5-(5-chloro-thiophen-2-yl)-isoxazol-3-ylmethyl]-3,5-dimethyl-4-([1,4]oxazepane-4-sulfonyl)-1H-pyrrole-2-carboxylic acid (80 mg) which was used directly in the next step.

(iv) 1-[5-(5-Chloro-thiophen-2-yl)-isoxazol-3-ylmethyl]-3,5-dimethyl-4-(perhydro-1,4-oxazepine-4-sulfonyl)-1H-pyrrole-2-carboxylic acid (1-isopropyl-piperidin-4-yl)-amide To 1-[5-(5-chloro-thiophen-2-yl)-isoxazol-3-ylmethyl]-3,5-dimethyl-4-([1,4]oxazepane-4-sulfonyl)-1H-pyrrol e-2-carboxylic acid (80 mg) in DCM (5 mL) was added DIEA (110 µL), HATU (61 mg) and 1-isopropyl-piperidin-4-ylamine (23 mg). The mixture was stirred for 1 h at RT after which it was concentrated. The residue was purified by preparative HPLC to give 1-[5-(5-chloro-thiophen-2-yl)-isoxazol-3-ylmethyl]-3,5-dimethyl-4-(perhydro-1,4-oxazepine-4-sulfonyl)-1H-pyrrole-2-carboxylic acid (1-isopropyl-piperidin-4-yl)-amide as its trifluoroacetate salt (90 mg). MS ($ESI^+$): m/e=623 $[M+H]^+$, chloro pattern.

Example 23

4-Bromo-1-[5-(5-chloro-thiophen-2-yl)-isoxazol-3-ylmethyl]-3,5-dimethyl-1H-pyrrole-2-carboxylic acid (1-isopropyl-piperidin-4-yl)-amide (i) 4-Bromo-3,5-dimethyl-1H-pyrrole-2-carboxylic acid To 4-bromo-3,5-dimethyl-1H-pyrrole-2-carboxylic acid ethyl ester (900 mg) was added 10 mL of a solution of boron tribromide (1 M) in DCM. The mixture was stirred at RT for 16 hours (h), then heated under reflux for 5 h. To complete the reaction neat boron tribromide (1.5 mL) was added dropwise and refluxing was continued for 3 h. After cooling to RT the mixture was poured onto crushed ice and extracted with DCM. The combined organic phases were filtered through a plug of diatomaceous earth and concentrated under reduced pressure to give crude 4-bromo-3,5-dimethyl-1H-pyrrole-2-carboxylic acid (1.2 g) which was used directly in the next step.

(ii) 4-Bromo-3,5-dimethyl-1H-pyrrole-2-carboxylic acid (1-isopropyl-piperidin-4-yl)-amide To 4-bromo-3,5-dimethyl-1H-pyrrole-2-carboxylic acid (570 mg) in DCM (15 mL) was added DIEA (2.11 g), HATU (994 mg) and 1-isopropyl-piperidin-4-ylamine (372 mg). The mixture was stirred for 16 h at RT after which it was concentrated. The residue was purified by preparative HPLC to give 4-bromo-3,5-dimethyl-1H-pyrrole-2-carboxylic acid (1-isopropyl-piperidin-4-yl)-amide (65 mg) which was directly used in the next step.

(iii) 4-Bromo-1-[5-(5-chloro-thiophen-2-yl)-isoxazol-3-ylmethyl]-3,5-dimethyl-1H-pyrrole-2-carboxylic acid (1-isopropyl-piperidin-4-yl)-amide To a solution of 4-bromo-3,5-dimethyl-1H-pyrrole-2-carboxylic acid (1-isopropyl-piperidin-4-yl)-amide (33 mg) in a mixture of DMF (2 mL) and DCM (2 mL) was added $Cs_2CO_3$ (62 mg). The mixture was stirred for 30 min at RT after which 3-bromomethyl-5-(5-chloro-thiophen-2-yl)-isoxazole (84 mg) was added. The mixture was stirred for 1 h at RT. $Cs_2CO_3$ (62 mg) was added and stirring was continued for 48 h at RT whereupon the mixture was filtered and concentrated. The residue was subjected to preparative HPLC ($CH_3CN/H_2O$ gradient+0.05% TFA) to give 4-Bromo-1-[5-(5-chlorothiophen-2-yl)-isoxazol-3-ylmethyl]-3,5-dimethyl-1H-pyrrole-2-carboxylic acid (1-isopropyl-piperidin-4-yl)-amide as its trifluoroacetate salt (9 mg). MS (ESI$^+$): m/e=539 [M+H]$^+$, chloro pattern.

Example 24

4-Bromo-1-[(5-chloro-pyridin-2-ylcarbamoyl)-methyl]-3,5-dimethyl-1H-pyrrole-2-carboxylic acid (1-isopropyl-piperidin-4-yl)-amide (i) 4-Bromo-1-[(5-chloro-pyridin-2-ylcarbamoyl)-methyl]-3,5-dimethyl-1H-pyrrole-2-carboxylic acid ethyl ester To a solution of 4-bromo-3,5-dimethyl-1H-pyrrole-2-carboxylic acid ethyl ester (492 mg) in DMF (5 mL) was added $Cs_2CO_3$ (912 mg). The mixture was stirred for 30 min at RT after which 2-bromo-N-(5-chloro-pyridin-2-yl)-acetamide (499 mg) was added. Stirring was continued for 2 h at RT whereupon the mixture was filtered and concentrated. The residue was subjected to preparative HPLC($CH_3CN/H_2O$ gradient+0.05% TFA) to give 4-bromo-1-[(5-chloro-pyridin-2-ylcarbamoyl)-methyl]-3,5-dimethyl-1H-pyrrole-2-carboxylic acid ethyl ester (220 mg).

(ii) 4-Bromo-1-[(5-chloro-pyridin-2-ylcarbamoyl)-methyl]-3,5-dimethyl-1H-pyrrole-2-carboxylic acid To 220 mg of the foregoing ester was added neat boron tribromide (1.5 mL) dropwise. The mixture was refluxed for 8 h. More boron tribromide (1.5 mL) was added dropwise and refluxing was continued for 3 h whereupon the mixture was poured onto crushed ice after cooling to RT. The phases were separated and the aqueous phase was extracted with DCM. The combined organic phases were washed with brine, dried ($MgSO_4$) and concentrated in vacuo to give crude 4-Bromo-1-[(5-chloro-pyridin-2-ylcarbamoyl)-methyl]-3,5-dimethyl-1H-pyrrole-2-carboxylic acid (200 mg) which was directly used in the next step.

(iii) 4-Bromo-1-[5-(5-chloro-thiophen-2-yl)-isoxazol-3-ylmethyl]-3,5-dimethyl-1H-pyrrole-2-carboxylic acid (1-isopropyl-piperidin-4-yl)-amide To the foregoing crude acid (200 mg) in DCM (2 mL) was added DIEA (33 mg), HATU (49 mg) and 1-isopropyl-piperidin-4-ylamine (18 mg). The mixture was stirred for 16 h at RT after which it was concentrated. The residue was subjected to preparative HPLC($CH_3CN/H_2O$ gradient+0.05% TFA) to give 4-bromo-1-[5-(5-chloro-thiophen-2-yl)-isoxazol-3-ylmethyl]-3,5-dimethyl-1H-pyrrole-2-carboxylic acid (1-isopropyl-piperidin-4-yl)-amide as its trifluoroacetate salt (19 mg). MS (ESI$^+$): m/e=510 [M+H]$^+$, chloro pattern.

Example 25

1-[5-(5-Chloro-thiophen-2-yl)-isoxazol-3-ylmethyl]-4-formyl-3,5-dimethyl-1H-pyrrole-2-carboxylic acid (1-isopropyl-piperidin-4-yl)-amide (i) 1-[5-(5-Chloro-thiophen-2-yl)-isoxazol-3-ylmethyl]-4-formyl-3,5-dimethyl-1H-pyrrole-2-carboxylic acid ethyl ester To 4-formyl-3,5-dimethyl-1H-pyrrole-2-carboxylic acid ethyl ester (2.60 g) in DMF (26 mL) was added $Cs_2CO_3$ (6.51 g). The mixture was stirred for 30 min at RT, then 3-bromomethyl-5-(5-chloro-thiophen-2-yl)-isoxazole (3.71 g) was added. Stirring was continued for 2 h at RT. Water was added and the phases were separated. The aqueous phase was extracted with DCM. The combined organic phases were washed with brine, dried ($MgSO_4$) and was concentrated under reduced pressure to give crude 1-[5-(5-chloro-thiophen-2-yl)-isoxazol-3-ylmethyl]-4-formyl-3,5-dimethyl-1H-pyrrole-2-carboxylic acid ethyl ester (4.20 g), which was directly used in the next step without further purification.

(ii) 1-[5-(5-Chloro-thiophen-2-yl)-isoxazol-3-ylmethyl]-4-formyl-3,5-dimethyl-1H-pyrrole-2-carboxylic acid To a solution of the foregoing ester in a mixture of THF p. 5 mL) and water (2.5 mL) was added lithium hydroxide monohydrate (55 mg). The mixture was stirred for 2 h at 60° C. More lithium hydroxide monohydrate (60 mg) was added and the mixture was refluxed for 4 h. After cooling to RT the mixture was concentrated, acidified to pH 3 with 2N HCl and extracted with ethyl acetate. The combined organic phases were washed with brine, dried ($MgSO_4$) and concentrated under reduced pressure to give crude 1-[5-(5-chloro-thiophen-2-yl)-isoxazol-3-ylmethyl]-4-formyl-3,5-dimethyl-1H-pyrrole-2-carboxylic acid (100 mg) which was directly used in the next step.

(iii) 1-[5-(5-Chloro-thiophen-2-yl)-isoxazol-3-ylmethyl]-4-formyl-3,5-dimethyl-1H-pyrrol e-2-carboxylic acid (1-isopropyl-piperidin-4-yl)-amide:

To the foregoing acid (100 mg) in DCM (2 mL) was added DIEA (142 mg), HATU (104 mg) and 1-isopropyl-piperidin-4-ylamine (39 mg). The mixture was stirred for 2 h at RT after which it was concentrated. The residue was subjected to preparative HPLC($CH_3CN/H_2O$ gradient+0.05% TFA) to give 1-[5-(-chloro-thiophen-2-yl)-isoxazol-3-ylmethyl]-4-formyl-3,5-dimethyl-1H-pyrrole-2-carboxylic acid (1-isopropyl-piperidin-4-yl)-amide as its trifluoroacetate salt (101 mg). MS (ESI$^+$): m/e=489 [M+H]$^+$, chloro pattern.

Pharmacological Testing

The ability of the compounds of the formulae I and Ia to inhibit factor Xa or factor VIIa or other enzymes like thrombin, plasmin, or trypsin can be assessed by determining the concentration of the compound of the formulae I and Ia that inhibits enzyme activity by 50%, i.e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formulae I and Ia. For calculating the inhibition constant Ki, the $IC_{50}$ value was corrected for competition with substrate using the formula $$Ki=IC50/\{1+(\text{substrate concentration}/Km)\}$$

wherein Km is the Michaelis-Menten constant (Chen and Prusoff, Biochem. Pharmacol. 22 (1973), 3099-3108; I. H.

Segal, Enzyme Kinetics, 1975, John Wiley & Sons, New York, 100-125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN$_3$) was used. The IC50 was determined by combining in appropriate wells of a Costar half-area microtiter plate 25 μl human factor Xa (Enzyme Research Laboratories, Inc.; South Bend, Indiana) in TBS-PEG; 40 μl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formulae I and Ia plus enzyme for 10 min. Then the assay was initiated by adding substrate to obtain a final volume of 100 μl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 μM.

b) Factor VIIa Assay

The inhibitory activity towards factor VIIa/tissue factor activity was determined using a chromogenic assay essentially as described previously 0. A. Ostrem et al., Biochemistry 37 (1998) 1053-1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 μl human factor VIIa and TF (5 nM and 10 nM, respective final concentration) combined with 40 μl of inhibitor dilutions in 10% DMSO/TBS-PEG buffer (50 mM Tris, 15 mM NaCl, 5 mM CaCl$_2$, 0.05% PEG 8000, pH 8.15). Following a 15-minutes preincubation period, the assay was initiated by the addition of 35 μl of the chromogenic substrate S-2288 (D-11e-Pro-Arg-p-nitroanilide, Pharmacia Hepar Inc., 500 μM final concentration). The results (inhibition constants Ki (FXa) for inhibition of factor Xa) are shown in Table 1.

TABLE 1

| Example | Ki(FXa) [μM] |
|---|---|
| 1 | 0.077 |
| 2 | 8.06 |
| 3 | 0.043 |
| 4 | 0.011 |
| 5 | 0.081 |
| 6 | 0.902 |
| 7 | 0.249 |
| 8 | 0.152 |
| 9 | 0.997 |
| 10 | 0.007 |
| 11 | 0.294 |
| 12 | 34.88 |
| 13 | 9.576 |
| 14 | 0.059 |
| 15 | 41.285 |
| 16 | 1.439 |
| 17 | 8.99 |
| 18 | 0.036 |
| 19 | 0.088 |
| 20 | 0.057 |

TABLE 1-continued

| Example | Ki(FXa) [μM] |
|---|---|
| 21 | 0.005 |
| 22 | 0.112 |
| 23 | 0.005 |
| 24 | 0.011 |
| 25 | 0.024 |

We claim:
1. A compound of formula I,

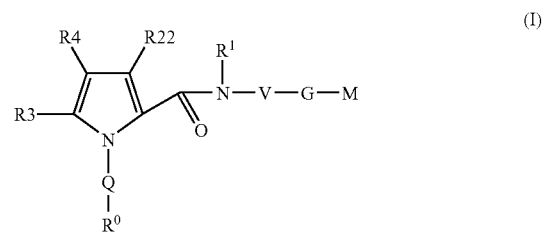

wherein
$R^0$ is 1) phenyl, wherein the phenyl is mono-substituted independently of one another by R8,
2) pyridyl, wherein the pyridyl is unsubstituted or mono-substituted independently of one another by R8, or
3) isoxazolyl, wherein the isooxazolyl is unsubstituted or mono-, di- or trisubstituted independently of one another by R8, and is additionally substituted by thienyl, wherein the thienyl is unsubstituted or mono-substituted independently of one another by R8,
R8 is fluorine, chlorine, bromine, or
—O—($C_1$-$C_8$)-alkyl,
Q is —($C_0$-$C_2$)-alkylene-C(O)—$NR^{10}$—, or —($C_1$-$C_6$)-alkylene, provided that Q is not —($C_1$-$C_6$)-alkylene, if $R^0$ is pyridyl,
$R^1$ is a hydrogen atom,
V is piperidine,
G is a direct bond,
M is —($C_1$-$C_8$)-alkyl,
R3, R4 and R22 are each independently
hydrogen atom,
halogen,
—($C_1$-$C_4$)-alkyl,
phenyl,
—$NO_2$,
—$SO_t$—N($R^{11}$)—$R^{12}$, wherein t is 2,
—($C_0$-$C_4$)-alkylene-C(O)—$R^{11}$,
—($C_0$-$C_4$)-alkylene-C(O)—O—$R^{11}$, or
—($C_0$-$C_4$)-alkylene-C(O)—N($R^{11}$)—$R^{12}$,
R11 and R12 are each independently
hydrogen atom,
—($C_1$-$C_6$)-alkyl, which is unsubstituted or mono-substituted independently of one another by R13, or
—($C_0$-$C_6$)-alkyl-phenyl, or
R11 and R12 together with the nitrogen atom to which they are attached form a ring selected from azetidine, or 1,4-oxazepine, which is unsubstituted or mono-substituted independently of one another by R13,
R13 is —($C_1$-$C_8$)-alkoxy, and
$R^{10}$ is hydrogen,
or a stereoisomeric form thereof, a mixture of the stereoisomeric forms thereof in any ratio, or a physiologically tolerable salt thereof.

2. The compound according to claim 1, wherein
R8 is F, Cl, Br,
   2) or
   3) —O—($C_1$-$C_4$)-alkyl, and
M is —($C_1$-$C_6$)-alkyl, or a stereoisomeric form thereof, a mixture of the stereoisomeric forms thereof in any ratio, or a physiologically tolerable salt thereof.

3. The compound according to claim 1, wherein
R8 is F, Cl, Br,
   —O—($C_1$-$C_4$)-alkyl,
Q is —($C_1$-$C_4$)-alkylene or —($C_0$-$C_2$)-alkylene-C(O)—$NR^{10}$—, provided that Q is not —($C_1$-$C_4$)-alkylene, if $R^o$ is pyridyl,
M is —($C_1$-$C_6$)-alkyl, and
R11 and R12 are each independently
   hydrogen atom, or
      —($C_1$-$C_4$)-alkyl, which is unsubstituted or mono-substituted independently of one another by R13,
R11 and R12 together with the nitrogen atom to which they are attached form a heterocyclic ring, which is selected from azetidine, or 1,4-oxazepine, or a stereoisomeric form thereof, a mixture of the stereoisomeric forms thereof in any ratio, or a physiologically tolerable salt thereof.

4. The compound according to claim 1, wherein
R8 is F, Cl, Br, or —O—$CH_3$—,
Q is —$CH_2$—C(O)—NH—, methylene or ethylene, provided that Q is not methylene or ethylene, if $R^o$ is pyridyl,
M is —($C_2$-$C_4$)-alkyl, and
R11 and R12 are each independently
   hydrogen atom,
      —($C_1$-$C_4$)-alkyl, which is unsubstituted or mono-substituted independently of one another by R13,
      —($C_0$-$C_6$)-alkyl-phenyl, or
R11 and R12 together with the nitrogen atom to which they are attached form a ring, selected from azetidine, or 1,4-oxazepine, or a stereoisomeric form thereof, a mixture of the stereoisomeric forms thereof in any ratio, or a physiologically tolerable salt thereof.

5. The compound according to claim 1, selected from
1-[5-(5-Chloro-thiophen-2-yl)-isoxazol-3-ylmethyl]-1H-pyrrole-2-carboxylic acid (1-isopropyl-piperidin-4-yl)-amide,
1-(3-Methoxy-benzyl)-1H-pyrrole-2-carboxylic acid (1-isopropyl-piperidin-4-yl)-amide,
1-[5-(5-Chloro-thiophen-2-yl)-isoxazol-3-ylmethyl]-4-nitro-1H-pyrrole-2-carboxylic acid (1-isopropyl-piperidin-4-yl)-amide,
1-[5-(5-Chloro-thiophen-2-yl)-isoxazol-3-ylmethyl]-3,5-dimethyl-1H-pyrrole-2-carboxylic acid (1-isopropyl-piperidin-4-yl)-amide,
1-[(5-Chloro-pyridin-2-ylcarbamoyl)-methyl]-4-(perhydro-1,4-oxazepine-4-carbonyl)-1H-pyrrole-2-carboxylic acid (1-isopropyl-piperidin-4-yl)-amide,
1-[(5-Chloro-pyridin-2-ylcarbamoyl)-methyl]-5-(perhydro-1,4-oxazepine-4-carbonyl)-1H-pyrrole-2-carboxylic acid (1-isopropyl-piperidin-4-yl)-amide,
1-[5-(5-Chloro-thiophen-2-yl)-isoxazol-3-ylmethyl]-5-(perhydro-1,4-oxazepine-4-carbonyl)-1H-pyrrole-2-carboxylic acid (1-isopropyl-piperidin-4-yl)-amide,
3-[1-[5-(5-Chloro-thiophen-2-yl)-isoxazol-3-ylmethyl]-5-(1-isopropyl-piperidin-4-ylcarbamoyl)-2,4-dimethyl-1H-pyrrol-3-yl]-propionic acid,
1-[5-(5-Chloro-thiophen-2-yl)-isoxazol-3-ylmethyl]-5-(1-isopropyl-piperidin-4-ylcarbamoyl)-1H-pyrrole-2-carboxylic acid benzyl ester,
1-[5-(5-Chloro-thiophen-2-yl)-isoxazol-3-ylmethyl]-5-(1-isopropyl-piperidin-4-ylcarbamoyl)-1H-pyrrole-2-carboxylic acid methyl ester,
1-[5-(5-Chloro-thiophen-2-yl)-isoxazol-3-ylmethyl]-5-(1-isopropyl-piperidin-4-ylcarbamoyl)-1H-pyrrole-2-carboxylic acid,
1[(5 Chloro-pyridin 2-ylcarbamoyl)-methyl]4-nitro-1H-pyrrole-2-carboxylic acid (1-isopropyl-piperidin-4-yl)-amide,
1-[5-(5-Chloro-thiophen-2-yl)-isoxazol-3-ylmethyl]-5-(3-methoxy-azetidine-1-carbonyl)-1H-pyrrole-2-carboxylic acid (1-isopropyl-piperidin-4-yl)-amide,
1-[5-(5-Chloro-thiophen-2-yl)-isoxazol-3-ylmethyl]-1H-pyrrole-2,5-dicarboxylic acid 2-[(1-isopropyl-piperidin-4-yl)-amide] 5-[(2-methoxy-ethyl)-amide],
1-[5-(5-Chloro-thiophen-2-yl)-isoxazol-3-ylmethyl]-1H-pyrrole-2,5-dicarboxylic acid 2-[(1-isopropyl-piperidin-4-yl)-amide] 5-[(2-methoxy-ethyl)-methyl-amide],
1-[5-(5-Chloro-thiophen-2-yl)-isoxazol-3-ylmethyl]-5-phenyl-1H-pyrrole-2-carboxylic acid (1-isopropyl-piperidin-4-yl)-amide,
1-[5-(5-Chloro-thiophen-2-yl)-isoxazol-3-ylmethyl]-3,5-dimethyl-4-(perhydro-1,4-oxazepine-4-sulfonyl)-1H-pyrrole-2-carboxylic acid (1-isopropyl-piperidin-4-yl)-amide,
4-Bromo-1-[5-(5-chloro-thiophen-2-yl)-isoxazol-3-ylmethyl]-3,5-dimethyl-1H-pyrrole-2-carboxylic acid (1-isopropyl-piperidin-4-yl)-amide,
4-Bromo-1-[(5-chloro-pyridin-2-ylcarbamoyl)-methyl]-3,5-dimethyl-1H-pyrrole-2-carboxylic acid (1-isopropyl-piperidin-4-yl)-amide or
1-[5-(5-Chloro-thiophen-2-yl)-isoxazol-3-ylmethyl]-4-formyl-3,5-dimethyl-1H-pyrrole-2-carboxylic acid (1-isopropyl-piperidin-4-yl)-amide,
or a stereoisomeric form thereof, a mixture of the stereoisomeric forms thereof in any ratio, or a physiologically tolerable salt thereof.

6. A process for preparing a compound according to claim 1, comprising condensing a compound of formula 2 with a compound of formula $HR^{8'}$ to give a compound of formula 3 and optionally converting the compound of the formula 3 into a compound of the formula I,

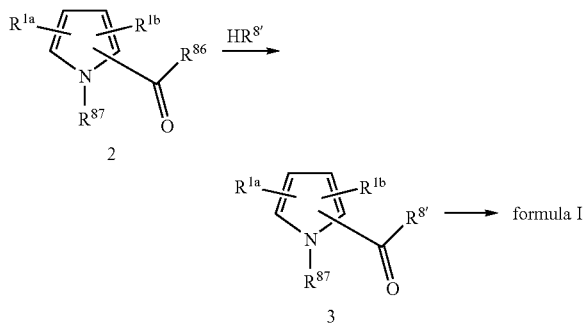

wherein, $R^{8'}$ is —N($R^1$)—V—G—M as defined in claim 1 or a group that is capable of being transformed into —N($R^1$)—V—G—M as defined in claim 1, $R^{87}$ is $R^o$ as defined in claim 1 or a group that is capable of being transformed into —Q—$R^o$ as defined in claim 1,
—C(O)—$R^{86}$ is a carboxylic acid group or a derivative thereof, and $R^{1a}$ and $R^{1b}$ have the corresponding definitions of R3 and R4 as defined in claim 1, respectively, or a functional group in them can also be present in a protected form or in a form of precursor group.

7. A pharmaceutical composition comprising a pharmaceutically effective amount of the compound according to claim 1, or a stereoisomeric form thereof, a mixture of the stereoisomeric forms thereof in any ratio, or a physiologically tolerable salt thereof, and a pharmaceutically acceptable carrier.

8. A method for treating vascular restenosis following angioplasty in a patient in need thereof, comprising administering to the patient a pharmaceutically effective amount of the compound according to claim 1, or a stereoisomeric form thereof, a mixture of the stereoisomeric forms thereof in any ratio, or a physiologically tolerable salt thereof.

9. A method for treating vascular restenosis following percutaneous transluminal coronary angioplasty in a patient in need thereof, comprising administering to the patient a pharmaceutically effective amount of the compound according to claim 1, or a stereoisomeric form thereof, a mixture of the stereoisomeric forms thereof in any ratio, or a physiologically tolerable salt thereof.

* * * * *